United States Patent
Ohgi et al.

(10) Patent No.: US 9,663,784 B2
(45) Date of Patent: May 30, 2017

(54) SINGLE-STRANDED NUCLEIC ACID MOLECULE FOR REGULATING EXPRESSION OF GENE HAVING DELIVERING FUNCTION

(71) Applicant: Bonac Corporation, Kurume-shi, Fukuoka (JP)

(72) Inventors: Tadaaki Ohgi, Kurume (JP); Eriko Aoki, Kurume (JP); Chisato Emura, Fukuoka (JP); Tomohiro Hamasaki, Kurume (JP)

(73) Assignee: Bonac Corporation, Kurume (JP)

( * ) Notice: Subject to any disclaimer, the term of this patent is extended or adjusted under 35 U.S.C. 154(b) by 0 days.

(21) Appl. No.: 14/403,259

(22) PCT Filed: May 25, 2013

(86) PCT No.: PCT/JP2013/064541
§ 371 (c)(1),
(2) Date: Nov. 24, 2014

(87) PCT Pub. No.: WO2013/180038
PCT Pub. Date: Dec. 5, 2013

(65) Prior Publication Data
US 2015/0105443 A1   Apr. 16, 2015

(30) Foreign Application Priority Data
May 26, 2012   (JP) ................. 2012-120337

(51) Int. Cl.
*A61K 47/48*   (2006.01)
*C12N 15/113*   (2010.01)
*A61K 48/00*   (2006.01)

(52) U.S. Cl.
CPC ...... *C12N 15/113* (2013.01); *A61K 47/48038* (2013.01); *A61K 47/48046* (2013.01);
(Continued)

(58) Field of Classification Search
CPC ................................. A61K 47/48038
See application file for complete search history.

(56) References Cited

U.S. PATENT DOCUMENTS

| 7,655,768 B2 | 2/2010 | Ohgi et al. |
| 2002/0042059 A1* | 4/2002 | Makarov ............. C12Q 1/6855 435/6.1 |

(Continued)

FOREIGN PATENT DOCUMENTS

| CN | 101981185 A | 2/2011 |
| EP | 2 436 767 A1 | 4/2012 |

(Continued)

OTHER PUBLICATIONS

Fire et al., "Potent and specific genetic interference by double-stranded RNA in *Caenorhabditis elegans*," Nature, 391: 806-811 (Feb. 19, 1998).

(Continued)

*Primary Examiner* — Jennifer McDonald
(74) *Attorney, Agent, or Firm* — Leydig, Voit & Mayer, Ltd.

(57) ABSTRACT

The invention provides a single-stranded nucleic acid capable of inhibiting expression of a target gene having a delivery function. The nucleic acid contains, from the 5'-side to the 3'-side, a 5'-side region (Xc), a linker region (Lx), an inner region (Z), a linker region (Ly) and a 3'-side region (Yc) in this order, wherein the inner region (Z) is constituted by linkage of the inner 5'-side region (X) and the inner 3'-side region (Y), the 5'-side region (Xc) is complementary to the inner 5'-side region (X), the 3'-side region (Yc) is complementary to the inner 3'-side region (Y), at least one of the inner region (Z), the 5'-side region (Xc) and the 3'-side region (Yc) comprises an expression inhibitory sequence that inhibits expression of a target gene, and at least one of (Continued)

the 5'-terminus, the 3'-terminus, the linker region (Lx) and the linker region (Ly) is bound to a bio-related substance.

20 Claims, 10 Drawing Sheets

(52) U.S. Cl.
CPC .. *A61K 47/48053* (2013.01); *A61K 47/48092* (2013.01); *A61K 47/48107* (2013.01); *A61K 47/48123* (2013.01); *A61K 47/48246* (2013.01); *A61K 48/00* (2013.01); *C12N 2310/14* (2013.01); *C12N 2310/531* (2013.01); *C12N 2310/533* (2013.01)

(56) References Cited

U.S. PATENT DOCUMENTS

| | | | |
|---|---|---|---|
| 2004/0110296 A1* | 6/2004 | Vargeese | A61K 47/48053 435/458 |
| 2005/0222009 A1 | 10/2005 | Lamensdorf et al. | |
| 2007/0244058 A1 | 10/2007 | Ohgi et al. | |
| 2009/0239814 A1* | 9/2009 | Manoharan | A61K 47/48092 514/26 |
| 2009/0292005 A1 | 11/2009 | Ohgi et al. | |
| 2010/0137407 A1 | 6/2010 | Abe et al. | |
| 2011/0034545 A1 | 2/2011 | Kubo et al. | |
| 2011/0064792 A1 | 3/2011 | Humphries et al. | |
| 2011/0159586 A1* | 6/2011 | Hauser | A61K 31/70 435/375 |
| 2011/0200582 A1 | 8/2011 | Baryza et al. | |
| 2012/0010271 A1 | 1/2012 | Ohgi et al. | |
| 2012/0184598 A1* | 7/2012 | Hauser | C12N 15/111 514/44 A |

FOREIGN PATENT DOCUMENTS

| | | |
|---|---|---|
| EP | 2 527 440 A1 | 11/2012 |
| JP | 2007-508030 A | 4/2007 |
| JP | 2008-220366 A | 9/2008 |
| JP | 2008-278784 A | 11/2008 |
| JP | 2011-501662 A | 1/2011 |
| WO | WO 2004/015075 A2 | 2/2004 |
| WO | WO 2006/022325 A1 | 3/2006 |
| WO | WO 2007/099981 A1 | 9/2007 |
| WO | WO 2007/131237 A2 | 11/2007 |
| WO | WO 2009/054551 A2 | 4/2009 |
| WO | WO 2011/076807 A2 | 6/2011 |
| WO | WO 2012/005368 A1 | 1/2012 |

OTHER PUBLICATIONS

Sonoke et al., "Tumor Regression in Mice by Delivery of Bcl-2 Small Interfering RNA with Pegylated Cationic Liposomes," *Cancer Research*, 68(21): 8843-8851 (Nov. 1, 2008).

Japanese Patent Office, International Search Report in International Patent Application PCT/JP2013/064541 (Jul. 2, 2013).

Japanese Patent Office, Notice of Reasons for Refusal in Japanese Patent Application No. 2014-518427 (May 17, 2016).

Jakobsen et al., "Polyaza crown ethers as nonnucleosidic building blocks in DNA-conjugates," 234th American Chemical Society (ACS) National Meeting, Abstract BIOL-071 (Aug. 19, 2007).

Liu et al., "Membrane Anchored Immunostimulatory Oligonucleotides for in Vivo Cell Modification and Localized Immunotherapy," *Angewandte Chemie, International Edition*, 50(31): 7052-7055 (2011).

Liu et al., "Membrane Anchored Immunostimulatory Oligonucleotides for in Vivo Cell Modification and Localized Immunotherapy," *Angewandte Chemie, International Edition*, 50(31): 7052-7055—supporting information retrieved on Dec. 12, 2011, from the Internet at URL: http://onlinelibrary.wiley.com/store/10.1002/anie.201101266/asset/supinfo/anie_201101266_sm_miscellaneous_information.pdf?v=1&s=03200f852de1ccff62b185fc32385108d1fe650f (2011).

European Patent Office, Communication Pursuant to Rule 164(1) EPC in European Patent Application No. 13797956.3 (Jan. 4, 2016).

Chinese Patent Office, Notification of the Second Office Action in Chinese Patent Application No. 201380028696.2 (Jul. 18, 2016).

\* cited by examiner

FIG. 1
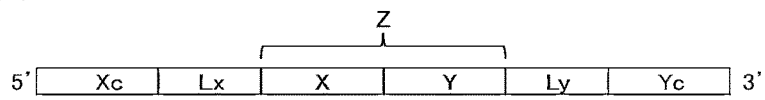
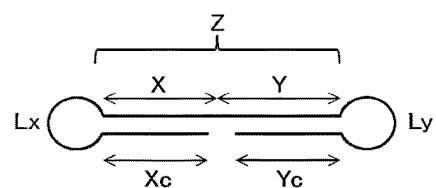
FIG. 2
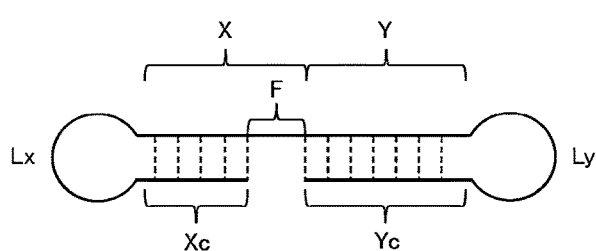
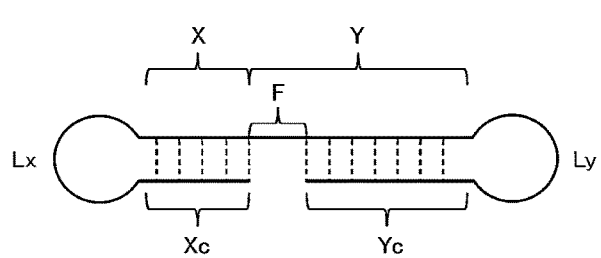
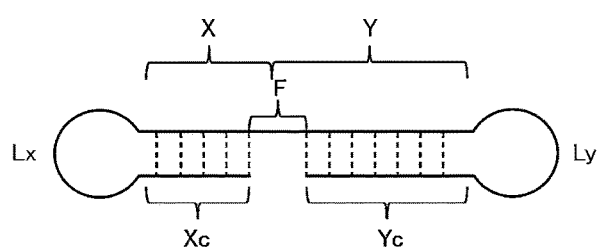
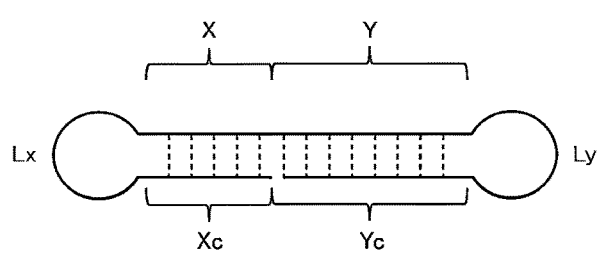

(a) 0101-C16

(b) Nontreat

Luciferase activity in brain

SEQUENCE LISTING

```
<160> NUMBER OF SEQ ID NOS: 19

<210> SEQ ID NO 1
<211> LENGTH: 21
<212> TYPE: DNA
<213> ORGANISM: Artificial Sequence
<220> FEATURE:
<223> OTHER INFORMATION: Synthetic nucleic acid molecule

<400> SEQUENCE: 1
cuuacgcuga guacuucgat t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic nucleic acid molecule

<400> SEQUENCE: 2
ucgaaguacu cagcguaagt t                                              21

<210> SEQ ID NO 3
<211> LENGTH: 24
<212> TYPE: RNA
<213> ORGANISM: Artificial Sequence
<220> FEATURE:
```

<223> OTHER INFORMATION: Synthetic nucleic acid molecule

<400> SEQUENCE: 3
acuuacgcug aguacuucga uucc                                    24

<210> SEQ ID NO 4
<211> LENGTH: 26
<212> TYPE: RNA
<213> ORGANISM: Artificial Sequence
<220> FEATURE:
<223> OTHER INFORMATION: Synthetic nucleic acid molecule

<400> SEQUENCE: 4
ggaaucgaag uacucagcgu aaguuc                                  26

<210> SEQ ID NO 5
<211> LENGTH: 62
<212> TYPE: RNA
<213> ORGANISM: Artificial Sequence
<220> FEATURE:
<223> OTHER INFORMATION: Synthetic nucleic acid molecule

<400> SEQUENCE: 5
acuuacgcug aguacuucga uuccccacac cggaaucgaa guacucagcg uaaguucuuc    60
gg                                                                 62

<210> SEQ ID NO 6
<211> LENGTH: 51
<212> TYPE: RNA
<213> ORGANISM: Artificial Sequence
<220> FEATURE:
<223> OTHER INFORMATION: Synthetic nucleic acid molecule

<400> SEQUENCE: 6
acuuacgcug aguacuucga uuccggaauc gaaguacuca gcguaaguuc g            51

<210> SEQ ID NO 7
<211> LENGTH: 21
<212> TYPE: DNA
<213> ORGANISM: Artificial Sequence
<220> FEATURE:
<223> OTHER INFORMATION: Synthetic nucleic acid molecule

<400> SEQUENCE: 7
uacuauucga cacgcgaagt t                                       21

<210> SEQ ID NO 8
<211> LENGTH: 21
<212> TYPE: DNA
<213> ORGANISM: Artificial Sequence
<220> FEATURE:
<223> OTHER INFORMATION: Synthetic nucleic acid molecule

<400> SEQUENCE: 8
cuucgcgugu cgaauaguat t                                       21

<210> SEQ ID NO 9
<211> LENGTH: 21
<212> TYPE: DNA
<213> ORGANISM: Artificial Sequence
<220> FEATURE:
<223> OTHER INFORMATION: Synthetic nucleic acid molecule

<400> SEQUENCE: 9
uacuauucga cacgcgaagt t                                       21

<210> SEQ ID NO 10
<211> LENGTH: 24
<212> TYPE: RNA
<213> ORGANISM: Artificial Sequence
<220> FEATURE:
<223> OTHER INFORMATION: Synthetic nucleic acid molecule

<400> SEQUENCE: 10
acuuacgcug aguacuucga uucc                                    24

<210> SEQ ID NO 11
<211> LENGTH: 55
<212> TYPE: RNA
<213> ORGANISM: Artificial Sequence
<220> FEATURE:
<223> OTHER INFORMATION: Synthetic nucleic acid molecule

<400> SEQUENCE: 11
acuuacgcug aguacuucga uuccggaauc gaaguacuca gcguaaguuc uucgg    55

<210> SEQ ID NO 12
<211> LENGTH: 55
<212> TYPE: RNA
<213> ORGANISM: Artificial Sequence
<220> FEATURE:
<223> OTHER INFORMATION: Synthetic nucleic acid molecule

<400> SEQUENCE: 12
acuuacgcug aguacuucga uuccggaauc gaaguacuca gcguaaguuc uucgg    55

<210> SEQ ID NO 13
<211> LENGTH: 58
<212> TYPE: RNA
<213> ORGANISM: Artificial Sequence
<220> FEATURE:
<223> OTHER INFORMATION: Synthetic nucleic acid molecule

<400> SEQUENCE: 13
acuuacgcug aguacuucga uuccccacac cggaaucgaa guacucagcg uaaguucg  58

<210> SEQ ID NO 14
<211> LENGTH: 58
<212> TYPE: RNA
<213> ORGANISM: Artificial Sequence
<220> FEATURE:
<223> OTHER INFORMATION: Synthetic nucleic acid molecule

<400> SEQUENCE: 14
acuuacgcug aguacuucga uuccccacac cggaaucgaa guacucagcg uaaguucg  58

<210> SEQ ID NO 15
<211> LENGTH: 51
<212> TYPE: RNA
<213> ORGANISM: Artificial Sequence
<220> FEATURE:
<223> OTHER INFORMATION: Synthetic nucleic acid molecule

<400> SEQUENCE: 15
acuuacgcug aguacuucga uuccggaauc gaaguacuca gcguaaguuc g         51

<210> SEQ ID NO 16
<211> LENGTH: 51
<212> TYPE: RNA
<213> ORGANISM: Artificial Sequence
<220> FEATURE:

-continued

```
<223> OTHER INFORMATION: Synthetic nucleic acid molecule

<400> SEQUENCE: 16
acuuacgcug aguacuucga uuccggaauc gaaguacuca gcguaaguuc g            51

<210> SEQ ID NO 17
<211> LENGTH: 31
<212> TYPE: RNA
<213> ORGANISM: Artificial Sequence
<220> FEATURE:
<223> OTHER INFORMATION: Synthetic nucleic acid molecule

<400> SEQUENCE: 17
ggaaucgaag uacucagcgu aaguucuucg g                                 31

<210> SEQ ID NO 18
<211> LENGTH: 57
<212> TYPE: RNA
<213> ORGANISM: Artificial Sequence
<220> FEATURE:
<223> OTHER INFORMATION: Synthetic nucleic acid molecule

<400> SEQUENCE: 18
acuuacgcug aguacuucga uuccccacac cggaaucgaa guacucagcg uaaguuc     57

<210> SEQ ID NO 19
<211> LENGTH: 26
<212> TYPE: RNA
<213> ORGANISM: Artificial Sequence
<220> FEATURE:
<223> OTHER INFORMATION: Synthetic nucleic acid molecule

<400> SEQUENCE: 19
ggaaucgaag uacucagcgu aaguuc                                       26
```

US 9,663,784 B2

SINGLE-STRANDED NUCLEIC ACID MOLECULE FOR REGULATING EXPRESSION OF GENE HAVING DELIVERING FUNCTION

CROSS-REFERENCE TO RELATED APPLICATIONS

This patent application is the U.S. national phase of International Patent Application No. PCT/JP2013/064541, filed May 25, 2013, which claims the benefit of Japanese Patent Application No. 2012-120337, filed on May 26, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 4,282 bytes ASCII (Text) file named "719172SequenceListing.txt," created Nov. 21, 2014.

TECHNICAL FIELD

The present invention relates to a single-stranded nucleic acid molecule for inhibiting expression of a gene having a delivery function, a composition containing same and use thereof.

BACKGROUND ART

As a technique for inhibiting gene expression, for example, RNA interference (RNAi) is known (Non-Patent Document 1). Inhibition of gene expression by RNA interference is generally carried out, for example, by administering a short double-stranded RNA molecule to a cell or the like. The aforementioned double-stranded RNA molecule is generally called siRNA (small interfering RNA). It has been reported that gene expression can also be inhibited by a circular RNA molecule having a double strand partially formed therein by intramolecular annealing (Patent Document 1). However, in these techniques, the RNA molecules to induce the inhibition of the gene expression have the following problems.

First, in order to produce the aforementioned siRNA, it is necessary to synthesize a sense strand and an antisense strand separately and to hybridize these strands at the end of the process. Thus, there is a problem of low manufacturing efficiency. Furthermore, when the aforementioned siRNA is administered to a cell, it is necessary to administer the siRNA to the cell while repressing the dissociation to single-stranded RNAs, which requires a laborious task of setting the conditions for handling the siRNA. The circular RNA molecule has a problem in that its synthesis is difficult. To deal with the situation, the present inventors constructed a new single-stranded nucleic acid molecule having a two-loop structure produced by self-annealing, which solves the problem (patent document 2).

DOCUMENT LIST

Patent Documents patent document 1: JP-A-2008-278784
patent document 2: WO 2012/005368

Non-Patent Document non-patent document 1: Fire, et al., Nature, vol. 391, p. 806-811, 1998

SUMMARY OF THE INVENTION

Problems to be Solved by the Invention

Moreover, such new single-stranded nucleic acid molecule is requested to further realize a superior delivery function to the target.

Accordingly, the present invention aims to provide a single-stranded nucleic acid capable of inhibiting expression of a target gene having a delivery function.

Means of Solving the Problems

To achieve the aforementioned object, the single-stranded nucleic acid molecule of the present invention is a single-stranded nucleic acid molecule for inhibiting expression of a target gene having a delivery function, which comprises, from the 5'-side to the 3'-side, a 5'-side region (Xc), a linker region (Lx), an inner region (Z), a linker region (Ly) and a 3'-side region (Yc) in this order, wherein
the aforementioned inner region (Z) is constituted by linkage of an inner 5'-side region (X) and an inner 3'-side region (Y),
the aforementioned 5'-side region (Xc) is complementary to the aforementioned inner 5'-side region (X),
the aforementioned 3'-side region (Yc) is complementary to the aforementioned inner 3'-side region (Y),
at least one of the aforementioned inner region (Z), the aforementioned 5'-side region (Xc) and the aforementioned 3'-side region (Yc) comprises an expression inhibitory sequence that inhibits expression of a target gene, and
at least one selected from the group consisting of the 5'-terminus, the 3'-terminus, the aforementioned linker region (Lx) and the aforementioned linker region (Ly) is bound to a bio-related substance.

Effect of the Invention

The single-stranded nucleic acid molecule of the present invention can realize a superior delivering ability to a target without essentially requiring, for example, a carrier for the delivery. Therefore, for example, the toxicity of the carrier does not need to be considered, and a study for setting various conditions relating to the formation of a complex of a nucleic acid molecule and a carrier can be obviated. Consequently, for example, the labor and cost in terms of production and use can be reduced.

BRIEF DESCRIPTION OF THE DRAWINGS

FIG. 1 shows schematic views illustrating an example of the single-stranded nucleic acid molecule of the present invention.

FIG. 2 shows schematic views illustrating another example of the single-stranded nucleic acid molecule of the present invention.

of breast cancer cell line MCF-7 stably expressing firefly luciferase (pGL3 Luc) in the Example of the present invention.

Figure 5:
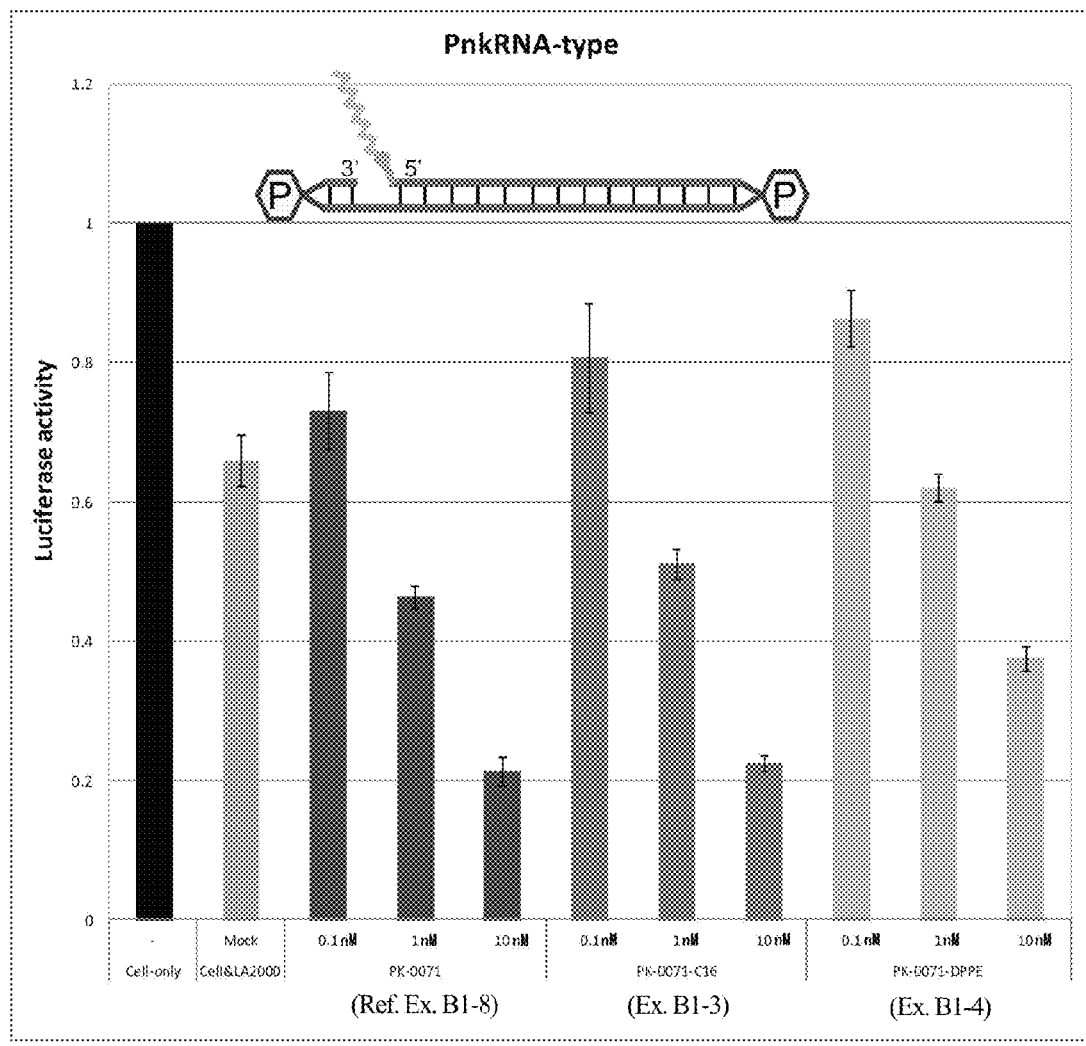

FIG. 5 is a still another graph showing the firefly luciferase gene expression inhibitory effect (relative activity of luciferase) of breast cancer cell line MCF-7 stably expressing firefly luciferase (pGL3 Luc) in the Example of the present invention.

Figure 6:
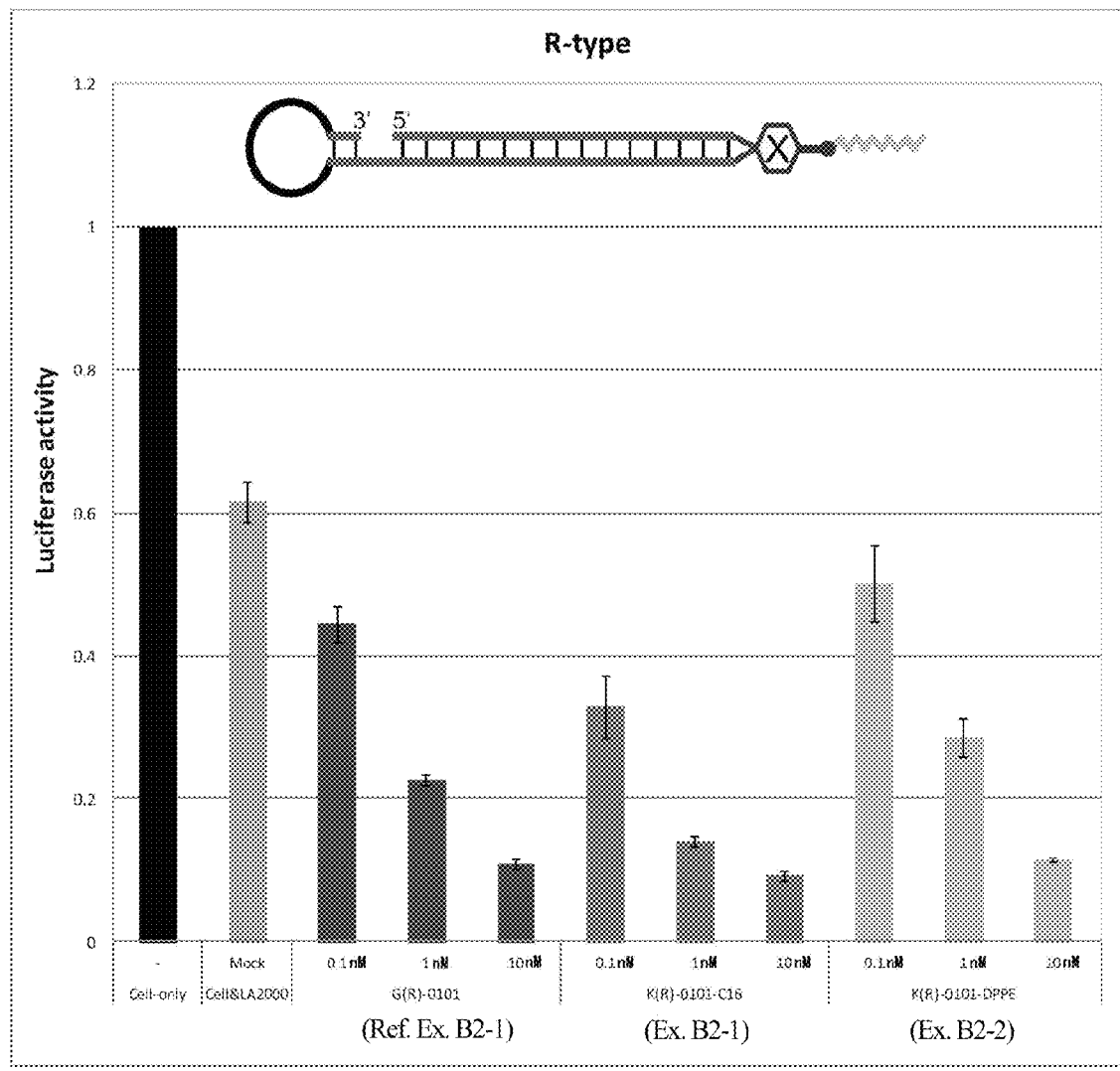

FIG. 6 is a still another graph showing the firefly luciferase gene expression inhibitory effect (relative activity of luciferase) of breast cancer cell line MCF-7 stably expressing firefly luciferase (pGL3 Luc) in the Example of the present invention.

Figure 7:
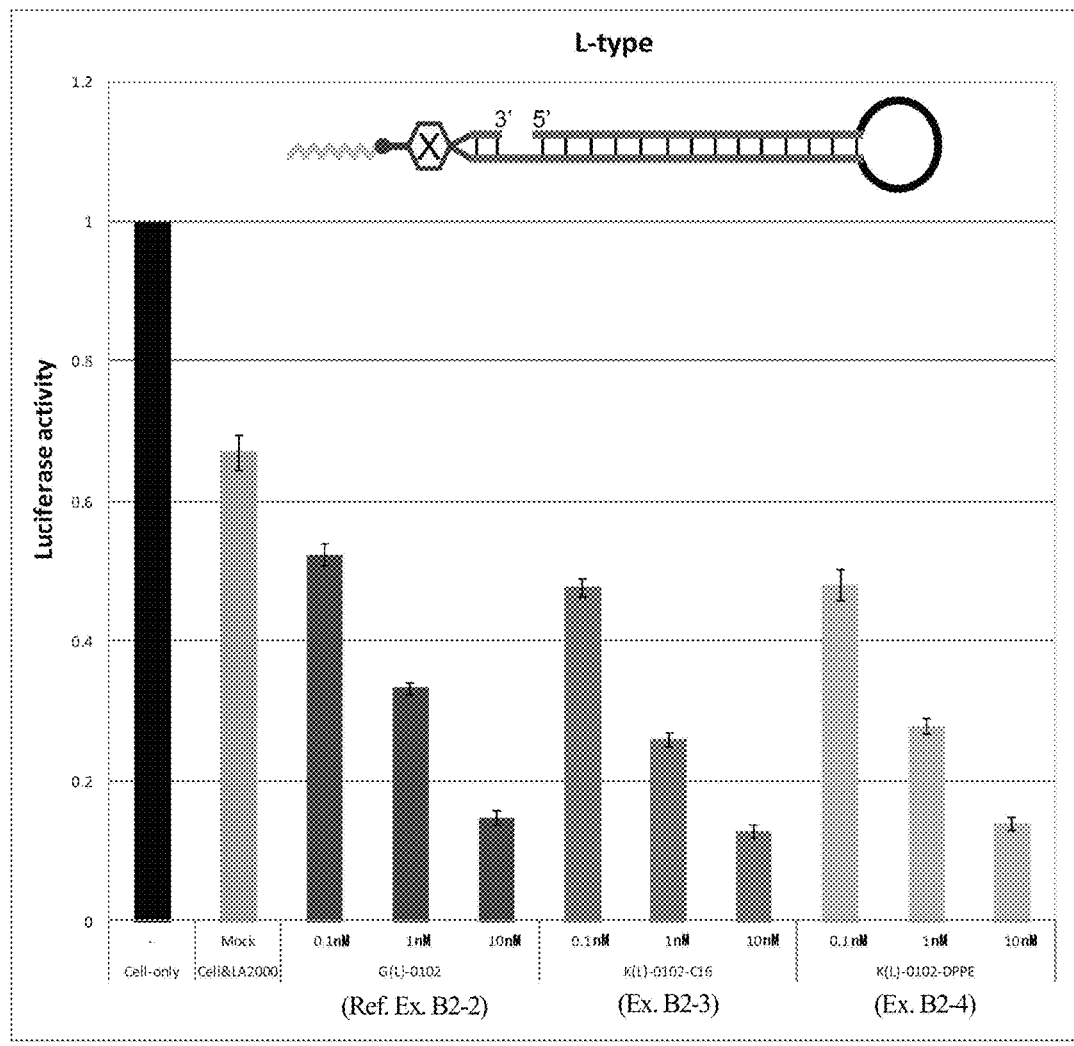

FIG. 7 is a still another graph showing the firefly luciferase gene expression inhibitory effect (relative activity of luciferase) of breast cancer cell line MCF-7 stably expressing firefly luciferase (pGL3 Luc) in the Example of the present invention.

Figure 8:
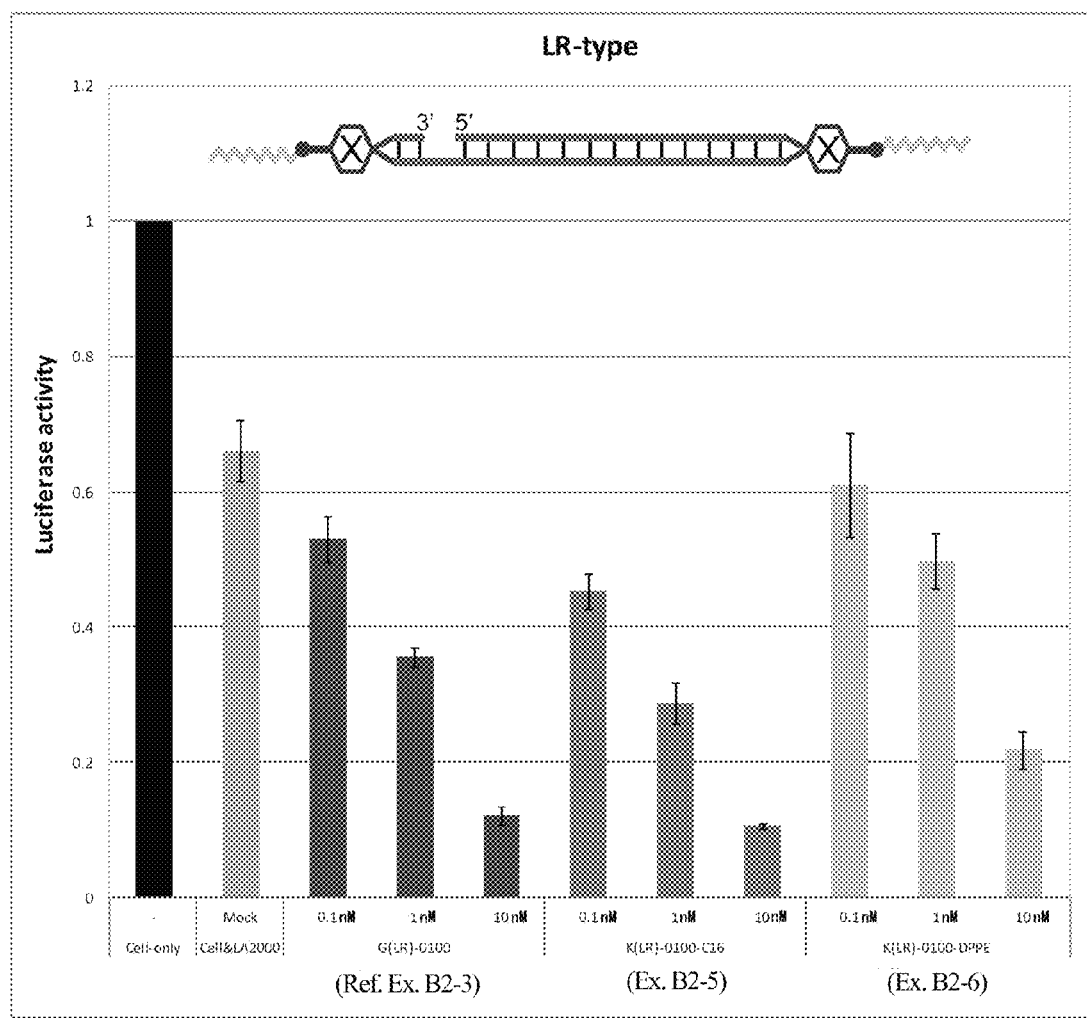

FIG. 8 is a still another graph showing the firefly luciferase gene expression inhibitory effect (relative activity of luciferase) of breast cancer cell line MCF-7 stably expressing firefly luciferase (pGL3 Luc) in the Example of the present invention.

Figure 9:
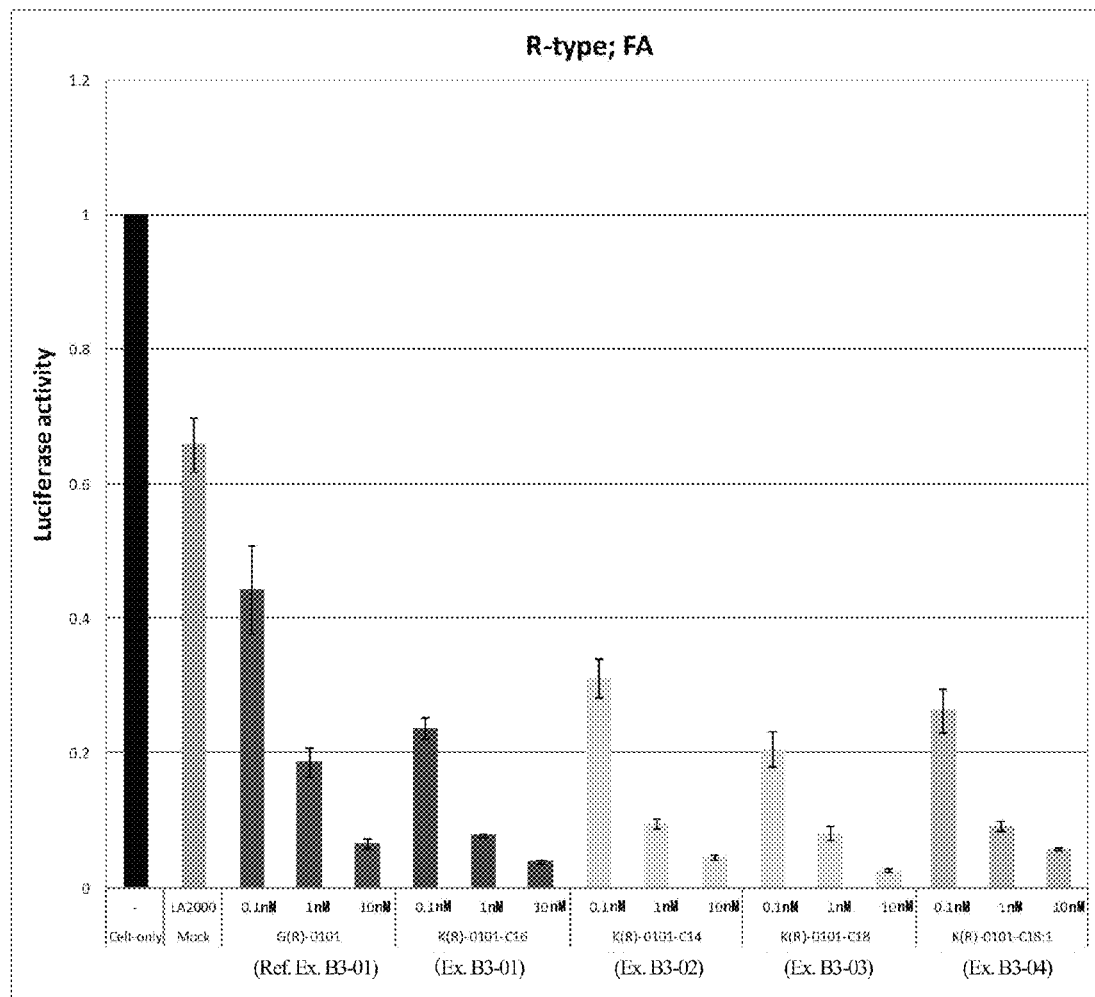

FIG. 9 is a still another graph showing the firefly luciferase gene expression inhibitory effect (relative activity of luciferase) of breast cancer cell line MCF-7 stably expressing firefly luciferase (pGL3 Luc) in the Example of the present invention.

Figure 10:
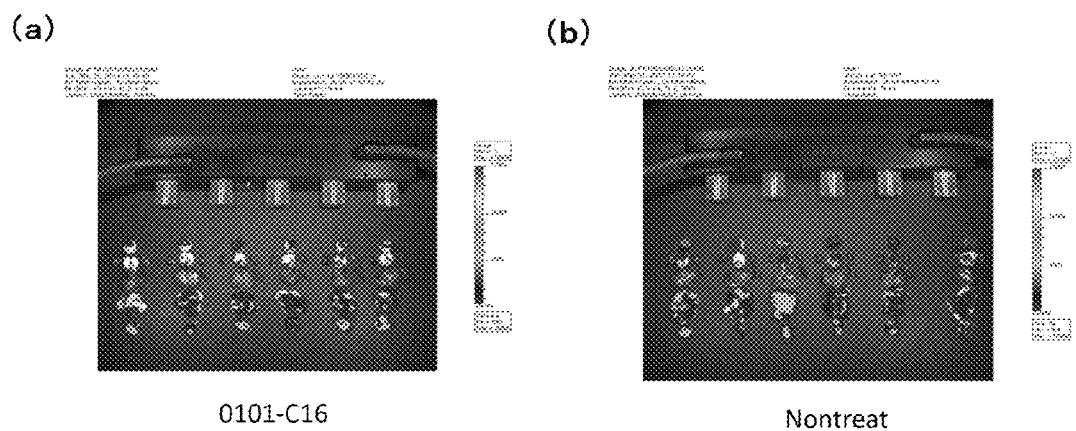

FIG. 10 shows photographs of the measurement results of inhibition of the expression of firefly luciferase gene in mouse in the Examples of the present invention. FIG. 10(a) is a photograph showing the measurement results of a mouse treated with the single-stranded nucleic acid of the present invention, and FIG. 10(b) is a photograph showing the measurement results of an untreated mouse.

Figure 11:
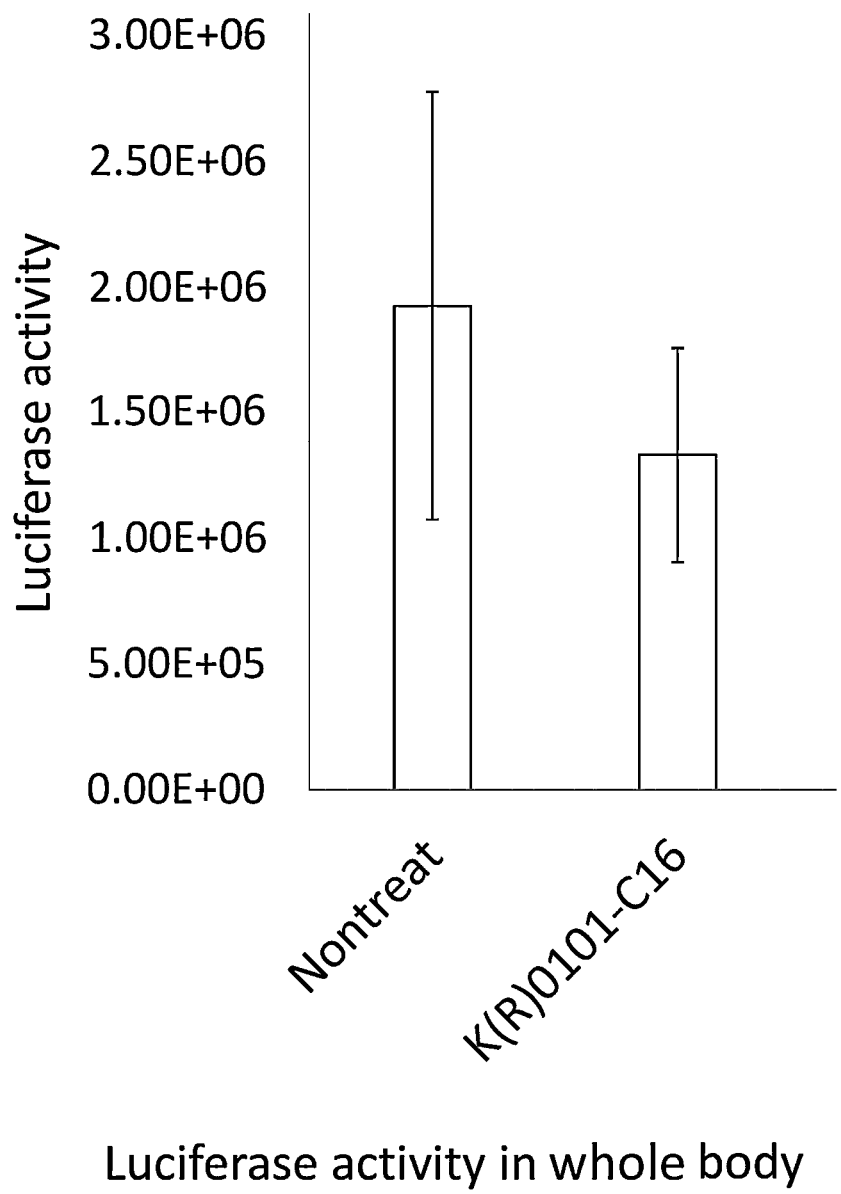

FIG. 11 is a graph showing the measurement results of the systemic luciferase activity (inhibition of expression of firefly luciferase gene) shown in the photograph of FIG. 10.

Figure 12:
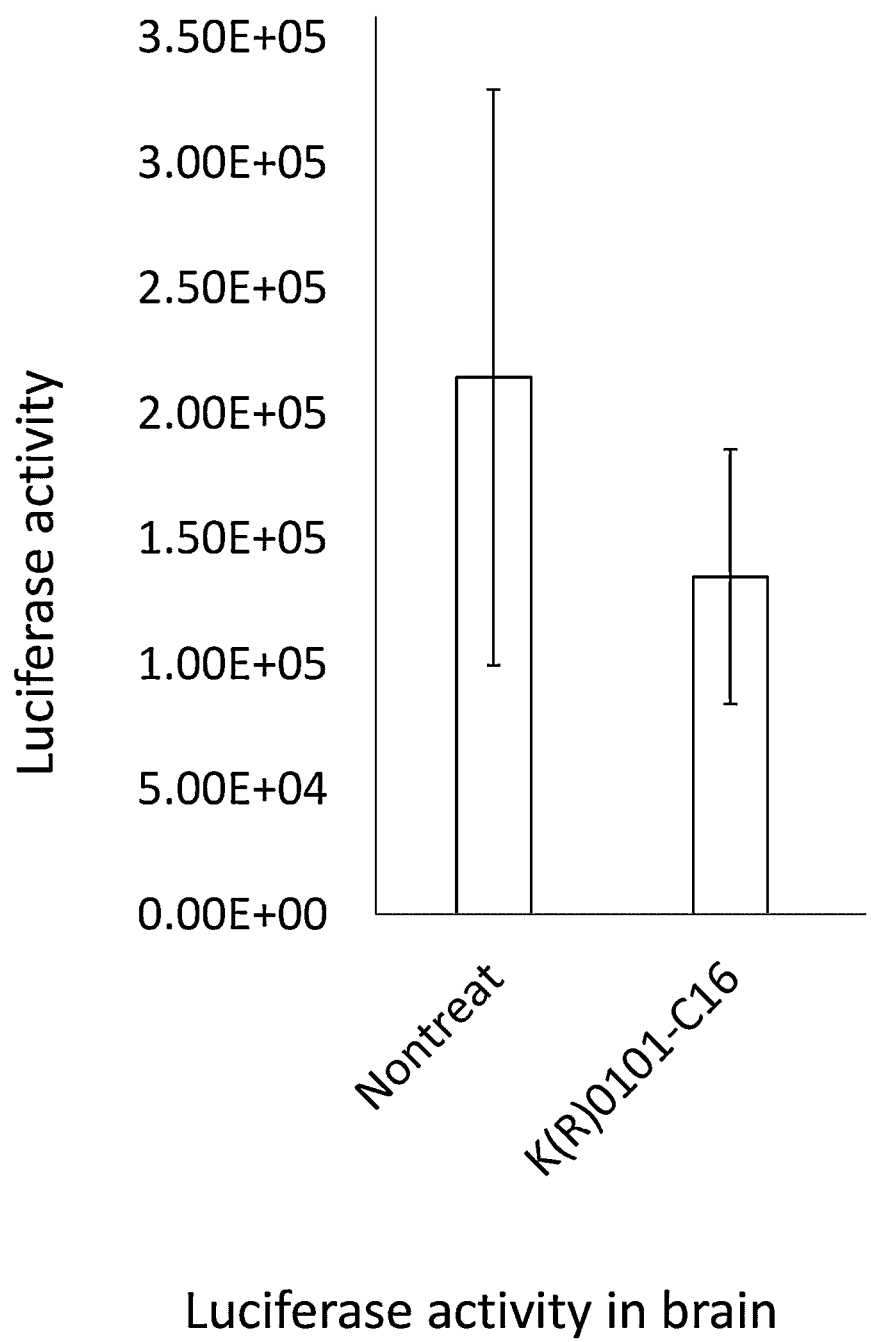

FIG. 12 is a graph showing the measurement results of the luciferase activity in the brain (inhibition of expression of firefly luciferase gene) shown in the photograph of FIG. 10.

DESCRIPTION OF EMBODIMENTS

Unless otherwise specified, the terms used in the present specification mean what is generally meant by them in the art.

1. ssNc Molecule

The single-stranded nucleic acid molecule of the present invention is, as mentioned above, a single-stranded nucleic acid molecule for inhibiting expression of a target gene having a delivery function, and is characterized in that it comprises, from the 5'-side to the 3'-side, a 5'-side region (Xc), a linker region (Lx), an inner region (Z), a linker region (Ly) and a 3'-side region (Yc) in this order, wherein the aforementioned inner region (Z) is constituted by linkage of an inner 5'-side region (X) and an inner 3'-side region (Y), the aforementioned 5'-side region (Xc) is complementary to the aforementioned inner 5'-side region (X), the aforementioned 3'-side region (Yc) is complementary to the aforementioned inner 3'-side region (Y), at least one of the aforementioned inner region (Z), the aforementioned 5'-side region (Xc) and the aforementioned 3'-side region (Yc) comprises an expression inhibitory sequence that inhibits expression of a target gene, and at least one selected from the group consisting of the 5'-terminus, the 3'-terminus, the aforementioned linker region (Lx) and the aforementioned linker region (Ly) is bound to a bio-related substance.

In the present invention, "inhibition of expression of a target gene" means, for example, inhibiting the expression of the aforementioned target gene. The mechanism by which the aforementioned inhibition is achieved is not particularly limited, and may be, for example, downregulation or silencing. The aforementioned inhibition of the expression of the target gene can be verified by, for example, a decrease in the amount of a transcription product derived from the target gene; a decrease in the activity of the aforementioned transcription product; a decrease in the amount of a translation product generated from the aforementioned target gene; a decrease in the activity of the aforementioned translation product; or the like. The aforementioned proteins may be, for example, mature proteins, precursor proteins before being subjected to processing or post-translational modification.

The single-stranded nucleic acid molecule of the present invention hereinafter also may be referred to as the "ssNc molecule" of the present invention. The ssNc molecule of the present invention can be used to inhibit, for example, the expression of a target gene in vivo or in vitro and can also be referred to as an "ssNc molecule for inhibiting the expression of a target gene" or "inhibitor of the expression of a target gene". Furthermore, the ssNc molecule of the present invention can inhibit the expression of the aforementioned target gene by, for example, RNA interference, and it can also be referred to as an "ssNc molecule for RNA interference", "molecule for inducing RNA interference", "RNA interference agent" or "RNA interference-inducing agent". The ssNc molecule of the present invention can also inhibit, for example, a side effect such as interferon induction.

In the ssNc molecule of the present invention, the 5' end and the 3' end are not linked to each other. Thus, the ssNc molecule of the present invention can also be referred to as a "linear single-stranded nucleic acid molecule". In the ssNc molecule of the present invention, for example, the aforementioned inner 5'-region (X) and the aforementioned inner 3'-region (Y) are directly linked at the aforementioned inner region (Z).

In the ssNc molecule of the present invention, the aforementioned 5'-side region (Xc) is complementary to the aforementioned inner 5'-side region (X) and the aforementioned 3'-side region (Yc) is complementary to the aforementioned inner 3'-side region (Y). Thus, on the 5'-side, a double strand can be formed by fold-back of the aforementioned region (Xc) toward the region (X) and self-annealing of the aforementioned regions (Xc) and (X) and, on the 3'-side, a double strand can be formed by fold-back of the aforementioned region (Yc) toward the region (Y) and self-annealing of the aforementioned regions (Yc) and (Y).

In the ssNc molecule of the present invention, the aforementioned expression inhibitory sequence is a sequence that exhibits, for example, an activity of inhibiting the aforementioned expression of a target gene when the ssNc molecule of the present invention is introduced into a cell in vivo or in vitro. The aforementioned expression inhibitory sequence is not particularly limited, and can be set as appropriate depending on the kind of a target gene. As the aforementioned expression inhibitory sequence, for example, a sequence involved in RNA interference caused by siRNA can be used as appropriate. Generally, RNA interference is a phenomenon in which a long double-stranded RNA (dsRNA) is cleaved in a cell by Dicer to produce a double-stranded RNA (siRNA: small interfering RNA) composed of about 19 to 21 base pairs and having a protruding 3' end, and one of the single-stranded RNAs binds to a target mRNA to degrade the aforementioned mRNA, whereby the translation of the mRNA is inhibited. As the sequence of the single-stranded RNA of the aforementioned siRNA binding to the aforementioned target mRNA, for example, various kinds of sequences for various kinds of target genes have been reported. In the present invention, for example, the sequence of the single-stranded RNA of the aforementioned siRNA can be used as the aforementioned expression inhibitory sequence. In the present invention, not only the sequences of the single-stranded RNA of the siRNA known at the time of the filing of the present application but also sequences that would be identified in the future can be used, for example, as the aforementioned expression inhibitory sequence.

The aforementioned expression inhibitory sequence is, for example, preferably at least 90% complementary, more preferably 95% complementary, still more preferably 98% complementary, and particularly preferably 100% complementary to a predetermined region of the aforementioned target gene. When such complementarity is satisfied, for example, an off-target effect can be reduced sufficiently.

It is speculated that the aforementioned inhibition of the expression of a target gene by the ssNc molecule of the present invention is achieved, for example, by RNA interference or a phenomenon similar to RNA interference (RNA interference-like phenomenon), which is caused by a structure configuring the aforementioned expression inhibitory sequence, in at least one of the aforementioned inner region (Z), the aforementioned 5'-side region (Xc) and the aforementioned 3'-side region (Yc). It should be noted, however, that the present invention is by no means limited by this mechanism. Unlike the so-called siRNA, for example, the ssNc molecule of the present invention is not introduced to a cell or the like in the form of dsRNA composed of two-chains single-stranded RNAs, and it is not always necessary to cleave out the aforementioned expression inhibitory sequence in the cell. Thus, it can be said, for example, that the ssNc molecule of the present invention exhibits an RNA interference-like function.

In the ssNc molecule of the present invention, the aforementioned expression inhibitory sequence is included in at least one of the aforementioned inner region (Z), the aforementioned 5'-side region (Xc) and the aforementioned 3'-side region (Yc), as described above. The ssNc molecule of the present invention may include, for example, one expression inhibitory sequence or two or more expression inhibitory sequences mentioned above.

In the latter case, the ssNc molecule of the present invention may include, for example: two or more identical expression inhibitory sequences for the same target gene; two or more different expression inhibitory sequences for the same target gene; or two or more different expression inhibitory sequences for different target genes. When the ssNc molecule of the present invention includes two or more expression inhibitory sequences mentioned above, the positions of the respective expression inhibitory sequences are not particularly limited, and they may be in one region or different regions selected from the aforementioned inner region (Z), the aforementioned 5'-side region (Xc) and the aforementioned 3'-side region (Yc). When the ssNc molecule of the present invention includes two or more expression inhibitory sequences mentioned above for different target genes, for example, the ssNc molecule of the present invention can inhibit the expressions of two or more kinds of different target genes.

As described above, the aforementioned inner region (Z) is composed of, the aforementioned inner 5' region (X) and the aforementioned inner 3' region (Y) that are linked to each other. For example, the aforementioned regions (X) and (Y) are linked directly to each other with no intervening sequence therebetween. The aforementioned inner region (Z) is represented as being "composed of the aforementioned inner 5'-side region (X) and the aforementioned inner 3'-side region (Y) that are linked to each other" merely to indicate the sequence context between the aforementioned 5'-side region (Xc) and the aforementioned 3'-side region (Yc). This definition does not intend to limit that, for example, in the use of the aforementioned ssNc molecule, the aforementioned 5'-side region (Xc) and the aforementioned 3'-side region (Yc) in the aforementioned inner region (Z) are discrete independent regions. That is, for example, when the aforementioned expression inhibitory sequence is included in the aforementioned inner region (Z), the aforementioned expression inhibitory sequence may be arranged to extend across the aforementioned regions (X) and (Y) in the aforementioned inner region (Z).

In the ssNc molecule of the present invention, the aforementioned 5'-side region (Xc) is complementary to the aforementioned inner 5'-side region (X). It is only necessary that the aforementioned region (Xc) has a sequence complementary to the entire region or part of the aforementioned region (X). Specifically, for example, preferably, the aforementioned region (Xc) includes or is composed of a sequence complementary to the entire region or part of the aforementioned region (X). The aforementioned region (Xc) may be, for example, perfectly complementary to the entire region or part of the aforementioned region (X), or one or a few bases in the aforementioned region (Xc) may be noncomplementary to the same. Preferably, the aforementioned region (Xc) is perfectly complementary to the same. In the ssNc molecule of the present invention, the aforementioned 3'-side region (Yc) is complementary to the aforementioned inner 3'-side region (Y). It is only necessary that the aforementioned region (Yc) has a sequence complementary to the entire region or part of the aforementioned region (Y). Specifically, for example, preferably, the aforementioned region (Yc) includes or is composed of a sequence complementary to the entire region or part of the aforementioned region (Y). The aforementioned region (Yc) may be, for example, perfectly complementary to the entire region or part of the aforementioned region (Y), or one or a few bases in the aforementioned region (Yc) may be noncomplementary to the same. Preferably, the aforementioned region (Yc) is perfectly complementary to the same. The aforementioned expression "one or a few bases" means, for example, 1 to 3 bases, preferably 1 base or 2 bases.

The ssNc molecule of the present invention may be configured so that it has a linker region (Lx) between the aforementioned 5'-side region (Xc) and inner 5'-side region (X) and the aforementioned regions (Xc) and (X) are linked via the aforementioned linker region (Lx).

The ssNc molecule of the present invention has a linker region (Ly) between the aforementioned 3'-side region (Yc) and inner 3'-side region (Y), and the aforementioned regions (Yc) and (Y) are linked via the aforementioned linker region (Ly).

The aforementioned linker region (Lx) and the aforementioned linker region (Ly) each preferably have a structure free of self-annealing inside the very region.

In the ssNc molecule of the present invention, the aforementioned bio-related substance is a substance that shows affinity for living organisms and can also be referred to as a biocompatible substance. The aforementioned bio-related substance is, for example, a substance contained in a component derived from a living organism or a substance having a structure the same as or similar to that of the component. The aforementioned bio-related substance is not particularly limited as long as it shows affinity for living organisms and, for example, various functional substances such as vitamin, hormone and the like can be mentioned. More specifically, for example, it is as follows.

For example, the first form of the aforementioned bio-related substance is lipid. The ssNc molecule of the present invention can improve, for example, introduction efficiency into a cell and/or resistance to enzymatic degradation by having a lipid. This is assumed to be attributable to, for example, the following mechanism. That is, the ssNc molecule of the present invention has improved permeability of cellular membrane and improved resistance to enzymatic degradation by forming a micell structure as a whole with the aforementioned lipid region and other nucleic acid regions. In addition, the ssNc molecule of the present invention is understood to have more improved mobility in living organisms since the aforementioned lipid region and other nucleic acid regions form an exosome-like complex as a whole. The present invention is not limited to such mechanisms.

Specific examples of the aforementioned lipid include simple lipid, complex lipid, derived lipid, liposoluble vitamin and the like. Examples of the aforementioned simple lipid include single-chain lipid which is an ester of fatty acid and alcohol. Examples of the aforementioned complex lipid include a double-chain phospholipid, glycolipid and the like. Examples of the aforementioned derived lipid include fatty acids such as saturated fatty acid, unsaturated fatty acid and the like, steroids such as cholesterol, steroid hormone and the like, and the like. Examples of the aforementioned liposoluble vitamin include retinol, tocopherol, calciferol and the like. Besides these, examples of the aforementioned lipid include fats and oils, hydrocarbons such as squalene and the like, higher alcohol and the like.

The aforementioned single-chain lipid is represented by, for example, RCOO—. The aforementioned double-chain lipid is represented by, for example, the following formula. R is, for example, saturated fatty acids such as palmitic acid, stearic acid, myristic acid and the like, unsaturated fatty acids such as oleic acid and the like, and the like.

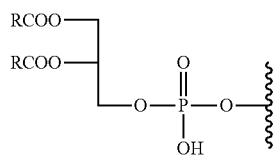

The second form of the aforementioned bio-related substance is, for example, peptide. The ssNc molecule of the present invention having, for example, the aforementioned peptide can improve introduction efficiency into a cell and/or resistance to enzymatic degradation.

The aforementioned peptide is not particularly limited and examples include a protein bindable to a membrane protein of a target cell or a peptide thereof; a protein selectively incorporated into the target site or a peptide thereof, a biological molecule acting on a particular receptor or a peptide thereof, an antibody protein reacting with an antigen expressed on a cellular surface or a peptide thereof and the like. The aforementioned protein bindable to a membrane protein is, for example, a membrane-permeable protein and the like, and the peptide thereof is, for example, arginine peptide and the like. The aforementioned peptide of the antibody protein is, for example, Fab domain and the like.

Other forms of the aforementioned bio-related substance include, for example, polyethylene glycol (PEG), polyamine, fluorescence molecule, biotin, intercalator molecule, sugar, water-soluble vitamin, metal chelating agent, cross-linking agent and the like.

In the ssNc molecule of the present invention, the number of the aforementioned bio-related substance is not particularly limited and it is, for example, 1-4, preferably, 1-3, more preferably, 1 or 2. The binding sites of the aforementioned bio-related substance are, as mentioned above, the 5'-terminus, 3'-terminus, the aforementioned linker region (Lx) and/or the aforementioned linker region (Ly) of the aforementioned nucleic acid molecule.

In the ssNc molecule of the present invention, the aforementioned bio-related substance may be, for example, directly or indirectly bonded to the aforementioned nucleic acid molecule, preferably indirectly. When indirectly bonded, for example, binding via a binding linker is preferable. The structure of the aforementioned binding linker is not particularly limited and, for example, the structure of the following formula can be mentioned. In the following formula, n is a positive integer, Y is, for example, NH, S, O, CO and the like. In the ssNc molecule of the present invention, when the aforementioned bio-related substance has an amino acid such as cysteine and the like, for example, the aforementioned bio-related substance may be bonded to the aforementioned nucleic acid molecule via a disulfide bond.

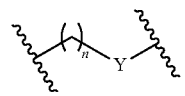

One embodiment of the nucleic acid structure of the ssNc molecule of the present invention is shown by the schematic view of FIG. 1. FIG. 1A is a schematic view showing the order of the respective regions from the 5' side to the 3' side in the aforementioned ssNc molecule. FIG. 1B is a schematic view showing the state where double strands are formed in the aforementioned ssNc molecule. As shown in FIG. 1B, in the aforementioned ssNc molecule, the aforementioned 5'-side region (Xc) is folded back, double strands are formed between the aforementioned 5'-side region (Xc) and the aforementioned inner 5'-side region (X), the aforementioned 3'-side region (Yc) is folded back, double strands are formed between the aforementioned 3'-side region (Yc) and the aforementioned inner 3'-side region (Y), and the aforementioned Lx region and the aforementioned Ly region each have a loop structure. The schematic views shown in FIG. 1 merely illustrates the order in which the respective regions are linked and the positional relationship of the respective regions forming the double strand, and they do not limit, for example, the lengths of the respective regions, and the like.

In the ssNc molecule of the present invention, the aforementioned bio-related substance may be bonded to, as mentioned above, for example, any of an unbound terminal of the aforementioned 5'-side region (Xc), an unbound terminal of the aforementioned 3'-side region (Yc), linker region (Lx), and linker region (Ly) in FIG. 1.

In the ssNc molecule of the present invention, the base number of the aforementioned 5'-side region (Xc), the aforementioned inner 5'-side region (X), the aforementioned inner 3'-side region (Y) and the aforementioned 3'-side region (Yc) is not particularly limited and it is, for example, as described below. In the present invention, "the number of bases" means the "length", for example, and it can also be referred to as the "base length".

As described above, for example, the aforementioned 5'-side region (Xc) may be complementary to the entire region of the aforementioned inner 5'-side region (X). In this case, it is preferable that, for example, the aforementioned region (Xc) has the same base length as the aforementioned region (X), and is composed of a base sequence complementary to the entire region of from the 5'-terminus to the 3'-terminus of the aforementioned region (X). It is more preferable that the aforementioned region (Xc) has the same base length as the aforementioned region (X) and all the bases in the aforementioned region (Xc) are complementary to all the bases in the aforementioned region (X), i.e., for example, preferably, the region (Xc) is perfectly complementary to the region (X). It is to be noted, however, that the configuration of the region (Xc) is not limited thereto, and one or a few bases in the region (Xc) may be noncomplementary to the corresponding bases in the region (X), for example, as described above.

Furthermore, as described above, the aforementioned 5'-side region (Xc) may be complementary to, for example, a part of the aforementioned inner 5'-side region (X). In this case, it is preferable that, for example, the aforementioned region (Xc) has the same base length as the part of the aforementioned region (X), i.e., the aforementioned region (Xc) is composed of a base sequence whose base length is shorter than the base length of the aforementioned region (X) by one or more bases. It is more preferable that the aforementioned region (Xc) has the same base length as the part of the aforementioned region (X) and all the bases in the aforementioned region (Xc) are complementary to all the bases in the part of the aforementioned region (X), i.e., for example, preferably, the region (Xc) is perfectly complementary to the part of the region (X). The part of the aforementioned region (X) is preferably a region (segment) having a base sequence composed of, for example, successive bases starting from the base at the 5' end (the 1st base) in the aforementioned region (X).

As described above, the aforementioned 3'-side region (Yc) may be complementary to, for example, the entire region of the aforementioned inner 3'-side region (Y). In this case, it is preferable that, for example, the aforementioned region (Yc) has the same base length as the aforementioned region (Y), and is composed of a base sequence complementary to the entire region of from the 5'-terminus to the 3'-terminus of the aforementioned region (Y). It is more preferable that the aforementioned region (Yc) has the same base length as the aforementioned region (Y) and all the bases in the aforementioned region (Yc) are complementary to all the bases in the aforementioned region (Y), i.e., for example, preferably, the region (Yc) is perfectly complementary to the region (Y). It is to be noted, however, that the configuration of the region (Yc) is not limited thereto, and one or a few bases in the region (Yc) may be noncomplementary to the corresponding bases in the region (Y), for example, as described above.

Furthermore, as described above, the aforementioned 3'-side region (Yc) may be complementary to, for example, a part of the aforementioned inner 3'-side region (Y). In this case, it is preferable that, for example, the aforementioned region (Yc) has the same base length as the part of the aforementioned region (Y), i.e., the aforementioned region (Yc) is composed of a base sequence whose base length is shorter than the base length of the aforementioned region (Y) by one or more bases. It is more preferable that the aforementioned region (Yc) has the same base length as the part of the aforementioned region (Y) and all the bases in the aforementioned region (Yc) are complementary to all the bases in the part of the aforementioned region (Y), i.e., for example, preferably, the region (Yc) is perfectly complementary to the part of the region (Y). The part of the aforementioned region (Y) is preferably a region (segment) having a base sequence composed of, for example, successive bases starting from the base at the 3' end (the 1st base) in the aforementioned region (Y).

In the ssNc molecule of the present invention, the relationship of the number of bases (Z) in the aforementioned inner region (Z) with the number of bases (X) in the aforementioned inner 5'-side region (X) and the number of bases (Y) in the aforementioned inner 3'-side region (Y) and the relationship of the number of bases (Z) in the aforementioned inner region (Z) with the number of bases (X) in the aforementioned inner 5'-side region (X) and the number of bases (Xc) in the aforementioned 5'-side region (Xc) satisfy, for example, the conditions of the following expressions (1) and (2).

$$Z = X + Y \tag{1}$$

$$Z \geq Xc + Yc \tag{2}$$

In the ssNc molecule of the present invention, the relationship between the number of bases (X) in the aforementioned inner 5'-side region (X) and the number of bases (Y) in the aforementioned inner 3'-side region (Y) is not particularly limited, and may satisfy, for example, any of the conditions of the following expressions:

$$X = Y \tag{19}$$

$$X < Y \tag{20}$$

$$X > Y \tag{21}.$$

In the ssNc molecule of the present invention, the relationship between the number of bases (X) in the aforementioned inner 5'-side region (X) and the number of bases (Xc) in the aforementioned 5'-side region (Xc), and the relationship between the number of bases (Y) in the aforementioned inner 3'-side region (Y) and the number of bases (Yc) in the aforementioned 3'-side region (Yc) satisfy, for example, any of the following conditions (a) to (d):

(a) Conditions of the following expressions (3) and (4) are satisfied.

$$X > Xc \tag{3}$$

$$Y = Yc \tag{4}$$

(b) Conditions of the following expressions (5) and (6) are satisfied.

$$X = Xc \tag{5}$$

$$Y > Yc \tag{6}$$

(c) Conditions of the following expressions (7) and (8) are satisfied.

$$X > Xc \tag{7}$$

$$Y > Yc \tag{8}$$

(d) Conditions of the following expressions (9) and (10) are satisfied.

$$X=Xc \quad (9)$$

$$Y=Yc \quad (10)$$

In the above-described conditions (a) to (d), for example, the difference between the number of bases (X) in the aforementioned inner 5'-side region (X) and the number of bases (Xc) in the aforementioned 5'-side region (Xc), and the difference between the number of bases (Y) in the aforementioned inner 3'-side region (Y) and the number of bases (Yc) in the aforementioned 3'-side region (Yc) preferably satisfy the following conditions.

(a) Conditions of the following expressions (11) and (12) are satisfied.

$$X\text{-}Xc=1 \text{ to } 10, \text{ preferably } 1, 2, 3, \text{ or } 4, \text{ more preferably } 1, 2, \text{ or } 3 \quad (11)$$

$$Y\text{-}Yc=0 \quad (12)$$

(b) Conditions of the following expressions (13) and (14) are satisfied.

$$X\text{-}Xc=0 \quad (13)$$

$$Y\text{-}Yc=1 \text{ to } 10, \text{ preferably } 1, 2, 3, \text{ or } 4, \text{ more preferably } 1, 2, \text{ or } 3 \quad (14)$$

(c) Conditions of the following expressions (15) and (16) are satisfied.

$$X\text{-}Xc=1 \text{ to } 10, \text{ preferably, } 1, 2, \text{ or } 3, \text{ more preferably } 1 \text{ or } 2 \quad (15)$$

$$Y\text{-}Yc=1 \text{ to } 10, \text{ preferably, } 1, 2, \text{ or } 3, \text{ more preferably } 1 \text{ or } 2 \quad (16)$$

(d) Conditions of the following expressions (17) and (18) are satisfied.

$$X\text{-}Xc=0 \quad (17)$$

$$Y\text{-}Yc=0 \quad (18)$$

Regarding the ssNc molecules satisfying the aforementioned conditions (a) to (d), examples of their structures are shown respectively in the schematic views of FIG. 2. FIG. 2 shows the ssNc molecules including the aforementioned linker regions (Lx) and (Ly). FIG. 2A shows an example of the ssNc molecule satisfying the aforementioned condition (a); FIG. 2B shows an example of the ssNc molecule satisfying the aforementioned condition (b); FIG. 2C shows an example of the ssNc molecule satisfying the aforementioned condition (c); and FIG. 2D shows an example of the ssNc molecule satisfying the aforementioned condition (d). In FIG. 2, dotted lines indicate a state where double strands are formed by self-annealing. The ssNc molecules shown in FIG. 2 are all directed to examples where the relationship between the number of bases (X) in the aforementioned inner 5'-side region (X) and the number of bases (Y) in the aforementioned inner 3'-side region (Y) satisfy "X<Y" of the aforementioned expression (20). It is to be noted, however, that the relationship is not limited thereto, and "X=Y" of the aforementioned expression (19) or "X>Y" of the aforementioned expression (21) may be satisfied as described above. The schematic views shown in FIG. 2 merely illustrate the relationship between the aforementioned inner 5'-side region (X) and the aforementioned 5'-side region (Xc) and the relationship between the aforementioned inner 3'-side region (Y) and the aforementioned 3'-side region (Yc), and they do not limit, for example, the length and shape and the like of each region, and the presence or absence of the linker region (Lx) and linker region (Ly).

The ssNc molecules of the above-mentioned (a) to (c) are configurations having base(s) that can be not aligned with both the aforementioned 5'-side region (Xc) and the aforementioned 3'-side region (Yc) in the aforementioned inner region (Z) since, for example, the aforementioned 5'-side region (Xc) and the aforementioned inner 5'-side region (X), and the aforementioned 3'-side region (Yc) and the aforementioned inner 3'-side region (Y) each form a double strand. They may also be said configurations having base(s) not forming a double strand. In the aforementioned inner region (Z), the aforementioned base that can be not aligned (also referred to as a base that does not form a double strand) is hereinafter to be referred to as an "unpaired base". In FIG. 2, the region of the aforementioned unpaired base is shown by "F". The number of the bases in the aforementioned region (F) is not particularly limited. The number of the bases (F) in the aforementioned region (F) is, for example, the number of the bases of "X–Xc" for the ssNc molecule of the aforementioned (a); the number of the bases of "Y–Yc" for the ssNc molecule of the above-mentioned (b); and the total of the number of the bases of "X-Xc" and the number of the bases of "Y–Yc" for the ssNc molecule of the aforementioned (c).

On the other hand, the ssNc molecule satisfying the aforementioned condition (d) is configured so that, for example, the entire region of the aforementioned inner region (Z) is aligned with the aforementioned 5'-side regions (Xc) and the aforementioned 3'-side region (Yc), in other words, the entire region of the aforementioned inner region (Z) forms a double strand. In the ssNc molecule satisfying the aforementioned condition (d), the 5° end of the aforementioned 5'-side region (Xc) and 3' end of the aforementioned 3'-side region (Yc) are not linked to each other.

While the length of each region of the ssNc molecule of the present invention is shown below, the present invention is not limited thereto. In the present invention, for example, the numerical range of the base number discloses all positive integers that fall within the range and, for example, "1-4 bases" means all of "1, 2, 3, 4 bases" (hereinafter the same).

The total number of the bases in the aforementioned 5'-side region (Xc), the bases in the aforementioned 3'-side region (Yc), and the aforementioned unpaired bases (F) in the aforementioned inner region (Z) is, for example, equal to the number of the bases in the aforementioned inner region (Z). Thus, the length of the aforementioned 5'-side region (Xc) and the length of the aforementioned 3'-side region (Yc) can be determined as appropriate depending on, for example, the length of the aforementioned inner region (Z), the number of the aforementioned unpaired bases (F), and the positions of the unpaired bases.

The number of the bases in the aforementioned inner region (Z) is, for example, 19 or more. The lower limit of the number of the bases is, for example, 19, preferably 20, and more preferably 21. The upper limit of the number of the aforementioned bases is, for example, 50, preferably 40, and more preferably 30. A specific example of the number of the bases in the aforementioned inner region (Z) is 19, 20, 21, 22, 23, 24, 25, 26, 27, 28, 29, or 30.

When the aforementioned inner region (Z) includes the aforementioned expression inhibitory sequence, the aforementioned inner region (Z) may be, for example, a region composed of the aforementioned expression inhibitory sequence only or a region including the aforementioned expression inhibitory sequence. The number of bases of the aforementioned expression inhibitory sequence is, for example, 19 to 30, preferably 19, 20, or 21. When the aforementioned inner region (Z) includes the aforementioned expression inhibitory sequence, the aforementioned expression inhibitory sequence further may have an additional sequence on its 5' side and/or 3' side. The number of bases in the aforementioned additional sequence is, for example, 1 to 31, preferably 1 to 21, more preferably 1 to 11, and still more preferably 1 to 7.

The number of bases in the aforementioned 5'-side region (Xc) is, for example, 1 to 29, preferably 1 to 11, more preferably 1 to 7, still more preferably 1 to 4, and particularly preferably 1, 2, or 3. When the aforementioned inner region (Z) or the aforementioned 3'-side region (Yc) includes the aforementioned expression inhibitory sequence, for example, the number of bases as described above is preferable. A specific example is as follows: when the number of bases in the aforementioned inner region (Z) is 19 to 30 (e.g., 19), the number of bases in the aforementioned 5'-side region (Xc) is, for example, 1 to 11, preferably 1 to 7, more preferably 1 to 4, and still more preferably 1, 2, or 3.

When the aforementioned 5'-side region (Xc) includes the aforementioned expression inhibitory sequence, the aforementioned 5'-side region (Xc) may be, for example, a region composed of the aforementioned expression inhibitory sequence only or a region including the aforementioned expression inhibitory sequence. For example, the length of the aforementioned expression inhibitory sequence is as described above. When the aforementioned 5'-side region (Xc) includes the aforementioned expression inhibitory sequence, the aforementioned expression inhibitory sequence further may have an additional sequence on its 5' side and/or 3' side. The number of bases in the aforementioned additional sequence is, for example, 1 to 11, preferably 1 to 7.

The number of bases in the aforementioned 3'-side region (Yc) is, for example, 1 to 29, preferably 1 to 11, more preferably 1 to 7, still more preferably 1 to 4, and particularly preferably 1, 2, or 3. When the aforementioned inner region (Z) or the aforementioned 5'-side region (Xc) includes the aforementioned expression inhibitory sequence, for example, the number of bases as described above is preferable. A specific example is as follows: when the number of bases in the aforementioned inner region (Z) is 19 to 30 (e.g., 19), the number of bases in the aforementioned 3'-side region (Yc) is, for example, 1 to 11, preferably 1 to 7, more preferably 1 to 4, and still more preferably 1, 2, or 3.

When the aforementioned 3'-side region (Yc) includes the aforementioned expression inhibitory sequence, the aforementioned 3'-side region (Yc) may be, for example, a region composed of the aforementioned expression inhibitory sequence only or a region including the aforementioned expression inhibitory sequence. The length of the aforementioned expression inhibitory sequence is, for example, as described above. When the aforementioned 3'-side region (Yc) includes the aforementioned expression inhibitory sequence, the aforementioned expression inhibitory sequence further may have an additional sequence on its 5' side and/or 3' side. The number of bases in the aforementioned additional sequence is, for example, 1 to 11, preferably 1 to 7.

As described above, the relationship among the number of bases in the aforementioned inner region (Z), the number of bases in the aforementioned 5'-side region (Xc), and the number of bases in the aforementioned 3'-side region (Yc) can be expressed by, for example, the aforementioned expression (2): "≥Xc+Yc". Specifically, the number of bases represented by "Xc+Yc" is, for example, equal to the number of bases in the aforementioned inner region (Z), or lower than the number of bases in the aforementioned inner region (Z). In the latter case, "Z−(Xc+Yc)" is, for example, 1 to 10, preferably 1 to 4, and more preferably 1, 2, or 3. The aforementioned "Z−(Xc+Yc)" corresponds, for example, to the number of bases (F) in the aforementioned unpaired base region (F) in the aforementioned inner region (Z).

In the ssNc molecule of the present invention, the lengths of the aforementioned linker regions (Lx) and (Ly) are not particularly limited. The aforementioned linker region (Lx) preferably has, for example, a length permitting the aforementioned inner 5'-side region (X) and the aforementioned 5'-side region (Xc) to form a double strand, and the aforementioned linker region (Ly) preferably has, for example, a length permitting the aforementioned inner 3'-side region (Y) and the aforementioned 3'-side region (Yc) to form a double strand. When the constitutional units of the aforementioned linker region (Lx) and the aforementioned linker region (Ly) include a base(s), the base number of the aforementioned linker region (Lx) and the aforementioned linker region (Ly) may be the same or different, and also, the base sequences thereof may be the same or different. As for the base number of the aforementioned linker region (Lx) and the aforementioned linker region (Ly), the lower limit of the number of bases is, for example, 1, preferably 2, and more preferably 3, and the upper limit of the same is, for example, 100, preferably 80, and more preferably 50. The number of bases in each of the aforementioned linker regions is specifically 1 to 50, 1 to 30, 1 to 20, 1 to 10, 1 to 7, or 1 to 4, for example, but it is not limited to these examples.

The full length of the ssNc molecule of the present invention is not particularly limited. In the ssNc molecule of the present invention, the lower limit of the total number of bases (the number of bases in the full length), is, for example, 38, preferably 42, more preferably 50, still more preferably 51, and particularly preferably 52, and the upper limit of the same is, for example, 300, preferably 200, more preferably 150, still more preferably 100, and particularly preferably 80. In the ssNc molecule of the present invention, the lower limit of the total number of bases excluding those in the aforementioned linker regions (Lx) and (Ly) is, for example, 38, preferably 42, more preferably 50, still more preferably 51, and particularly preferably 52, and the upper limit of the same is, for example, 300, preferably 200, more preferably 150, still more preferably 100, and particularly preferably 80.

In the ssNc molecule of the present invention, the constitutional units are not particularly limited. Examples thereof include nucleotide residues. Examples of the aforementioned nucleotide residues include a ribonucleotide residue and a deoxyribonucleotide residue. The aforementioned nucleotide residue may be, for example, the one that is not modified (unmodified nucleotide residue) or the one that has been modified (modified nucleotide residue). By configuring the ssNc molecule of the present invention to include the aforementioned modified nucleotide residue, for example, the resistance of the ssNc molecule to nuclease can be improved, thereby allowing the stability of the ssNc molecule to be improved. Furthermore, the ssNc molecule of the present invention further may include, for example, a non-nucleotide residue in addition to the aforementioned nucleotide residue. The detail of the aforementioned nucleotide residue and the aforementioned non-nucleotide residue is described later.

In the ssNc molecule of the present invention, the constitutional unit of each of the aforementioned inner region (Z), the aforementioned 5'-side region (Xc) and the aforementioned 3'-side region (Yc) is preferably the aforementioned nucleotide residue. Each of the aforementioned regions is composed of, for example, any of the following residues (1) to (3):
(1) an unmodified nucleotide residue(s)
(2) a modified nucleotide residue(s)
(3) an unmodified nucleotide residue(s) and a modified nucleotide residue(s).

In the ssNc molecule of the present invention, the constitutional units of the aforementioned linker regions (Lx) and (Ly) are not particularly limited, and examples thereof include the aforementioned nucleotide residues and the aforementioned non-nucleotide residues. Each of the aforementioned linker regions may be composed of, for example, the aforementioned nucleotide residue(s) only, the aforementioned non-nucleotide residue(s) only, or both the aforementioned nucleotide residue(s) and the aforementioned non-nucleotide residue(s). Each of the aforementioned linker regions is composed of, for example, any of the following residues (1) to (7):
(1) an unmodified nucleotide residue(s)
(2) a modified nucleotide residue(s)
(3) an unmodified nucleotide residue(s) and a modified nucleotide residue(s)
(4) a non-nucleotide residue(s)
(5) a non-nucleotide residue(s) and an unmodified nucleotide residue(s)
(6) a non-nucleotide residue(s) and a modified nucleotide residue(s)
(7) a non-nucleotide residue(s), an unmodified nucleotide residue(s), and a modified nucleotide residue(s).

When the ssNc molecule of the present invention has both the aforementioned linker region (Lx) and the aforementioned linker region (Ly), for example, the both constitutional units may be the same or different. Specific examples thereof include a form wherein the constitutional unit of the both linker regions is the aforementioned nucleotide residue, a form wherein the constitutional unit of the both linker regions is the aforementioned non-nucleotide residue, a form wherein the constitutional unit of one region is the aforementioned nucleotide residue and the constitutional unit of the other linker region is a non-nucleotide residue and the like.

Examples of the ssNc molecule of the present invention include molecules composed of the aforementioned nucleotide residues only; and molecules including the aforementioned non-nucleotide residue(s) in addition to the aforementioned nucleotide residues. In the ssNc molecule of the present invention, for example, the aforementioned nucleotide residues may be the aforementioned unmodified nucleotide residues only; the aforementioned modified nucleotide residues only; or both the aforementioned unmodified nucleotide residue(s) and the aforementioned modified nucleotide residue(s), as described above. When the aforementioned ssNc molecule includes both the aforementioned unmodified nucleotide residue(s) and the aforementioned modified nucleotide residue(s), the number of the aforementioned modified nucleotide residue(s) is not particularly limited, and is, for example, "one to several", specifically, for example, 1 to 5, preferably 1 to 4, more preferably 1 to 3, and most preferably 1 or 2. When the ssNc molecule of the present invention include the aforementioned non-nucleotide residue(s), the number of the aforementioned non-nucleotide residue(s) is not particularly limited, and is, for example, "one to several", specifically, for example, 1 to 8, 1 to 6, 1 to 4, 1, 2 or 3.

In the ssNc molecule of the present invention, for example, the aforementioned nucleotide residue is preferably a ribonucleotide residue. In this case, for example, the ssNc molecule of the present invention also is referred to as an "RNA molecule" or "ssRNA molecule". Examples of the aforementioned ssRNA molecule include molecules composed of the aforementioned ribonucleotide residues only; and a molecule including the aforementioned non-nucleotide residue(s) in addition to the aforementioned ribonucleotide residues. As described above, as the aforementioned ribonucleotide residues, for example, the aforementioned ssRNA molecule may include: the aforementioned unmodified ribonucleotide residues only; the aforementioned modified ribonucleotide residues only; or both the aforementioned unmodified ribonucleotide residue(s) and the aforementioned modified ribonucleotide residue(s).

When the aforementioned ssRNA molecule includes, for example, the aforementioned modified ribonucleotide residue(s) in addition to the aforementioned unmodified ribonucleotide residues, the number of the aforementioned modified ribonucleotide residue(s) is not particularly limited, and is, for example, "one to several", specifically, for example, 1 to 5, preferably 1 to 4, more preferably 1 to 3, and most preferably 1 or 2. The aforementioned modified ribonucleotide residue as contrasted to the aforementioned unmodified ribonucleotide residue may be, for example, the aforementioned deoxyribonucleotide residue obtained by substituting a ribose residue with a deoxyribose residue. When the aforementioned ssRNA molecule includes, for example, the aforementioned deoxyribonucleotide residue(s) in addition to the aforementioned unmodified ribonucleotide residue(s), the number of the aforementioned deoxyribonucleotide residue(s) is not particularly limited, and is, for example, "one to several", specifically, for example, 1 to 5, preferably 1 to 4, more preferably 1 to 3, and most preferably 1 or 2.

The ssNc molecule of the present invention may include, for example, a labeling substance, and may be labeled with the aforementioned labeling substance. The aforementioned labeling substance is not particularly limited, and may be, for example, a fluorescent substance, a dye, an isotope, or the like. Examples of the aforementioned labeling substance include: fluorophores such as pyrene, TAMRA, fluorescein, a Cy3 dye, and a Cy5 dye. Examples of the aforementioned dye include Alexa dyes such as Alexa 488. Examples of the aforementioned isotope include stable isotopes and radio-isotopes. Among them, stable isotopes are preferable. For example, the aforementioned stable isotopes have a low risk of radiation exposure and they require no dedicated facilities. Thus, stable isotopes are excellent in handleability and can contribute to cost reduction. Moreover, for example, the aforementioned stable isotope does not change the physical properties of a compound labeled therewith and thus has an excellent property as a tracer. The aforementioned stable isotope is not particularly limited, and examples thereof include $^{2}H$, $^{13}C$, $^{15}N$, $^{17}O$, $^{18}O$, $^{33}S$, $^{34}S$, and, $^{36}S$.

As described above, the ssNc molecule of the present invention can inhibit the aforementioned expression of a target gene. Thus, the ssNc molecule of the present invention can be used, for example, as a therapeutic agent for treating a disease caused by a gene. When the ssNc molecule of the present invention includes, for example, as the aforementioned expression inhibitory sequence, a sequence that inhibits expression of a gene causing the aforementioned disease, for example, it is possible to treat the aforementioned disease by inhibiting the expression of the aforementioned target gene. In the present invention, the term "treatment" encompasses: prevention of the aforementioned diseases; improvement of the diseases; and improvement in prognosis, for example, and it can mean any of them.

The method of using the ssNc molecule of the present invention is not particularly limited. For example, the aforementioned ssNc molecule may be administered to a subject having the aforementioned target gene.

Examples of the aforementioned subject to which the ssNc molecule of the present invention is administered include cells, tissues, organs and the like. Examples of the aforementioned subject also include humans, nonhuman animals and the like such as nonhuman mammals, i.e., mammals excluding humans. The aforementioned administration may be performed, for example, in vivo or in vitro. The aforementioned cells are not particularly limited, and examples thereof include: various cultured cells such as HeLa cells, 293 cells, NIH3T3 cells, and COS cells; stem cells such as ES cells and hematopoietic stem cells; and cells isolated from living organisms, such as primary cultured cells.

In the present invention, the aforementioned target gene whose expression is to be inhibited is not particularly limited, and any desired gene can be set to the target gene. Furthermore, as mentioned above, the aforementioned expression inhibitory sequence may be designed as appropriate depending on the kind of the aforementioned target gene.

As to the use of the ssNc molecule of the present invention, the following description regarding the composition, the expression inhibitory method, the treatment method, and the like according to the present invention to be describe below can be referred to.

Since the ssNc molecule of the present invention can inhibit the expression of a target gene as described above, for example, it is useful as a pharmaceutical product, a diagnostic agent, an agricultural chemical, and a tool for conducting research on the agricultural chemical, medical science, life science, and the like.

2. Nucleotide Residue

The aforementioned nucleotide residue includes, for example, a sugar, a base, and a phosphate as its components. The aforementioned nucleotide residue may be, for example, a ribonucleotide residue or a deoxyribonucleotide residue, as described above. The aforementioned ribonucleotide residue has, for example, a ribose residue as the sugar; and adenine (A), guanine (G), cytosine (C), or uracil (U) as the base. The aforementioned deoxyribose residue has, for example, a deoxyribose residue as the sugar; and adenine (A), guanine (G), cytosine (C), or thymine (T) as the base.

The aforementioned nucleotide residue may be, for example, an unmodified nucleotide residue or a modified nucleotide residue. The aforementioned components of the aforementioned unmodified nucleotide residue are the same or substantially the same as, for example, the components of a naturally-occurring nucleotide residue. Preferably, the components are the same or substantially the same as the components of a nucleotide residue occurring naturally in a human body.

The aforementioned modified nucleotide residue is, for example, a nucleotide residue obtained by modifying the aforementioned unmodified nucleotide residue. For example, the aforementioned modified nucleotide residue may be such that any of the components of the aforementioned unmodified nucleotide residue is modified. In the present invention, "modification" means, for example, substitution, addition, and/or deletion of any of the aforementioned components; and substitution, addition, and/or deletion of an atom (s) and/or a functional group(s) in the aforementioned component(s). It can also be referred to as "alteration". Examples of the aforementioned modified nucleotide residue include naturally-occurring nucleotide residues and artificially-modified nucleotide residues. Regarding the aforementioned naturally-derived modified nucleotide residues, for example, Limbach et al. (Limbach et al., 1994, Summary: the modified nucleosides of RNA, Nucleic Acids Res. 22: pp. 2183 to 2196) can be referred to. The aforementioned modified nucleotide residue may be, for example, a residue of an alternative of the aforementioned nucleotide.

Examples of the modification of the aforementioned nucleotide residue include modification of a ribose-phosphate backbone (hereinafter referred to as a "ribophosphate backbone").

In the aforementioned ribophosphate backbone, for example, a ribose residue may be modified. In the aforementioned ribose residue, for example, the 2'-position carbon can be modified. Specifically, a hydroxyl group bound to, for example, the 2'-position carbon can be substituted with hydrogen or halogen such as fluoro. By substituting the hydroxyl group bound to the aforementioned 2'-position carbon with hydrogen, it is possible to substitute the ribose residue with deoxyribose. The aforementioned ribose residue can be substituted with its stereoisomer, for example, and may be substituted with, for example, an arabinose residue.

The aforementioned ribophosphate backbone may be substituted with, for example, a non-ribophosphate backbone having a non-ribose residue and/or a non-phosphate. The aforementioned non-ribophosphate backbone may be, for example, the aforementioned ribophosphate backbone modified to be uncharged. Examples of an alternative obtained by substituting the ribophosphate backbone with the aforementioned non-ribophosphate backbone in the aforementioned nucleotide include morpholino, cyclobutyl, and pyrrolidine. Other examples of the aforementioned alternative include artificial nucleic acid monomer residues. Specific examples thereof include PNA (Peptide Nucleic Acid), LNA (Locked Nucleic Acid), and ENA (2'-O,4'-C-Ethylenebridged Nucleic Acids). Among them, PNA is preferable.

In the aforementioned ribophosphate backbone, for example, a phosphate group can be modified. In the aforementioned ribophosphate backbone, a phosphate group in the closest proximity to the sugar residue is called an "α-phosphate group". The aforementioned α-phosphate group is charged negatively, and the electric charges are distributed evenly over two oxygen atoms that are not linked to the sugar residue. Among the four oxygen atoms in the aforementioned α-phosphate group, the two oxygen atoms not linked to the sugar residue in the phosphodiester linkage between the nucleotide residues hereinafter are referred to as "non-linking oxygens". On the other hand, two oxygen atoms that are linked to the sugar residue in the phosphodiester linkage between the aforementioned nucleotide residues hereinafter are referred to as "linking oxygens". For example, the aforementioned α-phosphate group is preferably modified to be uncharged, or to render the charge distribution between the aforementioned non-linking oxygens asymmetric.

In the aforementioned phosphate group, for example, the aforementioned non-linking oxygen(s) may be substituted. The aforementioned oxygen(s) can be substituted with, for example, any atom selected from S (sulfur), Se (selenium), B (boron), C (carbon), H (hydrogen), N (nitrogen), and OR (R is an alkyl group or an aryl group) and substitution with S is preferable. It is preferable that one of the non-linking oxygens is substituted with S, for example, and it is more preferable that both the aforementioned non-linking oxygens are substituted. Examples of the aforementioned modified phosphate group include phosphorothioates, phosphorodithioates, phosphoroselenates, boranophosphates, boranophosphate esters, hydrogen phosphonates, phosphoroamidates, alkyl or aryl phosphonates, and phosphotriesters. In particular, phosphorodithioate in which both of the aforementioned two non-linking oxygens are substituted with S is preferable.

In the aforementioned phosphate group, for example, the aforementioned linking oxygen(s) can be substituted. The aforementioned oxygen(s) can be substituted with, for example, any atom selected from S (sulfur), C (carbon), and N (nitrogen). Examples of the aforementioned modified phosphate group include: bridged phosphoroamidates resulting from the substitution with N; bridged phosphorothioates resulting from the substitution with S; and bridged methylenephosphonates resulting from the substitution with C. Preferably, substitution of the aforementioned linking oxygen(s) is performed in, for example, at least one of the 5' end nucleotide residue and the 3' end nucleotide residue of the ssNc molecule of the present invention. When the substitution is performed on the 5' side, substitution with C is preferable. When the substitution is performed on the 3' side, substitution with N is preferable.

The aforementioned phosphate group may be substituted with, for example, the aforementioned phosphate-free linker. The aforementioned linker may contain siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo, methyleneoxymethylimino, or the like. Preferably, the linker may contain a methylenecarbonylamino group and a methylenemethylimino group.

In the ssNc molecule of the present invention, for example, at least one of a nucleotide residue at the 3' end and a nucleotide residue at the 5' end may be modified. For example, the nucleotide residue at either one of the 3' end and the 5' end may be modified, or the nucleotide residues at both the 3' end and the 5' end may be modified. The aforementioned modification may be, for example, as described above, and it is preferable to modify a phosphate group(s) at the end(s). For example, the entire aforementioned phosphate group may be modified, or one or more atoms in the aforementioned phosphate group may be modified. In the former case, for example, the entire phosphate group may be substituted or deleted.

Modification of the aforementioned nucleotide residue(s) at the end(s) may be, for example, addition of any other molecule. Examples of the aforementioned other molecule include functional molecules such as labeling substances as described above and protecting groups. Examples of the aforementioned protecting groups include S (sulfur), Si (silicon), B (boron), and ester-containing groups. The functional molecules such as the aforementioned labeling substances can be used, for example, in the detection and the like of the ssNc molecule of the present invention.

The aforementioned other molecule may be, for example, added to the phosphate group of the aforementioned nucleotide residue or may be added to the aforementioned phosphate group or the aforementioned sugar residue via a spacer. For example, the terminus atom of the aforementioned spacer can be added to or substituted for either one of the aforementioned linking oxygens of the aforementioned phosphate group, or O, N, S, or C of the sugar residue. The binding site in the aforementioned sugar residue preferably is, for example, C at the 3'-position, C at the 5'-position, or any atom bound thereto. For example, the aforementioned spacer can also be added to or substituted for a terminus atom of the aforementioned nucleotide alternative such as PNA.

The aforementioned spacer is not particularly limited, and examples thereof include —$(CH_2)_n$—, —$(CH_2)_nN$—, —$(CH_2)_nO$—, —$(CH_2)_nS$—, $O(CH_2CH_2O)_nCH_2CH_2OH$, abasic sugars, amide, carboxy, amine, oxyamine, oxyimine, thioether, disulfide, thiourea, sulfonamide, and morpholino, and also biotin reagents and fluorescein reagents. In the aforementioned formulae, n is a positive integer, and n=3 or 6 is preferable.

Other examples of the aforementioned molecule to be added to the end include dyes, intercalating agents (e.g., acridines), crosslinking agents (e.g., psoralen, mitomycin C), porphyrins (TPPC4, texaphyrin, sapphyrin), polycyclic aromatic hydrocarbons (e.g., phenazine, dihydrophenazine), artificial endonucleases (e.g., EDTA), lipophilic carriers (e.g., cholesterol, cholic acid, adamantane acetic acid, 1-pyrenebutyric acid, dihydrotestosterone, 1,3-Bis-O (hexadecyl)glycerol, a geranyloxyhexyl group, hexadecylglycerol, borneol, menthol, 1,3-propanediol, a heptadecyl group, palmitic acid, myristic acid, O3-(oleoyl)lithocholic acid, O3-(oleoyl)cholic acid, dimethoxytrityl, or phenoxathiine), peptide complexes (e.g., Antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), and synthetic ribonucleases (e.g., imidazole, bisimidazole, histamine, imidazole clusters, acridine-imidazole complexes, $Eu^{3+}$ complexes of tetraazamacrocycles).

In the ssNc molecule of the present invention, for example, the aforementioned 5' end may be modified with a phosphate group or a phosphate group analog. Examples of the aforementioned phosphate group include:
5'-monophosphate ($(HO)_2(O)P$—O-5');
5'-diphosphate ($(HO)_2(O)P$—O—$P(HO)(O)$—O-5');
5'-triphosphate ($(HO)_2(O)P$—O—$(HO)(O)P$—O—$P(HO)(O)$—O-5');
5'-guanosine cap (7-methylated or non-methylated, 7m-G-O-5'-(HO)(O)P—O—(HO)(O)P—O—P(HO)(O)—O-5');
5'-adenosine cap (Appp);
any modified or unmodified nucleotide cap structure (N—O-5'-(HO)(O)P—O—(HO)(O)P—O—P(HO)(O)—O-5');
5'-monothiophosphate (phosphorothioate: $(HO)_2(S)P$—O-5');
5'-monodithiophosphate (phosphorodithioate: (HO)(HS)(S)P—O-5');
5'-phosphorothiolate ($(HO)_2(O)P$—S-5');
sulfur substituted monophosphate, diphosphate, and triphosphates (e.g., 5'-α-thiotriphosphate, 5'-γ-thiotriphosphate, and the like);
5'-phosphoramidates ($(HO)_2(O)$ P—NH-5', (HO) $(NH_2)(O)$ P—O-5');

5'-alkylphosphonates (e.g., RP(OH)(O)—O-5', $(OH)_2(O)$P-5'-$CH_2$, where R is alkyl (e.g., methyl, ethyl, isopropyl, propyl, or the like)); and 5'-alkyletherphosphonates (e.g., RP(OH)(O)—O-5', where R is alkylether (e.g., methoxymethyl, ethoxymethyl, or the like)).

In the aforementioned nucleotide residue, the aforementioned base is not particularly limited. The aforementioned base may be, for example, a natural base or a non-natural base. The aforementioned base may be, for example, a naturally-derived base or a synthetic base. As the aforementioned base, for example, a common base, a modified analog thereof, and the like can be used.

Examples of the aforementioned base include: purine bases such as adenine and guanine; and pyrimidine bases such as cytosine, uracil, and thymine. Other examples of the aforementioned base include inosine, thymine, xanthine, hypoxanthine, nubularine, isoguanisine, and tubercidine. Examples of the aforementioned base also include: 2-aminoadenine, alkyl derivatives such as 6-methylated purine; alkyl derivatives such as 2-propylated purine; 5-halouracil and 5-halocytosine; 5-propynyluracil and 5-propynylcytosine; 6-azouracil, 6-azocytosine, and 6-azothymine; 5-uracil (pseudouracil), 4-thiouracil, 5-halouracil, 5-(2-aminopropyl)uracil, 5-aminoallyluracil; 8-halogenated, aminated, thiolated, thioalkylated, hydroxylated, and other 8-substituted purines; 5-trifluoromethylated and other 5-substituted pyrimidines; 7-methylguanine; 5-substituted pyrimidines; 6-azapyrimidines; N-2, N-6, and O-6 substituted purines (including 2-aminopropyladenine); 5-propynyluracil and 5-propynylcytosine; dihydrouracil; 3-deaza-5-azacytosine; 2-aminopurine; 5-alkyluracil; 7-alkylguanine; 5-alkylcytosine; 7-deazaadenine; N6,N6-dimethyladenine; 2,6-diaminopurine; 5-amino-allyl-uracil; N3-methyluracil; substituted 1,2,4-triazoles; 2-pyridinone; 5-nitroindole; 3-nitropyrrole; 5-methoxyuracil; uracil-5-oxyacetic acid; 5-methoxycarbonylmethyluracil; 5-methyl-2-thiouracil; 5-methoxycarbonylmethyl-2-thiouracil; 5-methylaminomethyl-2-thiouracil; 3-(3-amino-3-carboxypropyl)uracil; 3-methylcytosine; 5-methylcytosine; N4-acetylcytosine; 2-thiocytosine; N6-methyladenine; N6-isopentyladenine; 2-methylthio-N6-isopentenyladenine; N-methylguanine; and O-alkylated bases. Examples of the purines and pyrimidines include those disclosed in U.S. Pat. No. 3,687,808, "Concise Encyclopedia of Polymer Science and Engineering", pp. 858 to 859, edited by Kroschwitz J. I, John Wiley & Sons, 1990, and Englisch et al, Angewandte Chemie, International Edition, 1991, vol. 30, p. 613.

Other examples of the aforementioned modified nucleotide residue include those having no base, i.e., those having an abasic ribophosphate backbone. Furthermore, as the aforementioned modified nucleotide residue, for example, those described in U.S. Provisional Application No. 60/465, 665 (filing date: Apr. 25, 2003) and International Application No. PCT/US04/07070 (filing date: Mar. 8, 2004) can be used and these documents are incorporated herein by reference.

3. Non-Nucleotide Residue

The aforementioned non-nucleotide residue is not particularly limited. The ssNc molecule of the present invention may have, as the aforementioned non-nucleotide residue, for example, a non-nucleotide structure containing an amino acid residue or a peptide residue. Examples of the amino acid composing the aforementioned amino acid residue or peptide residue include basic amino acid, acidic amino acid and the like. Examples of the aforementioned basic amino acid include lysine, arginine, histidine and the like. Examples of the aforementioned acidic amino acid include aspartic acid, glutamic acid and the like. The aforementioned non-nucleotide residue is preferably present at, for example, at least one of the aforementioned linker region (Lx) and the aforementioned linker region (Ly). The aforementioned non-nucleotide residue may be present at, for example, the aforementioned linker region (Lx) or the aforementioned linker region (Ly) or both of the aforementioned linker regions. The aforementioned linker region (Lx) and the aforementioned linker region (Ly) may be, for example, the same or different.

In the single-stranded nucleic acid molecule of the present invention, a method for modifying the 5'-terminus, 3'-terminus, the aforementioned linker region (Lx) and the aforementioned linker region (Ly) with the aforementioned biorelated substance is not particularly limited.

As a first embodiment of the modification method, for example, an example of the modification method of the 5'-terminus of the aforementioned nucleic acid molecule is shown, for example, in the following scheme 1.

scheme 1

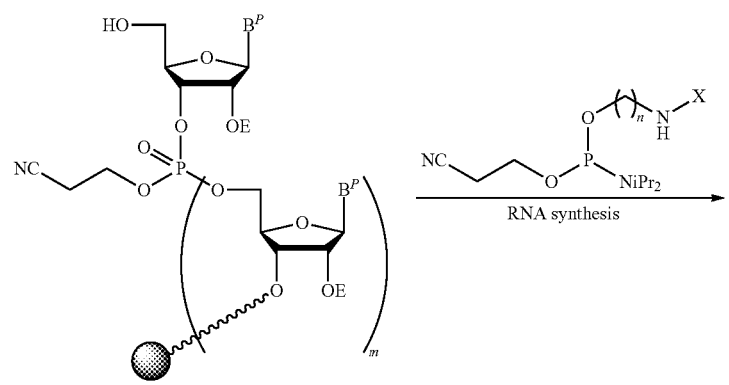

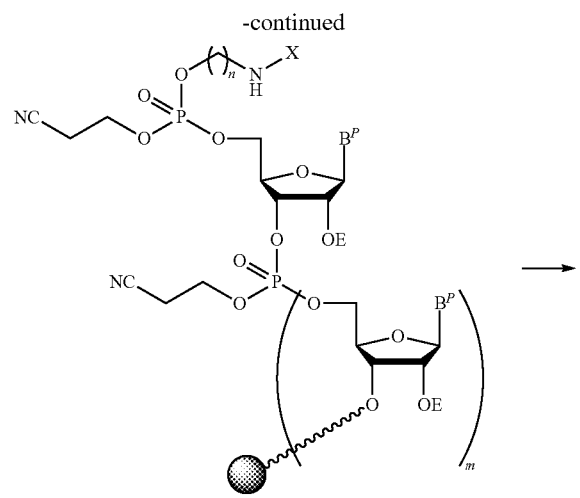
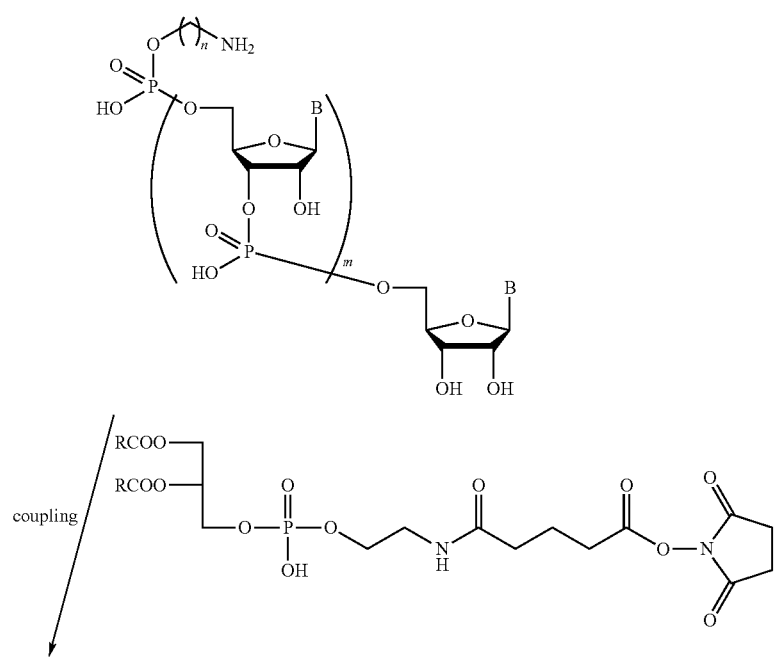

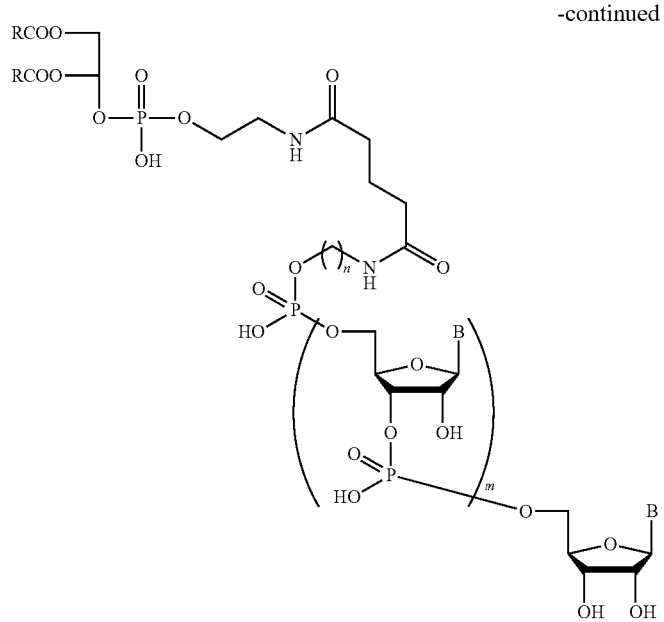

(E = 2'-OH protecting group)
(X = Tfa, Fmoc, Tr, MMTr)
(R = saturated fatty acid, unsaturated fatty acid)

As a second embodiment of the modification method, for example, an example of the modification method of a linker region having an amino acid residue or peptide residue is shown below.

First, an amidite is synthesized by the synthesis method of the following scheme 2. The following scheme 2 is an example and the method is not limited thereto. For example, Fmoc is used as a protecting group of the amino group of the Lys side chain in the following scheme 2. However, for example, Tfa may be used as in scheme 6 in the below-mentioned Example, or other protecting group may also be used.

scheme 2

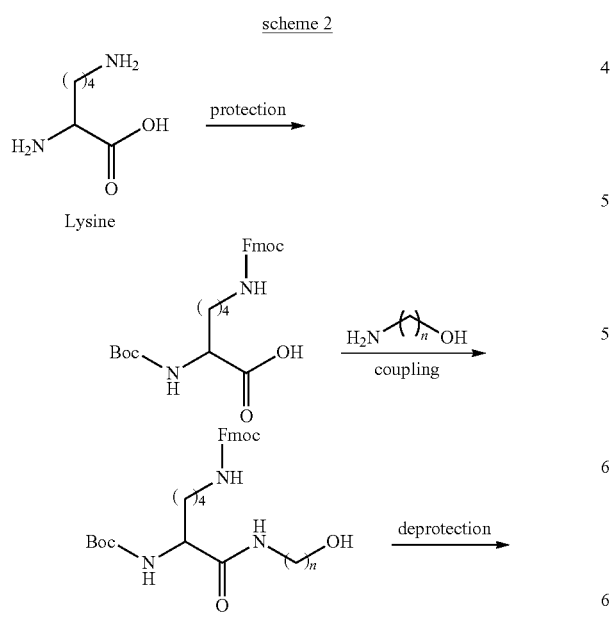

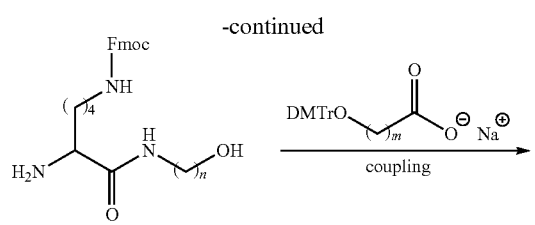

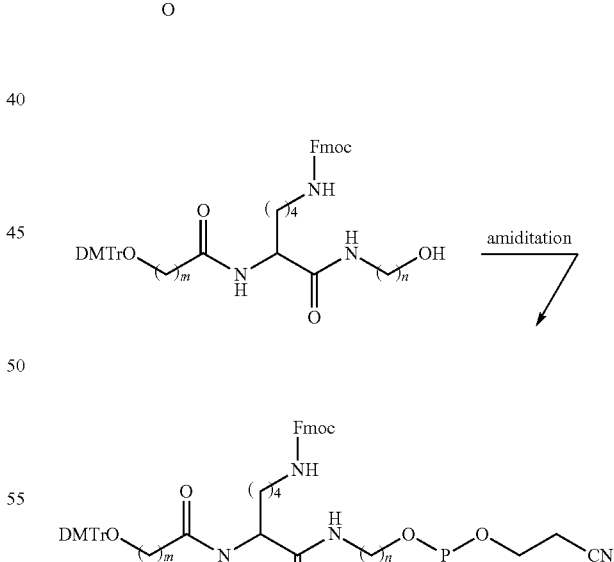

Then, using the aforementioned amidite having the aforementioned binding linker, and by the method of the following scheme 3, nucleic acid molecule is synthesized, and the aforementioned bio-related substance is linked to the aforementioned binding linker in the aforementioned nucleic acid molecule.

scheme 3

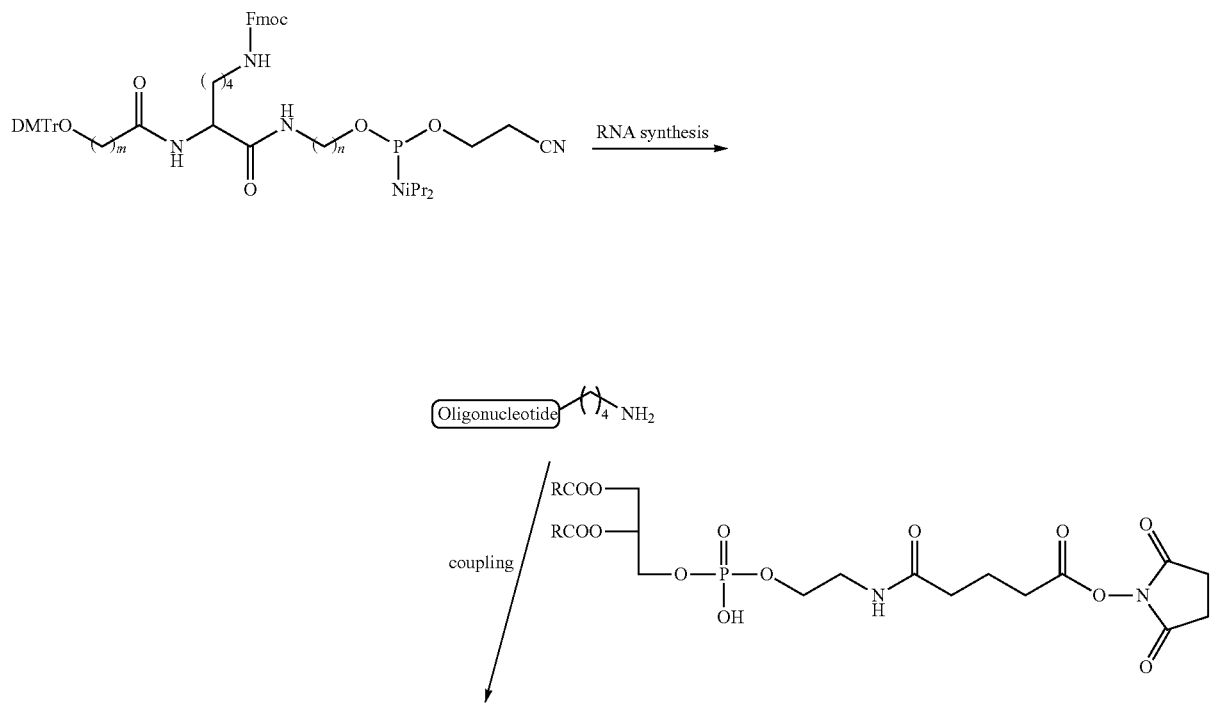

When a thiol linker is introduced as the aforementioned binding linker, the aforementioned nucleic acid molecule is synthesized by the synthesis method of the following scheme 4.

scheme 4

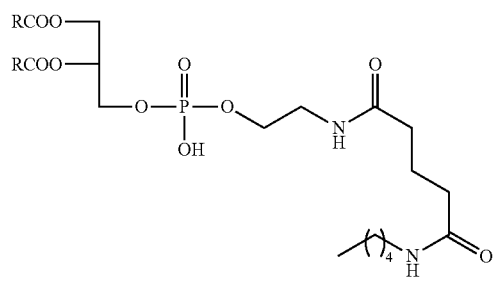

-continued

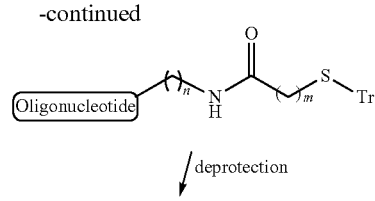

Then, as shown in the following scheme 5, the aforementioned bio-related substance is linked to the aforementioned thiol linker in the aforementioned nucleic acid molecule via an S—S bond.

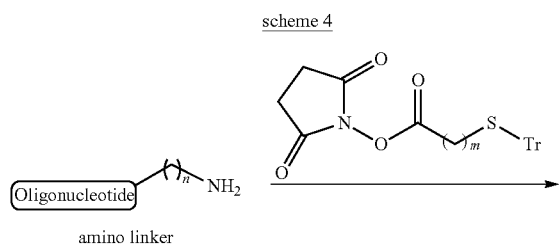

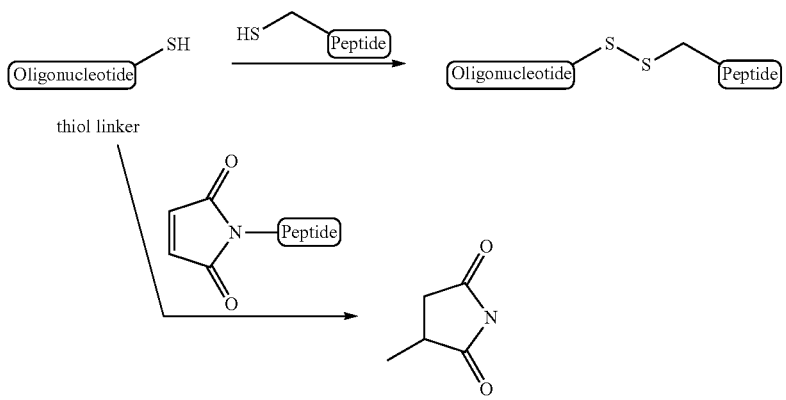

scheme 5

These methods are exemplifications and the present invention is not at all limited by these embodiments. For example, the aforementioned schemes 2 and 3 show one embodiment of the synthesis method when the aforementioned amino acid residue is a lysine residue. Even when the aforementioned amino acid residue or the aforementioned peptide residue has a structure derived from other amino acid, it can be synthesized in the same manner.

4. Composition

The expression inhibitory composition according to the present invention is, as described above, a composition for inhibiting the expression of a target gene, containing the to aforementioned ssNc molecule of the present invention. The composition of the present invention is characterized in that it contains the aforementioned ssNc molecule of the present invention, and other configurations are by no means limited. The expression inhibitory composition of the present invention can also be referred to, for example, as an expression inhibitory reagent.

According to the present invention, for example, by administering to a subject in which the aforementioned target gene is present, it is possible to inhibit the expression of the aforementioned target gene.

Furthermore, as described above, the pharmaceutical composition according to the present invention contains the aforementioned ssNc molecule of the present invention. The composition of the present invention is characterized in that it contains the aforementioned ssNc molecule of the present invention, and other configurations are by no means limited. The pharmaceutical composition of the present invention can also be referred to, for example, as a pharmaceutical product.

According to the present invention, for example, administration to a patient with a disease caused by a gene can inhibit the expression of the aforementioned gene, thereby treating the aforementioned disease. In the present invention, the term "treatment" encompasses, as mentioned above, prevention of the aforementioned diseases; improvement of the diseases; and improvement in prognosis, for example, and it can mean any of them.

In the present invention, a disease to be treated is not particularly limited, and examples thereof include diseases caused by the expression of genes. Depending on the kind of the aforementioned disease, a gene that causes the disease may be set as the aforementioned target gene, and further, depending on the aforementioned target gene, the aforementioned expression inhibitory sequence may be set as appropriate.

A specific example is as follows. By setting the aforementioned TGF-β1 gene as the aforementioned target gene and incorporating an expression inhibitory sequence for the aforementioned gene into the aforementioned ssNc molecule, the ssNc molecule can be used for the treatment of, for example, inflammatory diseases, specifically, acute lung injury and the like.

The method of using the expression inhibitory composition and the pharmaceutical composition according to the present invention (hereinafter, both the compositions simply are referred to as "the compositions") are not particularly limited, and examples thereof include administering the aforementioned ssNc molecule to a subject having the aforementioned target gene.

Examples of the aforementioned subject to which the ssNc molecule of the present invention is administered include cells, tissues, and organs. Examples of the aforementioned subject also include humans, nonhuman animals such as nonhuman mammals, i.e., mammals excluding humans. The aforementioned administration may be performed, for example, in vivo or in vitro. The aforementioned cells are not particularly limited, and examples thereof include: various cultured cells such as HeLa cells, 293 cells, NIH3T3 cells, and COS cells; stem cells such as ES cells and hematopoietic stem cells; and cells isolated from living organisms, such as primary cultured cells.

The aforementioned administration method is not particularly limited, and can be determined, for example, as appropriate depending on the subject. When the aforementioned subject is a cultured cell, the administration method may be, for example, a method using a transfection reagent, an electroporation method, or the like.

For example, each of the compositions of the present invention may contain only the ssNc molecule of the present invention or further may contain an additive(s) in addition to the ssNc molecule. The aforementioned additive is not particularly limited, and is preferably, for example, a pharmaceutically acceptable additive. The kind of the aforementioned additive is not particularly limited, and can be selected as appropriate depending on, for example, the kind of the subject.

5. Expression Inhibitory Method

The expression inhibitory method according to the present invention is, as described above, a method for inhibiting the expression of a target gene, in which the aforementioned ssNc molecule of the present invention is used. The expression inhibitory method of the present invention is characterized in that the aforementioned ssNc molecule of the present invention is used therein, and other steps and conditions are by no means limited.

In the expression inhibitory method of the present invention, the mechanism by which the aforementioned gene expression is inhibited is not particularly limited, and examples thereof include inhibition of the expression by RNA interference or RNA interference-like phenomenon. The expression inhibitory method of the present invention is, for example, a method for inducing RNA interference that inhibits the aforementioned expression of a target gene, and it can also be referred to a method for inducing the expression that is characterized in that the aforementioned ssNc molecule of the present invention is used therein.

The expression inhibitory method of the present invention includes, for example, the step of administering the aforementioned ssNc molecule to a subject in which the aforementioned target gene is present. By the aforementioned administration step, for example, the aforementioned ssNc molecule is brought into contact with the aforementioned subject to which the ssNc molecule is administered. Examples of the aforementioned subject to which the ssNc molecule of the present invention is administered include cells, tissues, and organs. Examples of the aforementioned subject also include humans, nonhuman animals such as nonhuman mammals, i.e., mammals excluding humans. The aforementioned administration may be performed, for example, in vivo or in vitro.

In the expression inhibitory method of the present invention, for example, the aforementioned ssNc molecule may be administered alone, or the aforementioned composition of the present invention containing the aforementioned ssNc molecule may be administered. The aforementioned administration method is not particularly limited and, for example, can be selected as appropriate depending on the kind of the subject.

6. Treatment Method

As described above, the method for treating a disease according to the present invention includes the step of administering the aforementioned ssNc molecule of the present invention to a patient, and the aforementioned ssNc molecule includes, as the aforementioned expression inhibitory sequence, a sequence that inhibits expression of a gene causing the aforementioned disease. The treatment method of the present invention is characterized in that the aforementioned ssNc molecule of the present invention is used therein, and other steps and conditions are by no means limited.

The description regarding the aforementioned expression inhibitory method of the present invention also applies to, for example, the treatment method of the present invention, and the like. The aforementioned administration method is not particularly limited and may be any of, for example, oral administration and parenteral administration.

7. Use of ssNc Molecule

The use according to the present invention is the use of the aforementioned ssNc molecule of the present invention for the aforementioned inhibition of the expression of a target gene. Also, the use according to the present invention is the use of the aforementioned ssNc molecule of the present invention for inducing RNA interference.

The nucleic acid molecule according to the present invention is a nucleic acid molecule for use in treatment of a disease. The aforementioned nucleic acid molecule is the aforementioned ssNc molecule of the present invention, and the aforementioned ssNc molecule includes, as the aforementioned expression inhibitory sequence, a sequence that inhibits expression of a gene causing the aforementioned disease.

EXAMPLES

The Examples of the present invention are now explained. However, the present invention is not limited to the following Examples.

Synthesis of Lys Amidite

According to the following scheme 6, DMTr-Lys amidite (7) which is a lysine (Lys) amidite, was synthesized. In the following scheme 6, "Tfa" is a trifluoroacetyl group.

scheme 6

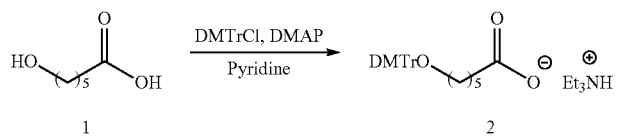

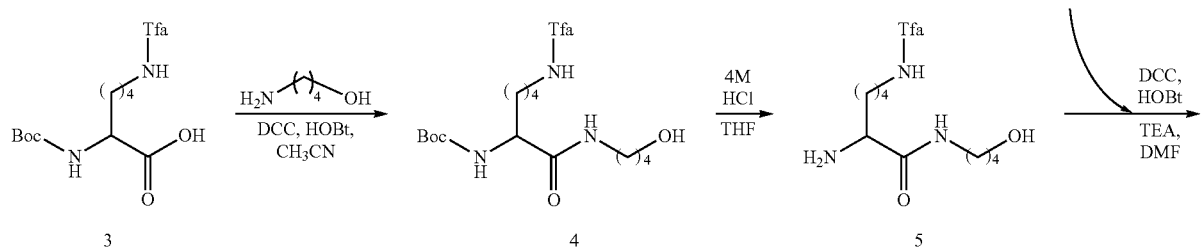

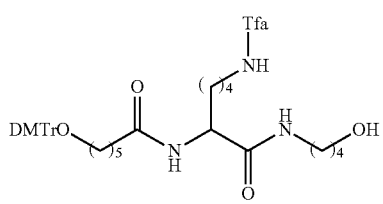 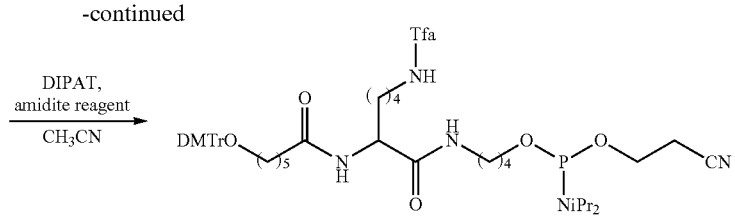

(1) Synthesis of Compound 2

To a solution (124 mL) of 6-hydroxyhexanoic acid (6 g, 15.1 mmol) in pyridine were added 4,4'-dimethoxytrityl chloride (20 g, 1.3 eq.) and dimethylaminopyridine (0.5 g, 0.1 eq.), and the mixture was stirred at room temperature for 20 hr. After completion of the reaction, methanol (10 mL) was added, the mixture was stirred for 10 min, and the solvent was evaporated. The reaction liquid was diluted with ethyl acetate, washed three times with TEAA buffer (pH 8-9), and washed once with saturated brine. The organic layer was dried over sodium sulfate, and the solvent was evaporated under reduced pressure to give compound 2 (31 g, pyridine-containing) as a pale-yellow oil.

(2) Synthesis of Compound 4

To a solution (45 mL) of compound 3 (2.7 g, 7.9 mmol), dicyclohexylcarbodiimide (1.9 g, 1.2 eq.), and 1-hydroxybenzotriazole monohydrate (2.6 g, 2.4 eq.) in acetonitrile was added a solution (5 mL) of 4-amino-1-butanol (0.86 g, 1.2 eq.) in acetonitrile, and the mixture was stirred at room temperature for 16 hr. After completion of the reaction, the precipitate was collected by filtration, and the solvent in the filtrate was evaporated by an evaporator. Dichloromethane was added to the obtained residue, and the mixture was washed three times with acetate buffer (pH 4) and three times with saturated aqueous sodium bicarbonate. The organic layer was dried over sodium sulfate, and the solvent was evaporated under reduced pressure. The obtained crude product was purified by silica gel column chromatography (eluent: dichloromethane/methanol=10/1) to give compound 4 (2.8 g, yield 85%) as a white solid. The instrumental analytical values of compound 4 are shown below.

Compound 4;
$^1$H-NMR (400 MHz, CDCl$_3$) δ: 7.07 (br, 1H), 6.72 (t, J=5.6 Hz, 1H), 4.03 (m, 1H), 3.66 (d, J=4.9 Hz, 2H), 3.37 (dd, J=12.9, 6.3 Hz, 2H), 3.29 (dd, J=12.4, 6.3 Hz, 2H), 1.83 (s, 2H), 1.66-1.60 (m, 6H), 1.44 (s, 9H), 1.41-1.37 (m, 2H)

(3) Synthesis of Compound 5

Compound 4 (2.5 g, 6.1 mmol) was stirred in hydrochloric acid/tetrahydrofuran solution (4 M, 45 mL) at room temperature for 2 hr. After completion of the reaction, the solvent was evaporated under reduced pressure. The obtained residue was dissolved in ethanol, and azeotroped with toluene. The solvent was evaporated to give compound 5 (1.9 g) as a white solid. The instrumental analytical values of compound 5 are shown below.

Compound 5;
$^1$H-NMR (400 MHz, CD$_3$OD) δ: 3.85-3.81 (m, 1H), 3.59-3.56 (m, 2H), 3.32-3.20 (m, 2H), 1.94-1.80 (m, 2H), 1.66-1.58 (m, 6H), 1.46-1.40 (m, 2H)

(4) Synthesis of Compound 6

To a solution (150 mL) of compound 2 (pyridine-containing, 24 g, 35.5 mmol), dicyclohexylcarbodiimide (8.8 g, 1.2 eq.), and 1-hydroxybenzotriazole monohydrate (7.2 g, 1.5 eq.) was added triethylamine (4.5 mL, 0.9 eq.), a solution (30 mL) of compound 5 (10 g, 0.9 eq.) in N,N-dimethylformamide was further added, and the mixture was stirred at room temperature for 20 hr. After completion of the reaction, the precipitate was collected by filtration, and the solvent in the filtrate was evaporated by an evaporator. Dichloromethane was added to the obtained residue, and the mixture was washed three times with saturated aqueous sodium bicarbonate. The organic layer was dried over sodium sulfate, and the solvent was evaporated under reduced pressure. The obtained crude product was purified by silica gel column chromatography (eluent: dichloromethane/methanol=20/1+ 0.05% pyridine) to give compound 6 (16 g, yield 70%) as a pale-yellow solid. The instrumental analytical values of compound 6 are shown below.

Compound 6;
$^1$H-NMR (400 MHz, CDCl$_3$) δ: 7.43-7.40 (m, 2H), 7.32-7.26 (m, 6H), 7.21-7.17 (m, 1H), 6.81 (d, J=8.8 Hz, 4H), 4.39-4.37 (m, 1H), 3.78 (s, 6H), 3.64-3.61 (m, 2H), 3.33-3.22 (m, 4H), 3.03 (t, J=6.6 Hz, 2H), 2.19 (t, J=7.6 Hz, 2H), 1.79-1.54 (m, 12H), 1.40-1.34 (m, 4H)

(5) Synthesis of Compound 7

To a solution (3.5 mL) of the starting material (1.26 g, 1.73 mmol), which was azeotropically dried by acetonitrile, in anhydrous acetonitrile were added diisopropylammonium tetrazolide (394 mg, 1.3 eq.) and 2-cyanoethoxy-N,N,N',N'-tetraisopropyl phosphorodiamidite (700 mg, 1.3 eq.), and the mixture was stirred at room temperature for 2.5 hr. Dichloromethane was added, the mixture was washed with saturated aqueous sodium bicarbonate and saturated brine and dried over sodium sulfate, and the solvent was evaporated. The obtained crude product was purified by silica gel column chromatography (amino silica, eluent: n-hexane/ethyl acetate=2/3) to give compound 7 (1.3 g, yield 78%) as a white solid. The instrumental analytical values of compound 7 are shown below.

Compound 7;
$^1$H-NMR (400 MHz, CDCl$_3$) δ: 7.43-7.41 (m, 2H), 7.32-7.17 (m, 7H), 6.81 (dt, J=9.3, 2.9 Hz, 4H), 4.42-4.37 (m, 1H), 3.78 (s, 6H), 3.88-3.54 (m, 6H), 3.32-3.20 (m, 4H), 3.03 (t, J=6.3 Hz, 2H), 2.19 (t, J=7.6 Hz, 2H), 1.83-1.53 (m, 12H), 1.42-1.31 (m, 4H), 1.28-1.24 (m, 2H), 1.18-1.16 (m, 12H) P-NMR (162 MHz, CDCl$_3$) δ: 146.9

Synthesis of Gly Amidite

According to the following scheme 7, DMTr-Gly amidite (compound 12) which is a glycine (Gly) amidite, was synthesized.

scheme 7

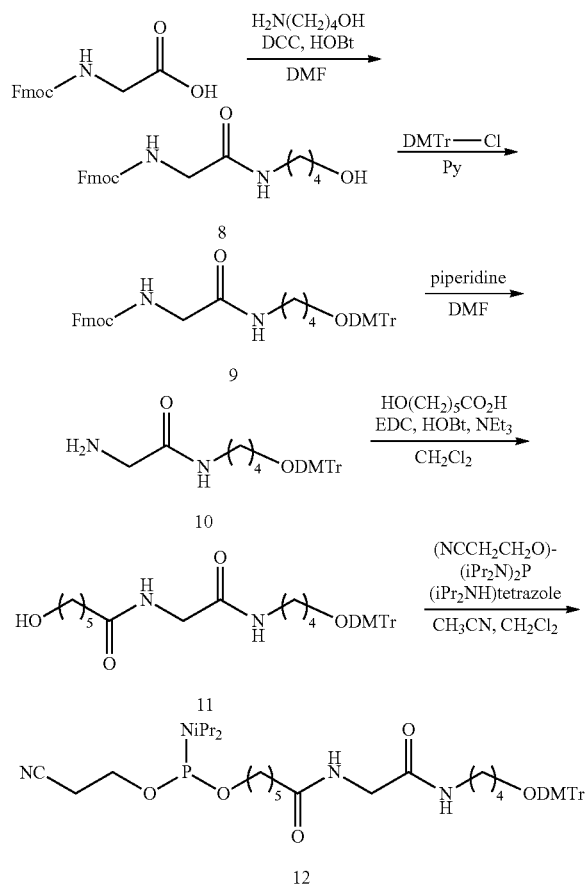

(1) N-(4-hydroxybutyl)-N$^\alpha$-Fmoc-glycinamide (compound 8)

To a solution (100 mL) of Fmoc-glycine (4.00 g, 13.45 mmol), dicyclohexylcarbodiimide (3.33 g, 16.15 mmol) and 1-hydroxybenzotriazole monohydrate (4.94 g, 32.29 mmol) in anhydrous N,N-dimethylformamide was added a solution (30 mL) of 4-aminobutanol (1.44 g, 16.15 mmol) in anhydrous N,N-dimethylformamide, and the mixture was stirred at room temperature overnight under an argon atmosphere. The resultant precipitate was separated by filtration, and the filtrate was concentrated under reduced pressure. Dichloromethane (200 mL) was added to the obtained residue, and the mixture was washed three times with saturated aqueous sodium bicarbonate, and further washed with saturated brine. After drying over sodium sulfate, the solvent was evaporated under reduced pressure. The obtained residue was subjected to silica gel column chromatography (eluent: dichloromethane-methanol (95:5) to give N-(4-hydroxybutyl)-N$^\alpha$-Fmoc-glycinamide (8) (4.30 g, 87%). The instrumental analytical values of N-(4-hydroxybutyl)-N$^\alpha$-Fmoc-glycinamide (8) are shown below.

N-(4-hydroxybutyl)-N$^\alpha$-Fmoc-glycinamide (8)

$^1$H-NMR (400 MHz, CDCl$_3$): δ=7.78-7.76 (2H, d, J=7.3 Hz), 7.65-7.63 (2H, d, J=7.3 Hz), 7.42-7.41 (2H, t, J=7.6 Hz), 7.34-7.30 (2H, td, J=7.6, 1.1 Hz), 4.42-4.40 (2H, d, J=7.3 Hz), 4.25-4.22 (1H, t, J=6.8 Hz), 3.83 (2H, s), 3.60-3.55 (2H, m), 3.30-3.25 (2H, m), 1.61-1.55 (4H, m).

(2) N-(4-O-DMTr-hydroxybutyl)-N$^\alpha$-Fmoc-glycinamide (compound 9)

Compound 8 (4.20 g, 11.40 mmol) was azeotropically dried three times with anhydrous pyridine. 4,4'-Dimethoxytrityl chloride (5.80 g, 17.10 mmol) and anhydrous pyridine (80 mL) were added to the residue by azeotropy, and the mixture was stirred at room temperature overnight. Methanol (20 mL) was added to the obtained reaction mixture and the mixture was stirred at room temperature for 30 min, and the solvent was evaporated under reduced pressure. Thereafter, dichloromethane (200 mL) was added, and the mixture was washed three times with saturated aqueous sodium bicarbonate, and further washed with saturated brine. After drying over sodium sulfate, the solvent was evaporated under reduced pressure to give unpurified N-(4-O-DMTr-hydroxybutyl)-N$^\alpha$-Fmoc-glycinamide (9) (11.40 g).

(3) N-(4-O-DMTr-hydroxybutyl)-glycinamide (compound 10)

To the unpurified compound 9 (11.40 g, 16.99 mmol) were added N,N-dimethylformamide (45 mL) and piperidine (11.7 mL) at room temperature, and the mixture was stirred at room temperature overnight. The solvent in the reaction mixture was evaporated under reduced pressure, and the obtained residue was subjected to silica gel column chromatography (eluent: dichloromethane-methanol (9:1)+0.05% pyridine) to give glycine-4,4'-dimethoxytrityloxybutanamide (3) (4.90 g, 96%, 2 steps). The instrumental analytical values of N-(4-O-DMTr-hydroxybutyl)-glycinamide (10) are shown below.

N-(4-O-DMTr-hydroxybutyl)-glycinamide (10)

$^1$H-NMR (400 MHz, CDCl$_3$): δ=7.44-7.42 (2H, m), 7.33-7.26 (6H, m), 7.21-7.20 (1H, m), 6.83-6.80 (4H, m), 3.79 (6H, s), 3.49 (2H, s), 3.30-3.28 (2H, t, J=6.3 Hz), 3.09-3.06 (2H, t, J=5.9 Hz), 1.61-1.55 (4H, m).

(4) N-(4-O-DMTr-hydroxybutyl)-N$^\alpha$-(6-hydroxyhexanoyl)-glycinamide (compound 11)

Compound 10 (4.80 g, 10.70 mmol) was azeotropically dried three times with anhydrous pyridine, 6-hydroxyhexanoic acid (1.70 g, 12.84 mmol), 1-ethyl-3-(3-dimethylaminopropyl)carbodiimide hydrochloride (2.46 g, 12.84 mmol), 1-hydroxybenzotriazole monohydrate (3.93 g, 25.69 mmol), and anhydrous dichloromethane (60 mL) were added at room temperature under an argon atmosphere, and the mixture was stirred for 10 min. Triethylamine (3.90 g, 38.53 mmol) was added to the thus-obtained mixture, and the mixture was stirred at room temperature overnight under an argon atmosphere. Dichloromethane (200 mL) was added to the obtained reaction mixture, and the mixture was washed three times with saturated aqueous sodium bicarbonate, and further washed once with saturated brine. The organic layer was separated and dried over sodium sulfate, and the solvent was evaporated under reduced pressure. The obtained residue was subjected to silica gel column chromatography (eluent: dichloromethane-methanol (95:5)+0.05% pyridine) to give N-(4-O-DMTr-hydroxybutyl)-N$^\alpha$-(6-hydroxyhexanoyl)-glycinamide (11) (4.80 g, 80%). The instrument analytical values of N-(4-O-DMTr-hydroxybutyl)-N^α-(6-hydroxyhexanoyl)-glycinamide (11) are shown below.

N-(4-O-DMTr-hydroxybutyl)-N^α-(6-hydroxyhexanoyl)-glycinamide (11)

$^1$H-NMR (400 MHz, CDCl$_3$): δ=7.43-7.40 (2H, m), 7.33-7.26 (6H, m), 7.22-7.20 (1H, m), 6.83-6.80 (4H, m), 3.85 (2H, s), 3.78 (6H, s), 3.63-3.60 (2H, t, J=6.3 Hz), 3.26-3.23 (2H, t, J=6.1 Hz), 3.07-3.05 (2H, t, J=5.6 Hz), 2.26-2.22 (2H, t, J=7.3 Hz), 1.68-1.52 (8H, m), 1.41-1.36 (2H, m).

(5) N-(4-O-DMTr-hydroxybutyl)-N^α-(6-O-(2-cyanoethyl-N,N-diisopropylphosphityl)-hydroxyhexanoyl)-glycinamide (compound 12)

Compound 11 (4.70 g, 8.35 mmol) was azeotropically dried three times with anhydrous pyridine. Then, diisopropylammonium tetrazolide (1.72 g, 10.02 mmol) was added, the mixture was deaerated under reduced pressure and filled with argon gas, and anhydrous acetonitrile (5 mL) was added. Furthermore, a solution (4 mL) of 2-cyanoethoxy-N,N,N',N'-tetraisopropyl phosphorodiamidite (3.02 g, 10.02 mmol) in a 1:1 anhydrous acetonitrile-dichloromethane mixture was added, and the mixture was stirred at room temperature for 4 hr under an argon atmosphere. Dichloromethane (150 mL) was added to the obtained reaction mixture, and the mixture was washed twice with saturated aqueous sodium bicarbonate, and further washed once with saturated brine. The organic layer was separated and dried over sodium sulfate, and the solvent was evaporated under reduced pressure. The obtained residue was subjected to column chromatography using amino silica (eluent: n-hexane-acetone (3:2)+0.1% triethylamine) to give hydroxyhexanoic acid amide glycine-4,4'-dimethoxytrityloxybutanamide phosphoramidite (12) (4.50 g, 71%, HPLC 98.2%). The instrumental analytical values of N-(4-O-DMTr-hydroxybutyl)-N^α-(6-O-(2-cyanoethyl-N,N-diisopropylphosphityl)-hydroxyhexanoyl)-glycinamide (12) are shown below.

N-(4-O-DMTr-hydroxybutyl)-N^α-(6-O-(2-cyanoethyl-N,N-diisopropylphosphityl)-hydroxyhexanoyl)-glycinamide (12)

$^1$H-NMR (400 MHz, CDCl$_3$): δ=7.43-7.40 (2H, m), 7.33-7.26 (6H, m), 7.22-7.20 (1H, m), 6.83-6.80 (4H, m), 3.85-3.81 (4H, s), 3.78 (6H, s), 3.63-3.61 (2H, t, J=6.3 Hz), 3.26-3.23 (2H, t, J=6.1 Hz), 3.05-2.97 (4H, m), 2.64-2.62 (2H, t, J=6.4 Hz), 2.25-2.23 (2H, t, J=7.3 Hz), 1.68-1.52 (8H, m), 1.40-1.38 (2H, m), 1.13-1.20 (12H, m). $^{31}$P-NMR (162 MHz, CDCl$_3$): δ=146.57.

Synthesis of Proline Amidite

According to the following scheme 8, compound 17, which is an amidite containing a proline skeleton, was synthesized.

scheme 8

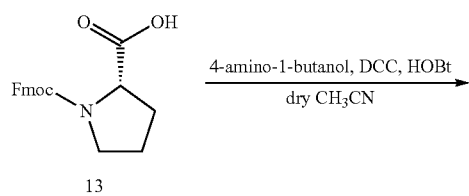

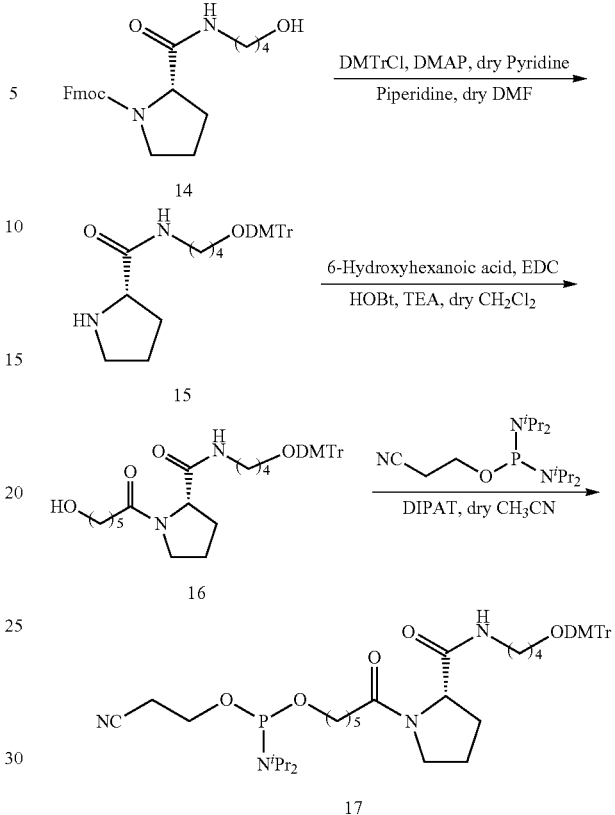

(1) N-(4-hydroxybutyl)-N^α-Fmoc-L-prolinamide (compound 14)

Compound 13 (Fmoc-L-proline) was used as a starting material. The aforementioned compound 13 (10.00 g, 29.64 mmol), 4-amino-1-butanol (3.18 g, 35.56 mmol), and 1-hydroxybenzotriazole (10.90 g, 70.72 mmol) were mixed together. The aforementioned mixture was deaerated under reduced pressure and filled with argon gas. Anhydrous acetonitrile (140 mL) was added to the aforementioned mixture at room temperature, and a solution (70 mL) of dicyclohexylcarbodiimide (7.34 g, 35.56 mmol) in anhydrous acetonitrile was further added thereto. Thereafter, this was stirred for 15 hours at room temperature under an argon atmosphere. After the completion of the reaction, the generated precipitate was removed by filtration, and the solvent in the collected filtrate was evaporated under reduced pressure. Dichloromethane (200 mL) was added to the obtained residue, and the mixture was washed with saturated aqueous sodium bicarbonate (200 mL). Then, an organic layer was collected and dried over magnesium sulfate. Thereafter, the aforementioned organic layer was filtered, and the solvent in the obtained filtrate was evaporated under reduced pressure. Diethyl ether (200 mL) was added to the residue, thereby turning the residue to powder. The thus-obtained powder was collected by filtration. Thus, compound 14 in the form of colorless powder was obtained (10.34 g, yield 84%). The instrument analytical values of the aforementioned compound 14 are shown below.

Compound 14: $^1$H-NMR (CDCl$_3$): δ 7.76-7.83 (m, 2H, Ar—H), 7.50-7.63 (m, 2H, Ar—H), 7.38-7.43 (m, 2H, Ar—H), 7.28-7.33 (m, 2H, Ar—H), 4.40-4.46 (m, 1H, CH), 4.15-4.31 (m, 2H, CH$_2$), 3.67-3.73 (m, 2H, CH$_2$), 3.35-3.52 (m, 2H, CH$_2$), 3.18-3.30 (m, 2H, CH$_2$), 2.20-2.50 (m, 4H), 1.81-2.03 (m, 3H), 1.47-1.54 (m, 2H);

Ms (FAB+): m/z 409 (M+H$^+$).

(2) N-(4-O-DMTr-hydroxybutyl)-L-prolinamide (compound 15)

Fmoc-hydroxyamide-L-proline (compound 14) (7.80 g, 19.09 mmol) was mixed with anhydrous pyridine (5 mL), and the mixture was dried by azeotropic distillation at room temperature. To the obtained residue were added 4,4'-dimethoxytritylchloride (8.20 g, 24.20 mmol), DMAP (23 mg, 0.19 mmol) and anhydrous pyridine (39 mL). The mixture was stirred at room temperature for 1 hr, methanol (7.8 mL) was added, and the mixture was stirred at room temperature for 30 min. The mixture was diluted with dichloromethane (100 ml), washed with saturated aqueous sodium hydrogen carbonate (150 ml), and the organic layer was separated. The aforementioned organic layer was dried over sodium sulfate, and filtered. The solvent in the obtained filtrate was evaporated under reduced pressure. To the obtained unpurified residue were added anhydrous dimethylformamide (39 mL) and piperidine (18.7 mL, 189 mmol), and the mixture was stirred at room temperature for 1 hr. After completion of the reaction, the solvent in the aforementioned mixture was evaporated under reduced pressure at room temperature. The obtained residue was subjected to silica gel column chromatography (trade name Wakogel C-300, eluent CH$_2$Cl$_2$: CH$_3$OH=9:1, 0.05% pyridine-containing) to give compound 15 as a pale-yellow oil (9.11 g, yield 98%). The instrumental analytical values of the aforementioned compound 15 are shown below.

Compound 15:

$^1$H-NMR (CDCl$_3$): δ 7.39-7.43 (m, 2H, Ar—H), 7.30 (d, J=8.8 Hz, 4H, Ar—H), 7.21 (tt, 1H, 4.9, 1.3 Hz, Ar—H), 6.81 (d, J=8.8 Hz, 4H, Ar—H), 3.78 (s, 6H, OCH$_3$), 3.71 (dd, H, J=6.3 Hz, 5.4 Hz, CH), 3.21 (2H, 12.9, 6.3 Hz, 2H, CH$_2$), 3.05 (t, J=6.3 Hz, 2H, CH$_2$), 2.85-2.91 (m, 2H, CH$_2$), 2.08-2.17 (m, 1H, CH), 1.85-2.00 (m, 3H), 1.55-1.65 (m, 5H);

Ms (FAB+); m/z 489 (M+H$^+$), 303 (DMTr$^+$).

(3) N-(4-O-DMTr-hydroxybutyl)-N$^α$-(6-hydroxyhexanoyl)-L-prolinamide (compound 16)

A solution (120 ml) of the obtained DMTr-amide-L-proline (compound 15) (6.01 g, 12.28 mmol), EDC (2.83 g, 14.74 mmol), 1-hydroxybenzotriazole (3.98 g, 29.47 mmol) and triethylamine (4.47 g, 44.21 mmol) in anhydrous dichloromethane was mixed. To this mixture was further added 6-hydroxyhexane acid (1.95 g, 14.47 mmol) at room temperature under an argon atmosphere, and thereafter the mixture was stirred at room temperature for 1 hr under an argon atmosphere. The aforementioned mixture was diluted with dichloromethane (600 ml), and washed 3 times with saturated brine (800 ml). The organic layer was recovered, dried over sodium sulfate, and filtered. The solvent in the obtained filtrate was evaporated under reduced pressure, whereby the aforementioned compound 16 was obtained as pale-yellow bubbles (6.29 g, yield 85%). The instrumental analytical values of the aforementioned compound 16 are shown below.

Compound 16:

$^1$H-NMR (CDCl$_2$): δ 7.41-7.43 (m, 2H, Ar—H), 7.27-7.31 (m, 4H, Ar—H), 7.19-7.26 (m, 2H, Ar—H), 7.17-7.21 (m, 1H, Ar—H), 6.79-6.82 (m, 4H, Ar—H), 4.51-4.53 (m, 1H, CH), 3.79 (s, 6H$_2$OCH$_3$), 3.61 (t, 2H, J=6.4 Hz, CH$_2$), 3.50-3.55 (m, 1H, CH), 3.36-3.43 (m, 1H, CH), 3.15-3.24 (m, 2H, CH$_2$), 3.04 (t, J=6.3 Hz, 2H, CH$_2$), 2.38-2.45 (m, 1H, CH), 2.31 (t, 6.8 Hz, 2H, CH$_2$), 2.05-2.20 (m, 1H, CH), 1.92-2.00 (m, 1H, CH), 1.75-1.83 (m, 1H, CH), 1.48-1.71 (m, 8H), 1.35-1.44 (m, 2H, CH$_2$);

Ms (FAB+): m/z 602 (M$^+$), 303 (DMTr$^+$).

(4) N-(4-O-DMTr-hydroxybutyl)-N$^α$-(6-O-(2-cyanoethyl-N,N-diisopropylphosphityl)-hydroxyhexanoyl)-L-prolinamide (compound 17)

The obtained aforementioned DMTr-hydroxydiamide-L-proline (compound 16) (8.55 g, 14.18 mmol) was mixed with anhydrous acetonitrile, and the mixture was dried by azeotropic distillation 3 times at room temperature. To the obtained residue was added diisopropylammoniumtetrazolide (2.91 g, 17.02 mmol), and the mixture was deaerated under reduced pressure and filled with argon gas. To the aforementioned mixture was added anhydrous acetonitrile (10 ml), and further, a solution (7 mL) of 2-cyanoethoxy-N,N,N',N'-tetraisopropylphosphorodiamidite (5.13 g, 17.02 mmol) in anhydrous acetonitrile was added. The mixture was stirred at room temperature for 2 hr under an argon atmosphere, then diluted with dichloromethane, washed 3 times with saturated aqueous sodium hydrogen carbonate (200 ml), and washed with saturated brine (200 ml). The organic layer was recovered, dried over sodium sulfate, and filtered. The solvent in the obtained aforementioned filtrate was evaporated under reduced pressure. The obtained residue was subjected to column chromatography using amino silica gel as a filler (eluent hexane:ethyl acetate=1:3, 0.05% pyridine-containing) to give compound 17 as a colorless syrup (10.25 g, purity 92%, yield 83%). The instrumental analytical values of the aforementioned compound 17 are shown below.

Compound 17:

$^1$H-NMR (CDCl$_3$): δ 7.40-7.42 (m, 2H, Ar—H), 7.29-7.31 (m, 4H, Ar—H), 7.25-7.27 (m, 2H, Ar—H), 7.17-7.21 (m, 1H, Ar—H), 6.80-6.82 (m, 4H, Ar—H), 4.51-4.53 (m, 1H, CH), 3.75-3.93 (m, 4H), 3.79 (s, 6H$_2$OCH$_3$), 3.45-3.60 (m, 4H), 3.35-3.45 (m, 1H, CH), 3.20-3.29 (m, 1H), 3.04 (t, J=6.4 Hz, 2H, CH$_2$), 2.62 (t, J=5.8 Hz, 2H, CH$_2$), 2.40-2.44 (m, 1H, CH), 2.31 (t, 7.8 Hz, 2H, CH$_2$), 2.03-2.19 (m, 1H, CH), 1.92-2.02 (m, 1H, CH), 1.70-1.83 (m, 1H, CH), 1.51-1.71 (m, 8H), 1.35-1.44 (m, 2H, CH$_2$), 1.18 (d, J=6.8 Hz, 6H, CH$_3$), 1.16 (d, J=6.8 Hz, 6H, CH$_3$);

$^{31}$P-NMR (CDCl$_3$): δ147.17;

Ms (FAB+): m/z 802(M$^+$), 303 (DMTr$^+$), 201 (C$_8$H$_{19}$N$_2$OP$^+$).

Synthesis of Fatty Acid Active Ester Form

According to the following scheme 9, myristic acid-N-hydroxysuccinimide ester (C14-NHS), palmitic acid-N-hydroxysuccinimide ester (C16-NHS) or stearic acid-N-hydroxysuccinimide ester (C18-NHS) was each synthesized. In addition, according to the following scheme 10, oleic acid-N-hydroxysuccinimide ester (C18:1-NHS) was synthesized.

scheme 9

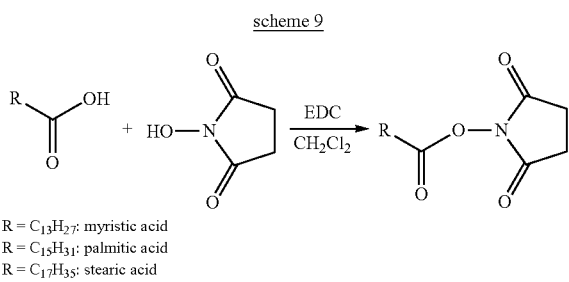

R = $C_{13}H_{27}$: myristic acid
R = $C_{15}H_{31}$: palmitic acid
R = $C_{17}H_{35}$: stearic acid scheme 10

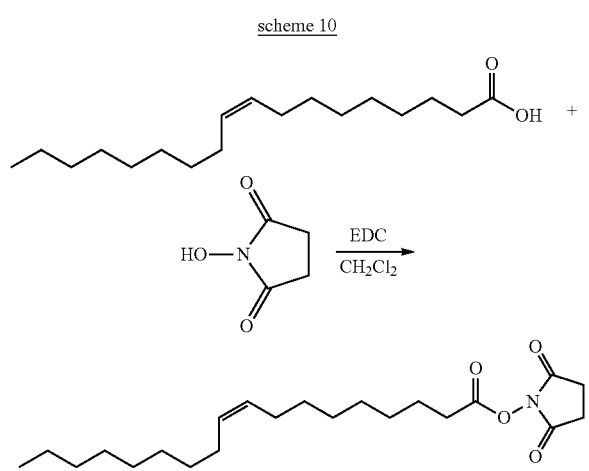

Synthesis of Myristic Acid-N-Hydroxysuccinimide Ester (C14-NHS)

Myristic acid (1.5 g, 6.6 mmol) was dissolved in dichloromethane (30 ml) and the mixture was stirred. To this solution were added N-hydroxysuccinimide (0.91 g, 1.2 eq.) and 1-ethyl-3-(3-dimethylaminopropyl)carbodiimide hydrochloride (EDC) (1.5 g, 1.2 eq.), and the mixture was stirred overnight. After washing twice with water, the mixture was washed once with saturated brine, dried over sodium sulfate, and the solvent was evaporated under reduced pressure. The obtained residue was purified by silica gel column chromatography (ethyl acetate/hexane=1/3) to give the object product (1.4 g, yield 67%). The NMR measurement results of the obtained myristic acid-N-hydroxysuccinimide ester (C14-NHS) are shown below.

Myristic Acid-N-Hydroxysuccinimide Ester (C14-NHS)

$^1$H-NMR (CDCl$_3$) δ: 2.83 (4H, s), 2.60 (2H, t, J=7.6 Hz), 1.74 (2H, q, J=7.6 Hz), 1.44 (2H, q, J=6.9 Hz), 1.48-1.22 (18H, m), 0.88 (3H, t, J=6.8 Hz).

Synthesis of Palmitic Acid-N-Hydroxysuccinimide Ester (C16-NHS)

Palmitic acid (6.0 g, 23 mmol) was dissolved in dichloromethane (110 ml) and the mixture was stirred. To this solution were added N-hydroxysuccinimide (3.2 g, 1.2 eq.) and 1-ethyl-3-(3-dimethylaminopropyl)carbodiimide hydrochloride (EDC) (5.4 g, 1.2 eq.), and the mixture was stirred overnight. After washing twice with water, the mixture was washed once with saturated brine, dried over sodium sulfate, and the solvent was evaporated under reduced pressure. The obtained residue was purified by silica gel column chromatography (ethyl acetate/hexane-1/2) to give the object product (7.8 g, yield 94%). The NMR measurement results of the obtained palmitic acid-N-hydroxysuccinimide ester (C16-NHS) are shown below.

Palmitic Acid-N-Hydroxysuccinimide Ester (C16-NHS)

$^1$H-NMR (CDCl$_3$) δ: 2.84 (4H, s), 2.60 (2H, t, J=7.6 Hz), 1.74 (2H, q, J=7.6 Hz), 1.38 (2H, q, J=6.9 Hz), 1.43-1.20 (m, 22H), 0.88 (3H, t, J=6.8 Hz).

Synthesis of Stearic Acid-N-Hydroxysuccinimide Ester (C18-NHS)

Stearic acid (3.0 g, 11 mmol) was dissolved in dichloromethane (100 ml) and the mixture was stirred. To this solution were added N-hydroxysuccinimide (1.5 g, 1.2 eq.) and 1-ethyl-3-(3-dimethylaminopropyl)carbodiimide hydrochloride (EDC) (2.4 g, 1.2 eq.), and the mixture was stirred for 2 days. After washing twice with water, the mixture was washed once with saturated brine, dried over sodium sulfate, and the solvent was evaporated under reduced pressure. The obtained residue was purified by silica gel column chromatography (ethyl acetate/hexane=1/3) to give the object product (2.8 g, yield 70%). The NMR measurement results of the obtained stearic acid-N-hydroxysuccinimide ester (C18-NHS) are shown below. stearic acid-N-hydroxysuccinimide ester (C18-NHS):

$^1$H-NMR (CDCl$_3$) δ: 2.84 (4H, m), 2.60 (2H, t, J=7.6 Hz), 1.74 (2H, q, J=7.6 Hz), 1.38 (2H, q, J=6.9 Hz), 1.43-1.20 (m, 26H), 0.88 (3H, t, J=6.8 Hz).

Synthesis of Oleic Acid-N-Hydroxysuccinimide Ester (C18:1-NHS)

Oleic acid (4.0 g, 14 mmol) was dissolved in dichloromethane (70 ml) and the mixture was stirred. To this solution were added N-hydroxysuccinimide (2.0 g, 1.2 eq.) and 1-ethyl-3-(3-dimethylaminopropyl)carbodiimide hydrochloride (EDC) (3.3 g, 1.2 eq.), and the mixture was stirred overnight. After washing twice with water, the mixture was washed once with saturated brine, dried over sodium sulfate, and the solvent was evaporated under reduced pressure. The obtained residue was purified by silica gel column chromatography (ethyl acetate/hexane=1/3) to give the object product (5.2 g, yield 97%). The NMR measurement results of the obtained oleic acid-N-hydroxysuccinimide ester (C18:1-NHS) are shown below.

Oleic Acid-N-Hydroxysuccinimide Ester (C18:1-NHS)

$^1$H-NMR (CDCl$_3$) δ: 5.35 (2H, m), 2.83 (4H, s), 2.60 (2H, t, J=7.6 Hz), 2.01 (4H, m), 1.75 (2H, q, J=7.6 Hz), 1.41-1.27 (20H, m), 0.88 (3H, t, J=6.8 Hz).

Example A1: Synthesis of 5'-Terminus Lipid-Conjugated Nucleic Acid

A 5'-terminus lipid-conjugated nucleic acid wherein a lipid is bound to the 5'-terminus (to be referred to as "5'-terminus lipid conjugate", "5'-terminus lipid-modified nucleic acid", or simply "lipid-modified nucleic acid") was synthesized. The structure of the synthesized 5'-terminus lipid-conjugated nucleic acid is schematically shown below. In the following 5'-terminus lipid-conjugated nucleic acid, the "Negative control" has a sequence non-complementary to the target sequence to be mentioned below (sequence of firefly luciferase gene retained by breast cancer cell line MCF-7 stably expressing firefly luciferase (pGL3 Luc)), and corresponds to Reference Example. The "target sequence" is a nucleic acid having a sequence complementary to the aforementioned target sequence. Of the "target sequence", siRNA type is a nucleic acid wherein a lipid is bound to one of the 5'-termini of the double-stranded nucleic acid, and corresponds to Reference Example. Of the "target sequence", nkRNA (registered trade mark) type and PnkRNA (trade name) type are nucleic acids wherein a lipid is bound to the 5'-terminus of the single-stranded nucleic acid, and correspond to Example.

| kind of 5'-terminus lipid conjugate | | |
|---|---|---|
| siRNA | | NI-0089-C16  NI-0000-C16<br>NI-0089-DPPE  NI-0000-DPPE<br>NI-0089  NI-0000 |
| nkRNA ® | | NK-0139-C16<br>NK-0139-DPPE<br>NK-0139 |
| PnkRNA ™ | | PK-0071-C16<br>PK-0071-DPPE<br>PK-0071 |

∿∿∿: C16 (single-chain lipid)
DPPE (double-chain lipid)

Specific sequences and structures of NI-0089-C16 and NI-0089-DPPE, which are of the siRNA type in the aforementioned 5'-terminus lipid-conjugated nucleic acids, and NI-0089s-amino which is a synthesis starting material thereof, are shown below including the structure of the lipid bound to the 5'-terminus.

structure of siRNA type

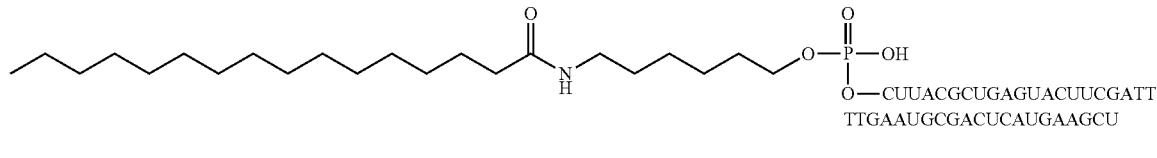

NI-0089-C16

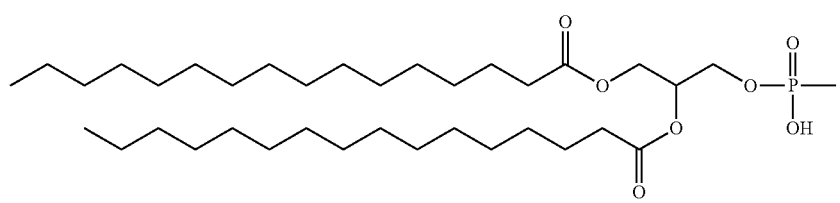

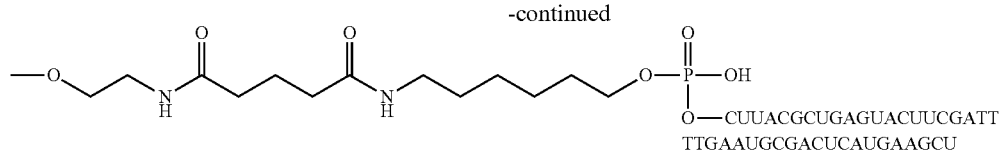

O—CUUACGCUGAGUACUUCGATT
TTGAAUGCGACUCAUGAAGCU

NI-0089-DPPE

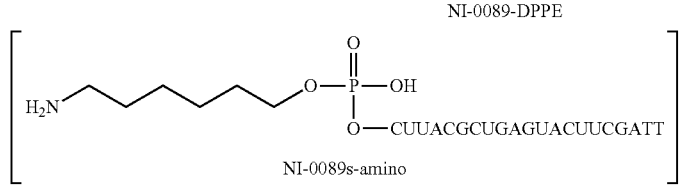

NI-0089s-amino

The upper side sequences of NI-0089-016 and NI-0089-DPPE are shown by the following SEQ ID NO: 1, and the lower side sequences are shown by the following SEQ ID NO: 2. "B" at the 5'-terminus of SEQ ID NO: 1 shows a bio-related substance (lipid). The sequence of NI-0089s-amino is also shown by the following SEQ ID NO: 1.

(SEQ ID NO: 1)
5'-B-CUUACGCUGAGUACUUCGATT-3'

-continued (SEQ ID NO: 2)
5'-UCGAAGUACUCAGCGUAAGTT-3'

Specific sequences and structures of NK-0139-C16 and NK-0139-DPPE, which are of the nkRNA type in the aforementioned 5'-terminus lipid-conjugated nucleic acid, and NK-0139-amino which is a synthesis starting material thereof, are shown below including the structure of the lipid bound to the 5'-terminus.

structure of nkRNA type

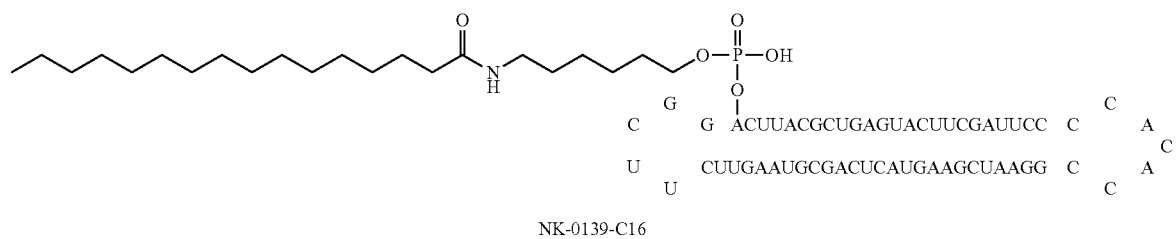

NK-0139-C16

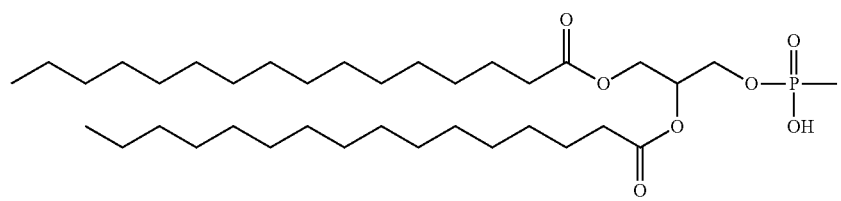

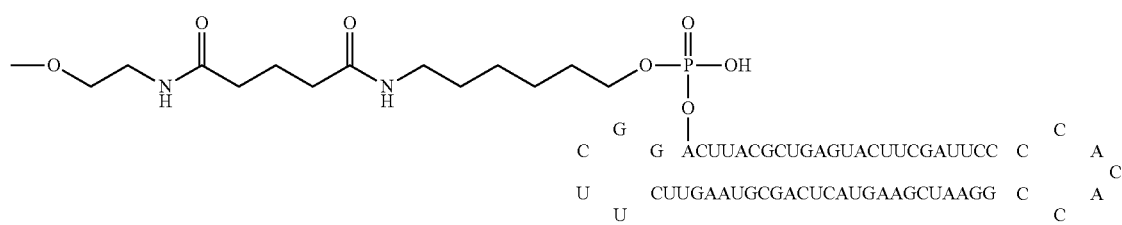

NK-0139-DPPE

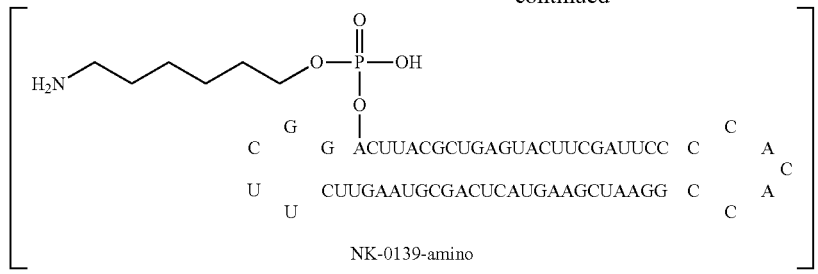

NK-0139-amino

Of the sequences of NK-0139-C16, NK-0139-DPPE and NK-0139-amino, the sequence of region Xc is shown by the following SEQ ID NO: 3, the sequence of region X is shown by the following SEQ ID NO: 4, and the whole sequence is shown by the following SEQ ID NO: 5. "B" at the 5'-terminus of SEQ ID NO: 5 shows a bio-related substance (lipid).

```
            (SEQ ID NO: 3)                  (SEQ ID NO: 4)
5'-ACUUACGCUGAGUACUUCGAUUCC-3'   5'-GGAAUCGAAGUACUCAGCGUAACUUC-3'
                                                      (SEQ ID NO: 5)

5'-B-ACUUACGCUGAGUACUUCGAUUCCCCACACCGGAAUCGAAGUACUCAGCGUAAGUUCUUCGG-3'
     ‾‾‾‾‾‾‾‾‾‾‾‾‾‾‾‾‾‾‾‾‾‾‾‾ ‾‾‾‾‾‾ ‾‾‾‾‾‾‾‾‾‾‾‾‾‾‾‾‾‾‾‾‾‾‾‾‾‾ ‾‾‾‾‾‾
              X c              L x              X               Y L y Y c
```

Specific sequences and structures of PK-0071-C16 and PK-0071-DPPE, which are of the PnkRNA type, in the aforementioned 5'-terminus lipid-conjugated nucleic acid, and PK-0071-amino which is a synthesis starting material thereof, are shown below including the structure of the lipid bound to the 5'-terminus.

structure of PnkRNA type

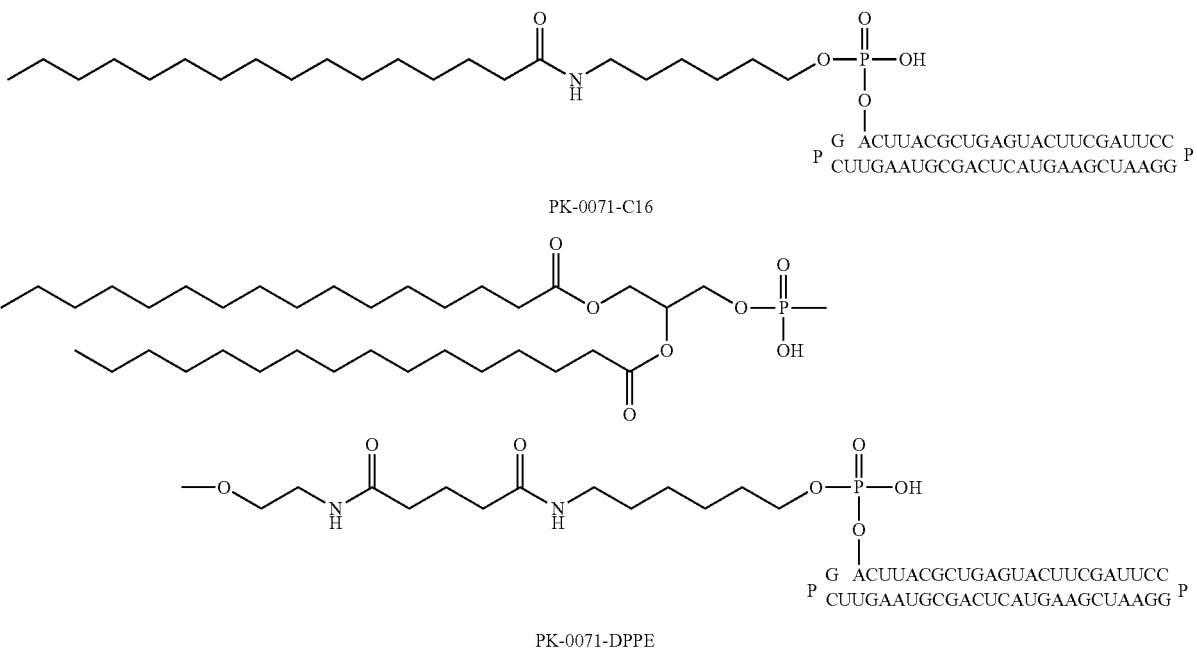

PK-0071-C16

PK-0071-DPPE

-continued

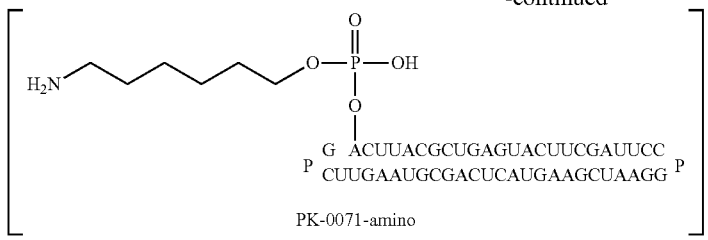

PK-0071-amino

The sequences of PK-0071-C16, PK-0071-DPPE and PK-0071-amino are shown by the following SEQ ID NO: 6. The sequence of the following SEQ ID NO: 6 is the same as that of SEQ ID NO: 5 except that the linker regions Lx and Ly are replaced by a proline residue Lp instead of the nucleic acid sequence. In addition, a specific structure of Lp is shown by the following formula.

(SEQ ID NO: 6)
5'-B-ACUUACGCUGAGUACUUCGAUUCC-Lp-
GGAAUCGAAGUACUCAGCGUAAGUUC-Lp-G-3'

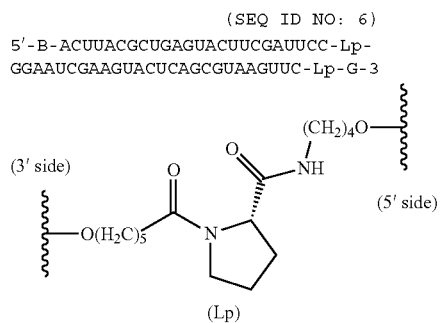

(Lp)

Specific sequence and structure of NI-0000 having a negative control sequence in the aforementioned 5'-terminus lipid-conjugated nucleic acid are shown below.

NI-0000
UACUAUUCGACACGCGAAGTT

TTAUGAUAAGCUGUGCGCUUC

The upper side sequence of NI-0000 is shown by the following SEQ ID NO: 7, and the lower side sequence is shown by the following SEQ ID NO: 8.

(SEQ ID NO: 7)
5'-UACUAUUCGACACGCGAAGTT-3'

(SEQ ID NO: 8)
5'-CUUCGCGUGUCGAAUAGUAUT-3'

The sequences of NI-0000-C16 and NI-0000-DPPE are the same as that of NI-0000 except that the upper side sequence is replaced by the following SEQ ID NO: 9 rather than the following SEQ ID NO: 7. The following SEQ ID NO: 9 is the same as SEQ ID NO: 7 except that a bio-related substance (lipid) B is bound to the 5'-side, and the structure of B is the same as that of the aforementioned si type or nk type RNA. The sequence of NI-0000s-amino, which is a synthesis starting material of NI-0000-C16 and NI-0000-DPPE, is also shown by the following SEQ ID NO: 9. In this case, the structure of the aforementioned B is represented by $NH_2-(CH_2)_6-O-PO(OH)-O-$.

(SEQ ID NO: 9)
5'-B-UACUAUUCGACACGCGAAGTT-3'

Each of the aforementioned RNAs (5'-terminus lipid-conjugated nucleic acids) was synthesized as follows.

Synthesis of NI-0089s-Amino

NI-0089s-amino was synthesized from the 3'-side to the 5'-side based on a phosphoramidite method, by a nucleic acid synthesizer (trade name ABI Expedite (registered trademark) 8909 Nucleic Acid Synthesis System, Applied Biosystems). RNA Phosphoramidites (2'-O-TBDMSi, trade name, ST Pharma) was used as RNA amidite for the aforementioned synthesis (hereinafter the same). In addition, 5'-Amino-Modifier C6-TFA amidite was used as for the introduction of an amino group into the 5'-terminus (hereinafter the same). The aforementioned amidite was deprotected according to a conventional method, and the synthesized RNA was purified by HPLC. In the following Examples, synthesis of RNA (formation of nucleic acid sequence) was performed in the same manner unless particularly indicated.

5'-Terminus Modification

Synthesis of NI-0089-C16

NI-0089s-amino (1.5 mM, 60 µL), 10 mM C16-NHS/DMF solution (356 µL), 5% aqueous diisopropylamine solution (5 µL) and DMF (150 µL) were mixed, and the mixture was stirred at room temperature overnight. The reaction liquid was precipitated in ethanol, and the resulting precipitate was dissolved in distilled water for injection and purified by HPLC (Develosil C8-UG-5, 2.5 mm, 10×50 mm, 4.7 mL/min, 260 nm, 35° C., Buffer A: 50 mM TEAA, 5% $CH_3CN$; Buffer B: $CH_3CN$; B conc. 0-100%/20 min), and the peak of the object product was fractionated. The fraction obtained by fractionation was precipitated in ethanol, and the resulting precipitate was dissolved in distilled water for injection. The absorbance at UV 260 nm was measured, and the yield was calculated. In this way, NI-0089s-amino-C16 (sense strand of NI-0089-C16, the aforementioned SEQ ID NO: 1) (1.16 mg, purity 97.64%) was obtained. The mass spectrometry value was 7024.17 (Calculated: 7024.37). The obtained NI-0089s-amino-C16 and an antisense strand of NI-0089 were mixed and the mixture was subjected to an annealing operation to give NI-0089-C16.

Synthesis of NI-0000-C16

NI-0000s-amino was synthesized by a nucleic acid synthesis method similar to that for NI-0089s-amino, and NI-0000-C16 was synthesized by a method similar to that of NI-0089-C16 except that NI-0000s-amino was used instead of NI-0089s-amino.

Synthesis of NK-0139-C16

NK-0139-amino was synthesized by a nucleic acid synthesis method similar to that of NI-0089s-amino. Then, NK-0139-amino (687 μM, 50 μL), 10 mM C16-NHS/DMF solution (172 μL), 5% aqueous diisopropylamine solution (5 μL) and DMF (75 μL) were mixed, and the mixture was stirred at room temperature overnight. The reaction liquid was precipitated in ethanol, and the resulting precipitate was dissolved in distilled water for injection and purified by HPLC (Develosil C8-UG-5, 2.5 mm, 10×50 mm, 4.7 mL/min, 260 nm, 35° C., Buffer A: 50 mM TEAA, 5% $CH_3CN$; Buffer B: $CH_3CN$; B conc. 0-100%/20 min), and the peak of the object product was fractionated. The fraction obtained by fractionation was precipitated in ethanol, and the resulting precipitate was dissolved in distilled water for injection. The absorbance at UV 260 nm was measured, and the yield was calculated. In this way, NK-0139-C16 (1.33 mg, purity 95.67%) was obtained. The mass spectrometry value was 20173.23 (Calculated: 20173.11).

Synthesis of PK-0071-Amino

PK-0071-amino was synthesized by a phosphoroamidite method similar to the above. To be specific, the aforementioned compound 17 was first linked to the 5'-side of guanosine to introduce a proline residue. Then, the aforementioned RNA shown by SEQ ID NO: 4 was linked to the 5'-side of the aforementioned guanosine via the aforementioned proline residue. Furthermore, the aforementioned compound 17 was linked to the 5'-side to introduce a proline residue. Furthermore, RNA shown by the following SEQ ID NO: 10 was linked to the 5'-side via the aforementioned proline residue. The following SEQ ID NO: 10 is the same as the aforementioned SEQ ID NO: 3 except that B was linked to the 5'-terminus. In the case of PK-0071-amino, the structure of the aforementioned B is represented by $NH_2$—$(CH_2)_6$—O—PO(OH)—O—.

(SEQ ID NO: 10)
5'-B-ACUUACGCUGAGUACUUCGAUUCC-3'

Synthesis of PK-0071-C16

PK-0071-amino (739 μM, 100 μL), 10 mM C16-NHS/DMF solution (296 μL), 5% aqueous diisopropylamine solution (3 μL) and DMF (250 μL) were mixed, and the mixture was stirred at room temperature overnight. The reaction liquid was precipitated in ethanol, and the resulting precipitate was dissolved in distilled water for injection and purified by HPLC (Develosil C8-UG-5, 2.5 mm, 10×50 mm, 4.7 mL/min, 260 nm, 35° C., Buffer A: 50 mM TEAA, 5% $CH_3CN$; Buffer B: $CH_3CN$; B conc. 0-100%/20 min), and the peak of the object product was fractionated. The fraction obtained by fractionation was precipitated in ethanol, and the resulting precipitate was dissolved in distilled water for injection. The absorbance at UV 260 nm was measured, and the yield was calculated. In this way, PK-0071-C16 (0.57 mg, purity 94.59%) was obtained. The mass spectrometry value was 17450.88 (Calculated: 17450.78).

Synthesis of NI-0089-DPPE

NI-0089s-amino (1.5 mM, 60 μL), 10 mM DPPE-NHS ethanol solution (445 μL), 5% aqueous triethylamine solution (15 μL), ethanol (130 μL) and distilled water for injection (220 μL) were mixed, and the mixture was stirred at room temperature overnight. The reaction liquid was precipitated in ethanol, and the resulting precipitate was dissolved in distilled water for injection and purified by HPLC (Develosil C8-UG-5, 2.5 mm, 10×50 mm, 4.7 mL/min, 260 nm, 35° C., Buffer A: 50 mM TEAA, 5% $CH_3CN$; Buffer B: $CH_3CN$; B conc. 0-100%/20 min), and the peak of the object product was fractionated. The fraction obtained by fractionation was precipitated in ethanol, and the resulting precipitate was dissolved in distilled water for injection. The absorbance at UV 260 nm was measured, and the yield was calculated. NI-0089s-amino-DPPE (sense strand of NI-0089-DPPE, the aforementioned SEQ ID NO: 1) (1.53 mg, purity 92.41%) was obtained. The mass spectrometry value was 7573.71 (Calculated: 7573.67). The obtained NI-0089s-amino-DPPE and an antisense strand of NI-0089 were mixed and the mixture was subjected to an annealing operation to give NI-0089-DPPE.

Synthesis of NK-0139-DPPE

NK-0139-amino (687 μM, 100 μL), 10 mM DPPE-NHS ethanol solution (343 μL), 5% aqueous triethylamine solution (15 μL), ethanol (50 μL) and distilled water for injection (150 μL) were mixed, and the mixture was stirred at room temperature overnight. The reaction liquid was precipitated in ethanol, and the resulting precipitate was dissolved in distilled water for injection and purified by HPLC (Develosil C8-UG-5, 2.5 mm, 10×50 mm, 4.7 mL/min, 260 nm, 35° C., Buffer A: 50 mM TEAA, 5% $CH_3CN$; Buffer B: $CH_3CN$; B conc. 0-100%/20 min), and the peak of the object product was fractionated. The fraction obtained by fractionation was precipitated in ethanol, and the resulting precipitate was dissolved in distilled water for injection. The absorbance at UV 260 nm was measured, and the yield was calculated. NK-0139-DPPE (1.42 mg, purity 95.79%) was obtained. The mass spectrometry value was 20722.75 (Calculated: 20722.41).

Synthesis of PK-0071-DPPE

PK-0071-amino (739 μM, 100 μL), 10 mM DPPE-NHS ethanol solution (369 μL), 5% aqueous triethylamine solution (10 μL), ethanol (110 μL) and distilled water for injection (120 μL) were mixed, and the mixture was stirred at room temperature overnight. The reaction liquid was precipitated in ethanol, and the resulting precipitate was dissolved in distilled water for injection and purified by HPLC (Develosil C8-UG-5, 2.5 mm, 10×50 mm, 4.7 mL/min, 260 nm, 35° C., Buffer A: 50 mM TEAA, 5% $CH_3CN$; Buffer B: $CH_3CN$; B conc. 0-100%/20 min), and the peak of the object product was fractionated. The fraction obtained by fractionation was precipitated in ethanol, and the resulting precipitate was dissolved in distilled water for injection. The absorbance at UV 260 nm was measured, and the yield was calculated. In this way, PK-0071-DPPE (2.18 mg, purity 97.67%) was obtained. The mass spectrometry value was 18000.50 (Calculated: 18000.08).

(Example B1) Inhibitory Effect on Expression of Firefly Luciferase Gene by 5'-Terminus Lipid-Conjugated Nucleic Acid Using the above-mentioned 5'-terminus lipid-conjugated nucleic acid, inhibition of the expression of firefly luciferase gene in vitro was confirmed.

(1) Materials and Method

RNA solutions were prepared by dissolving each of the aforementioned RNAs in distilled water for injection (Otsuka Pharmaceutical Co., Ltd., hereinafter the same) to achieve the desired concentration (20 µmol/L).

Breast cancer cell line MCF-7 stably expressing firefly luciferase (pGL3 Luc) was used, 10% FBS-containing RPMI Medium 1640 (Invitrogen) was used as the medium. The culture conditions were set to 37° C. and 5% $CO_2$.

More specifically, breast cancer cell line MCF-7 stably expressing firefly luciferase (pGL3 Luc) was cultured as follows.

[1] The aforementioned cells were cultured in the medium, and the culture medium was dispensed to a 96 well plate by 50 µL to $1 \times 10^4$ cells/well.

[2] Then, the aforementioned cells in the well were transfected with the RNA sample by using a transfection reagent Lipofectamine 2000 (Invitrogen) according to the attached protocol. Specifically, 50 µL/well of a complex of the aforementioned RNA sample and the aforementioned transfection reagent was added to the total amount of 100 µL, and the final concentration of the aforementioned RNA sample to 0.1, 1 or 10 nmol/L. As control 1, the cells to which the aforementioned RNA sample and the aforementioned transfection reagent were not added (−) were prepared and, as control 2, the cells to which the aforementioned RNA sample was not added in transfection but the aforementioned transfection reagent was added alone (mock) were prepared.

[3] The cells were further cultured for 48 hr after the aforementioned transfection.

The luciferase activity was measured as follows. The luciferase activity measurement is the measurement of an inhibitory effect on the expression of firefly luciferase gene, which is retained by the breast cancer cell line MCF-7 stably expressing firefly luciferase (pGL3 Luc).

[1] First using Steady-Glo Luciferase Assay System (trade name) (Promega), the activity of firefly luciferase was measured according to the attached protocol. To be specific, a substrate solution (100 µL) was added per the aforementioned well, and the amount of luciferase luminescence was measured by a multilabel reader ARVO X2 (PerkinElmer).

[2] The results of the luciferase activity measurement in the aforementioned [1] were presented as the relative activity to that of the cell free from addition of the RNA sample and the transfection reagent (−) (the aforementioned control 1, non-addition cell group) as 1.

(2) Results

Figure 3:
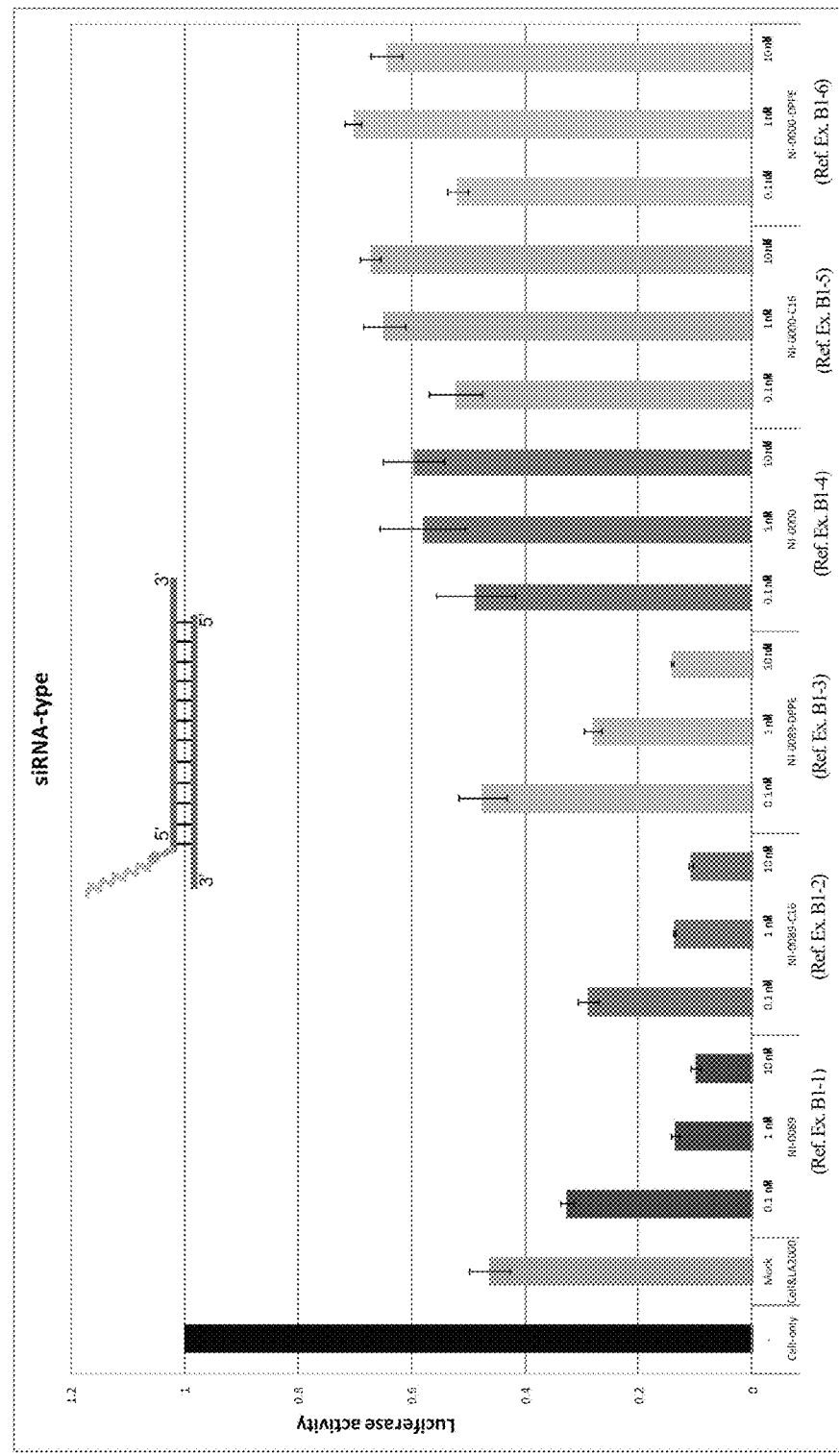
FIG. 3 is a graph showing the firefly luciferase gene expression inhibitory effect (relative activity of luciferase) of breast cancer cell line MCF-7 stably expressing firefly luciferase (pGL3 Luc) in the Example of the present invention.
Figure 4:
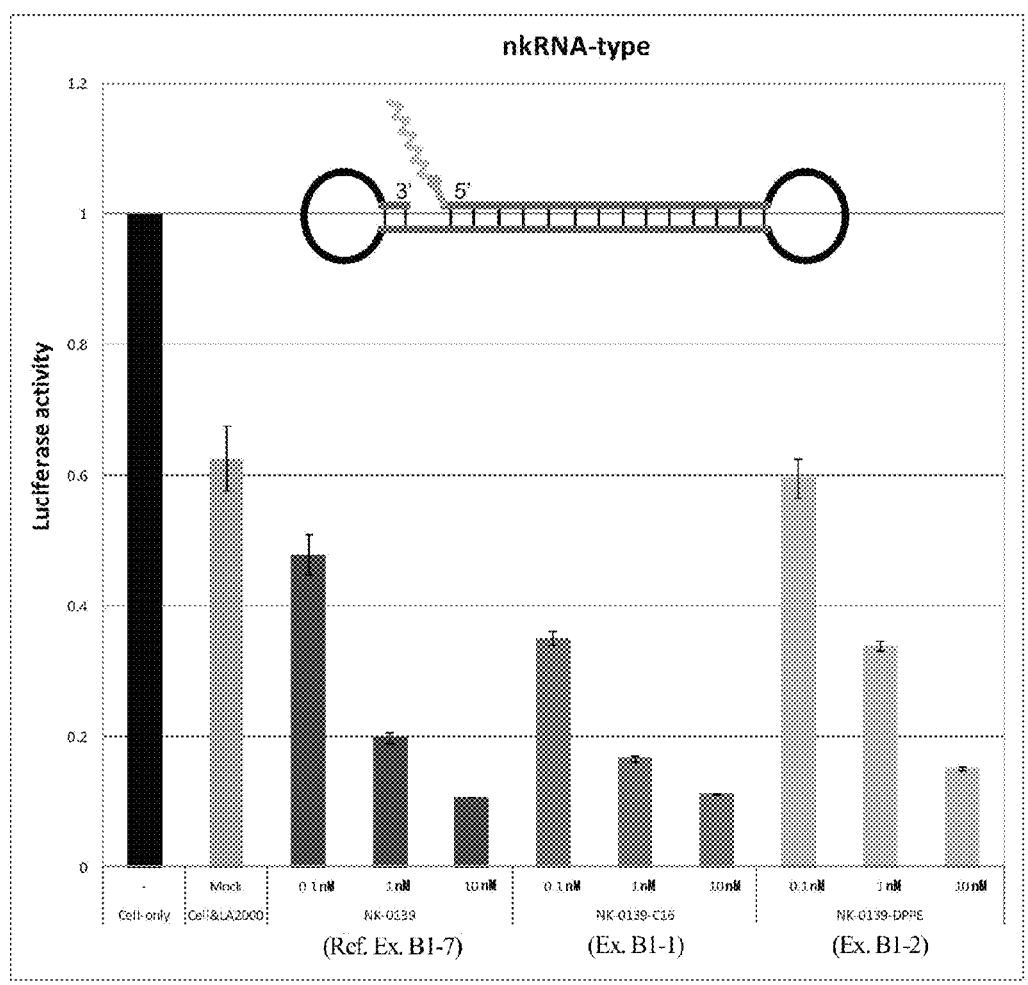
FIG. 4 is another graph showing the firefly luciferase gene expression inhibitory effect (relative activity of luciferase)

The results are shown in FIGS. 3-5. FIGS. 3-5 are graphs showing the relative value of the luciferase activity.

As shown in FIG. 3, Reference Example B1-1 (NI-0089), Reference Example B1-2 (NI-0089-C16) and Reference Example B1-3 (NI-0089-DPPE)), which are of the siRNA type (double-stranded RNA), each showed inhibition of luciferase luminescence. Reference Example B1-4(NI-0000), Reference Example B1-5(NI-0000-C16) and Reference Example B1-6 (NI-0000-DPPE), which are of the siRNA type (double-stranded RNA) having a negative control sequence, did not show inhibition of luciferase luminescence.

As shown in FIG. 4, NK-0139 (Reference Example B1-7), NK-0139-C16 (Example B1-1) and NK-0139-DPPE (Example B1-2), which are of the nkRNA type, each showed inhibition of luciferase luminescence. NK-0139-C16 (Example B1-1) and NK-0139-DPPE (Example B1-2) having a lipid bound to the 5'-terminus thereof (modified) each showed a luciferase activity inhibitory effect not inferior to that of NK-0139 (Reference Example B1-7), to which a lipid was not bound (unmodified). Furthermore, a superior delivering ability to a target can be realized without essentially requiring, for example, a carrier for the delivery, since a lipid (bio-related substance) has been bound. Furthermore, NK-0139-C16 (Example B1-1) and NK-0139-DPPE (Example B1-2) showed a luciferase activity inhibitory effect not inferior to that of Reference Examples B1-1 to B1-3, which are of the siRNA type (double-stranded RNA). Since NK-0139-C16 (Example B1-1) and NK-0139-DPPE (Example B1-2) are single-stranded nucleic acids, they are easily synthesized and handled as compared to the siRNA type (double-stranded RNA).

As shown in FIG. 5, PK-0071 (Reference Example B1-11), PK-0071-C16 (Example B1-3) and PK-0071-DPPE (Example B1-4), which are of the PnkRNA type, each showed inhibition of luciferase luminescence. PK-0071-C16 (Example B1-3) and PK-0071-DPPE (Example B1-4) having a lipid bound to the 5'-terminus thereof (modified) each showed a luciferase activity inhibitory effect not inferior to that of PK-0071 (Reference Example B1-8), to which a lipid was not bound (unmodified). Furthermore, a superior delivering ability to a target can be realized without essentially requiring, for example, a carrier for the delivery, since a lipid (bio-related substance) has been bound. Furthermore, PK-0071-C16 (Example B1-3) and PK-0071-DPPE (Example B1-4) showed a luciferase activity inhibitory effect not inferior to that of Reference Examples B1-1 to B1-3, which are of the siRNA type (double-stranded RNA). Furthermore, since PK-0071-C16 (Example B1-3) and PK-0071-DPPE (Example B1-4) are single-stranded nucleic acids, they are easily synthesized and handled as compared to the siRNA type (double-stranded RNA).

Example A2: Synthesis of Internal Lipid-Conjugated Nucleic Acid

An internal lipid-conjugated nucleic acid wherein a lipid is internally bound to a site other than the terminal of the nucleic acid (to be referred to as "internal lipid conjugate", "internal lipid-modified nucleic acid", or simply "lipid-modified nucleic acid") was synthesized. The structure of the synthesized internal lipid-conjugated nucleic acid is schematically shown below. Among the symbols indicating a nucleic acid ("K(R)-0101-C16" etc.), "K" is the below-mentioned lysine residue and "G" is the below-mentioned glycine residue. "R" shows, in the following drawing, that the linker region (linker region Lx) on the right side is the aforementioned lysine residue or the aforementioned glycine residue. "L" shows, in the following drawing, that the linker region (linker region Ly) on the left side is the aforementioned lysine residue or the aforementioned glycine residue. "LR" shows, in the following drawing, that the linker regions (linker regions Lx and Ly) on the right and left sides are the aforementioned lysine residue or the aforementioned glycine residue. "C16" shows that a single-chain lipid similar to that in Examples A1 and B1 is bound to the aforementioned lysine residue. "DPPE" shows that a double-chain lipid similar to that in Examples A1 and E1 is bound to the aforementioned lysine residue.

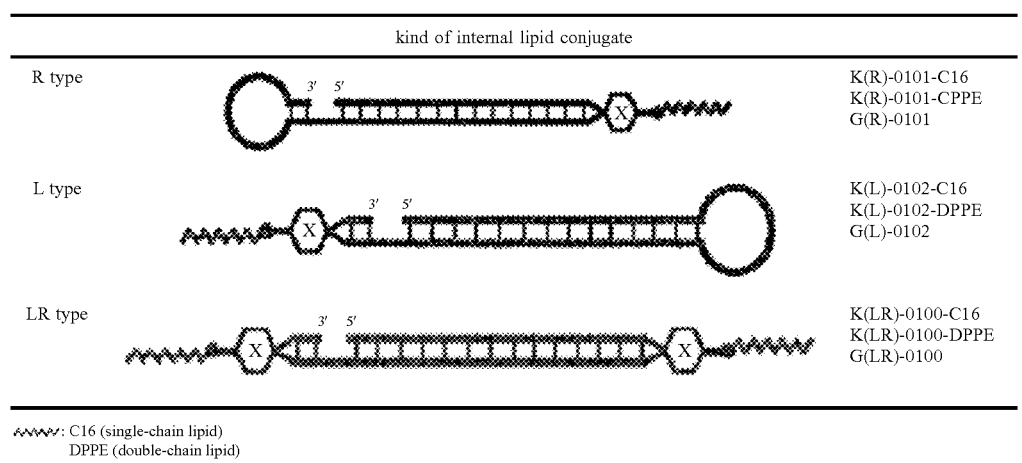

| kind of internal lipid conjugate | | |
|---|---|---|
| R type | | K(R)-0101-C16<br>K(R)-0101-CPPE<br>G(R)-0101 |
| L type | | K(L)-0102-C16<br>K(L)-0102-DPPE<br>G(L)-0102 |
| LR type | | K(LR)-0100-C16<br>K(LR)-0100-DPPE<br>G(LR)-0100 |

∿∿∿: C16 (single-chain lipid)
DPPE (double-chain lipid)

In the above-mentioned internal lipid-conjugated nucleic acid, the "Negative control" has a sequence non-complementary to the target sequence (sequence of firefly luciferase gene, which is retained by the breast cancer cell line MCF-7 stably expressing firefly luciferase (pGL3 Luc)), and corresponds to Reference Example. The "target sequence" is a nucleic acid having a sequence complementary to the aforementioned target sequence. Of the "target sequence", in bound to a site other than the terminal of the single-stranded nucleic acids as mentioned below, and correspond to Examples.

In the aforementioned internal lipid-conjugated nucleic acids, specific sequences and structures of K(R)-0101-C16, K(R)-0101-DPPE and G(R)-0101, which are of the R type, are as follows. In the following structural formulas, "Lys" is a lysine residue of the linker region and "Gly" is a glycine residue of the linker region.

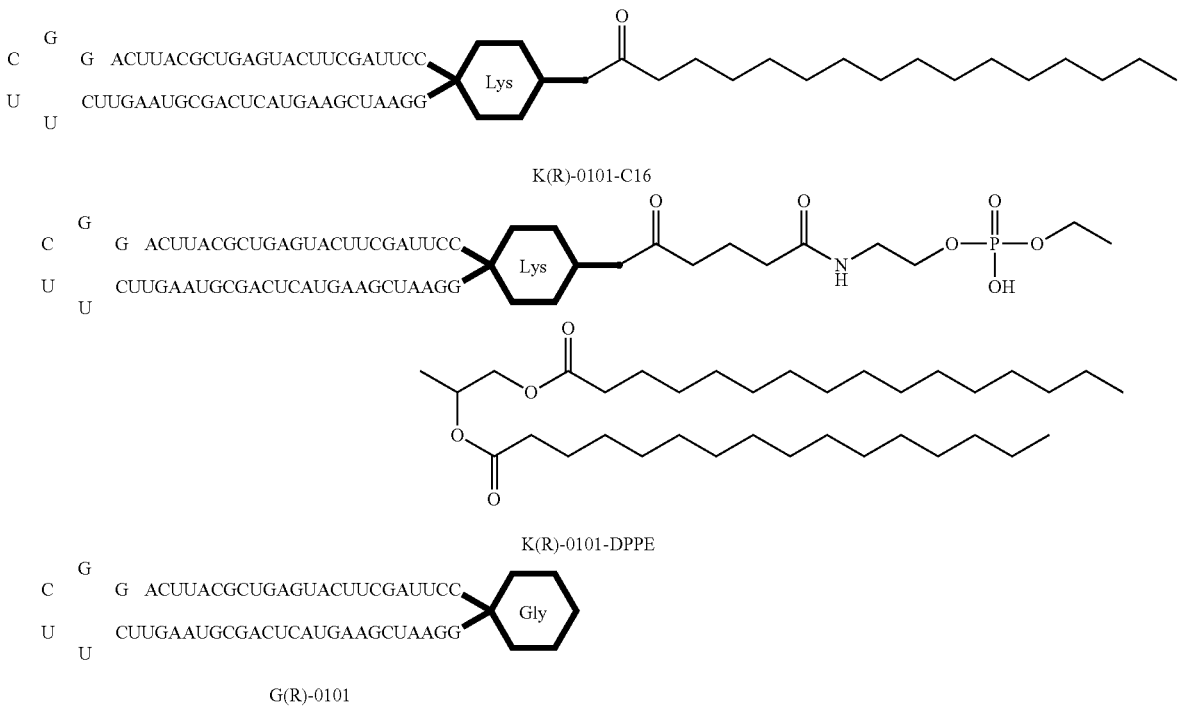

G(R)-0101, G(L)-0102 and G(LR)-0100, a bio-related substance (lipid) is not bound as mentioned below, and they correspond to Reference Example. Of the "target sequences", K(R)-0101-C16, K(R)-0101-DPPE, K(L)-0101-C16, K(L)-0101-DPPE, K(LR)-0101-C16 and K(LR)-0101-DPPE are nucleic acids wherein a lipid is internally Specific structures of K(R)-0101-C16 and G(R)-0101 including Lys (lysine residue) and Gly (glycine residue) are as follows. The structure of lysine residue Lys of K(R)-0101-DPPE is the same as that in K(R)-0101-C16, and the aforementioned double-chain lipid (DPPE) is bound to Lys instead of single-chain lipid (C16).

structure of R type (structural formula)

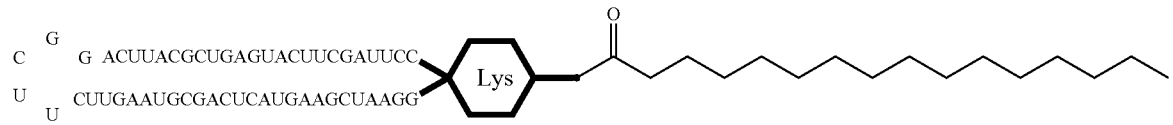

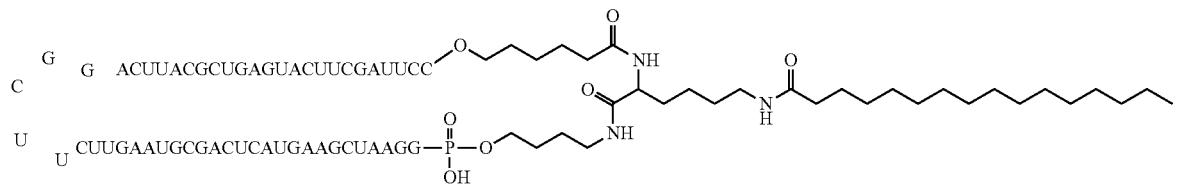

K(R)-0101-C16

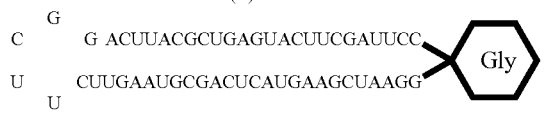

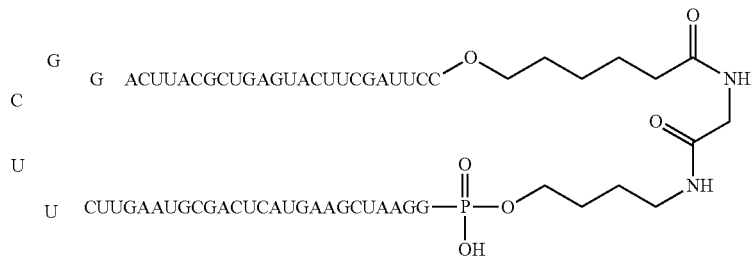

G(R)-0101

The sequences of K(R)-0101-C16 and K(R)-0101-DPPE are shown by the following SEQ ID NO: 11. In the following SEQ ID NO: 11, Ll is the aforementioned lysine residue Lys which is linker region Lx. As mentioned above, in K(R)-0101-C16 and K(R)-0101-DPPE, a lipid is bound to Lys. The sequence of G(R)-0101 is shown by the following SEQ ID NO: 12. In the following SEQ ID NO: 12, Lg is the aforementioned glycine residue Gly which is linker region Lx.

(SEQ ID NO: 11)
5'-ACUUACGCUGAGUACUUCGAUUCC-Ll-GGAAUCGAAGUACUCA

-continued
GCGUAAGUUCUUCGG-3'

(SEQ ID NO: 12)
5'-ACUUACGCUGAGUACUUCGAUUCC-Lg-GGAAUCGAAGUACUCA

GCGUAAGUUCUUCGG-3'

Specific sequences and structures of K(L)-0102-C16, K(L)-0102-DPPE and G(L)-0102, which are of the L type, in the aforementioned internal lipid-conjugated nucleic acids, are as follows. In the following structural formulas, "Lys" is a lysine residue of the linker region and "Gly" is a glycine residue of the linker region. The structures of Lys and Gly are the same as that of the aforementioned R type.

structure of LR type

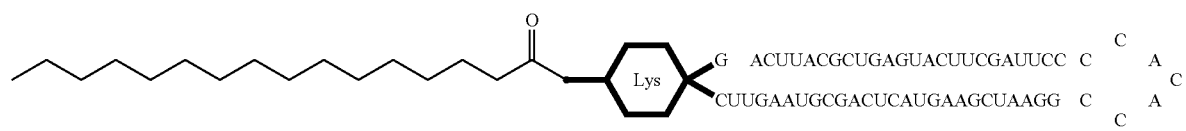

K(L)-0102-C16

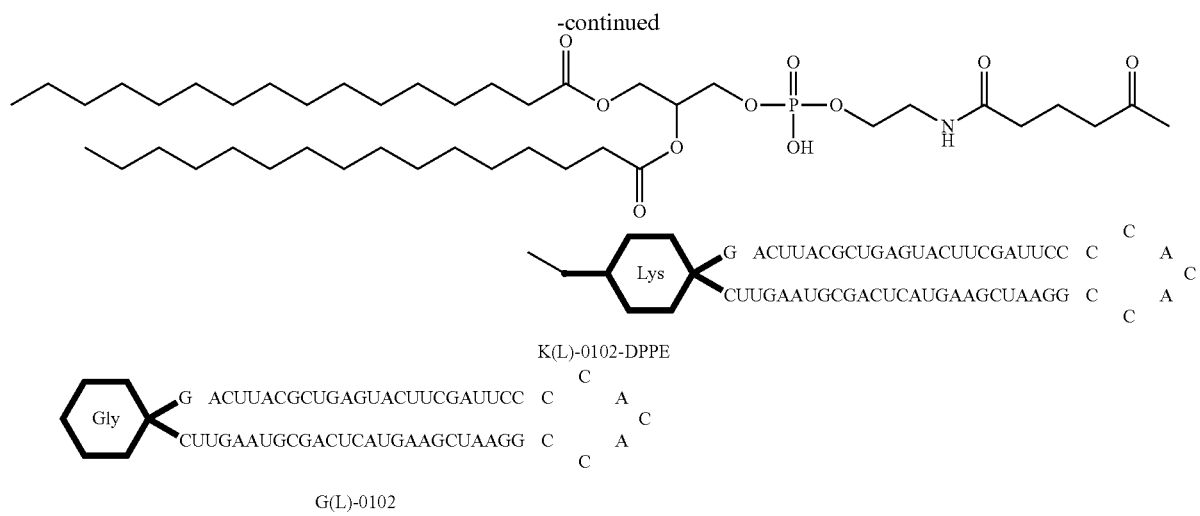

K(L)-0102-DPPE

G(L)-0102

The sequences of K(L)-0102-C16 and K(L)-0102-DPPE are shown by the following SEQ ID NO: 13. In the following SEQ ID NO: 13, Ll is the aforementioned lysine residue Lys which is linker region Ly. As mentioned above, in K(L)-0102-C16 and K(L)-0102-DPPE, a lipid is bound to Lys. The sequence of G(L)-0102 is shown by the following SEQ ID NO: 14. In the following SEQ ID NO: 14, Lg is the aforementioned glycine residue Gly which is linker region Ly.

```
                                      (SEQ ID NO: 13)
5'-ACUUACGCUGAGUACUUCGAUUCCCCACACCGGAAUCGAAGUAC
UCAGCGUAAGUUC-Ll-G-3'

(SEQ ID NO: 14)
5'-ACUUACGCUGAGUACUUCGAUUCCCCACACCGGAAUCGAAGUAC
UCAGCGUAAGUUC-Lg-G-3'
```

Specific sequences and structures of K(LR)-0100-C16, K(LR)-0100-DPPE and G(LR)-0100, which are of the LR type, in the aforementioned internal lipid-conjugated nucleic acids, are as follows. In the following structural formulas, "Lys" is a lysine residue of the linker region and "Gly" is a glycine residue of the linker region. The structures of Lys and Gly are the same as those of the aforementioned R type and the aforementioned L type.

structure of LR type

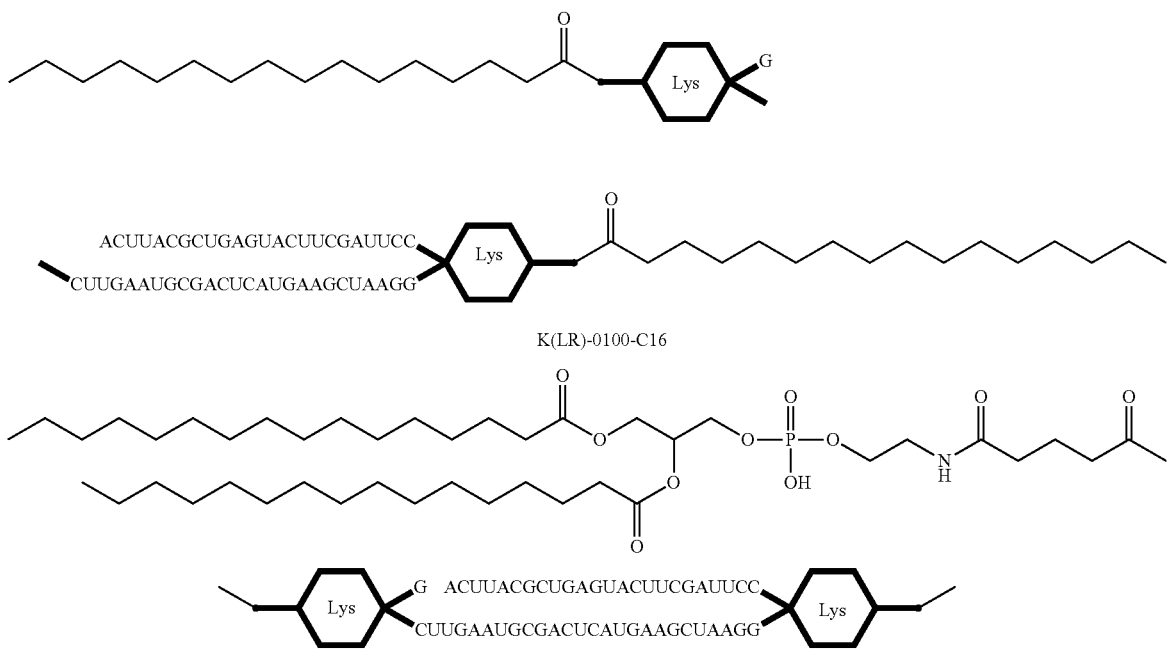

K(LR)-0100-C16

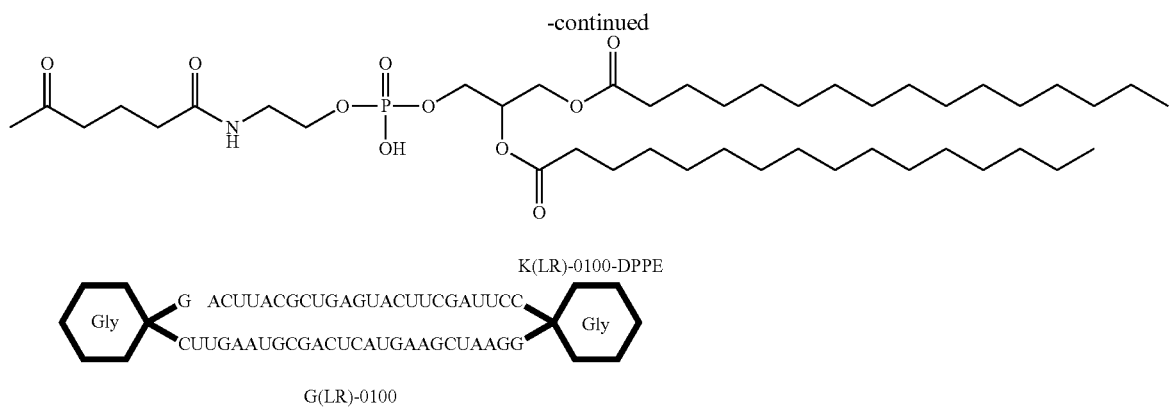

K(LR)-0100-DPPE

G(LR)-0100

The sequences of K(LR)-0100-C16 and K(LR)-0100-DPPE are shown by the following SEQ ID NO: 15. In the following SEQ ID NO: 15, Ll is the aforementioned lysine residue Lys which is linker region Ly. As mentioned above, in K(LR)-0100-C16 and K(LR)-0100-DPPE, a lipid is bound to Lys. The sequence of G(LR)-0100 is shown by the following SEQ ID NO: 16. In the following SEQ ID NO: 16, Lg is the aforementioned glycine residue Gly which is linker region Ly.

(SEQ ID NO: 15)
5'-ACUUACGCUGAGUACUUCGAUUCC-L1-GGAAUCGAAGUACUCA

GCGUAAGUUC-L1-G-3'

(SEQ ID NO: 16)
5'-ACUUACGCUGAGUACUUCGAUUCC-Lg-GGAAUCGAAGUACUCA

GCGUAAGUUC-Lg-G-3'

Each of the aforementioned RNAs (internal lipid-conjugated nucleic acid) was synthesized as follows.

Synthesis of K(R)-0101

K(R)-0101 having the same structure (the aforementioned SEQ ID NO: 11) as that of K(R)-0101-C16 and K(R)-0101-DPPE except that a lipid is not bound to Lys was synthesized according to a phosphoramidite method similar to that mentioned above. To be specific, the aforementioned compound 7 was first linked to 5'-side of the nucleic acid shown by the following SEQ ID NO: 17 to introduce a lysine residue. Then, the RNA shown by the aforementioned SEQ ID NO: 3 was linked to the 5'-side of the nucleic acid shown by the aforementioned SEQ ID NO: 17 via the aforementioned lysine residue, whereby K(R)-0101 was synthesized.

(SEQ ID NO: 17)
5'-GGAAUCGAAGUACUCAGCGUAAGUUCUUCGG-3'

Synthesis of K(R)-0101-C16

K(R)-0101 (500 µM, 80 µL), 50 mM C16-NHS/DMF solution (32 µL), isopropanol (128 µL) and carbonate buffer (pH 9.2, 160 µL) (final concentration 100 mM) were mixed, and the mixture was stirred at 40° C. for 3 hr. The reaction liquid was purified by HPLC (Develosil C8-UG-5, 2.5 mm, 10×50 mm, 4.7 mL/min, 260 nm, 35° C., Buffer A: 50 mM TEAA, 5% CH$_3$CN; Buffer B: CH$_3$CN; B conc. 0-100%/20 min), and the peak of the object product was fractionated. The fraction obtained by fractionation was precipitated in ethanol, and the resulting precipitate was dissolved in distilled water for injection. The absorbance at UV 260 nm was measured, and the yield was calculated. In this way, K(R)-0101-C16 (405 µg, purity 99.50%) was obtained. The mass spectrometry value was 18203.18 (Calculated: 18203.41).

Synthesis of K(L)-0102-C16

By a method similar to that for K(R)-0101-C16 except that the aforementioned SEQ ID NO: 17 was changed to guanosine and the aforementioned SEQ ID NO: 3 was changed to the following SEQ ID NO: 18, synthesis was performed to give K(L)-0102-C16 (316 µg, purity 96.69%). The mass spectrometry value was 19124.88 (Calculated: 19125.01).

(SEQ ID NO: 18)
5'-ACUUACGCUGAGUACUUCGAUUCCCCACACCGGAAUCGAAGUAC

UCAGCGUAAGUUC-3'

Synthesis of K(LR)-0100

K(LR)-0100 having the same structure (the aforementioned SEQ ID NO: 11) as that of K(LR)-0100-C16 and K(LR)-0100-DPPE except that a lipid is not bound to Lys was synthesized according to a phosphoramidite method similar to that mentioned above. To be specific, the aforementioned compound 7 was first linked to 5'-side of the nucleic acid shown by guanosine to introduce a lysine residue. Then, the nucleic acid shown by the following SEQ ID NO: 19 was introduced to the 5'-side of the aforementioned guanosine via the aforementioned lysine residue. Furthermore, the aforementioned compound 7 was linked to the 5'-side of the nucleic acid shown by the aforementioned SEQ ID NO: 19 to introduce a lysine residue. Moreover, the RNA shown by the aforementioned SEQ ID NO: 3 was linked to the 5'-side of the nucleic acid shown by the aforementioned SEQ ID NO: via the aforementioned lysine residue, whereby K(LR)-0100 was synthesized.

(SEQ ID NO: 19)
5'-GGAAUCGAAGUACUCAGCGUAAGUUC-3'

Synthesis of K(LR)-0100-C16

By a method similar to that for K(R)-0101-C16 except that K(LR)-0100 was used instead of K(R)-0101, synthesis was performed to give K(LR)-0100-C16 (317 μg, purity 98.07%). The mass spectrometry value was 17572.21 (Calculated: 17572.52).

Synthesis of K(R)-0101-DPPE

K(R)-0101 (500 μM, 160 μL), 10 mM DPPE-NHS ethanol solution (320 μL), 1% aqueous triethylamine solution (80 μL), ethanol (160 μL) and distilled water for injection (80 μL) were mixed, and the mixture was stirred at 40° C. for 24 hr. The reaction liquid was purified by HPLC (Develosil C8-UG-5, 2.5 mm, 10×50 mm, 4.7 mL/min, 260 nm, 35° C., Buffer A: 50 mM TEAA, 5% $CH_3CN$; Buffer B: $CH_3CN$; B conc. 0-100%/20 min), and the peak of the object product was fractionated. The fraction obtained by fractionation was precipitated in ethanol, and the resulting precipitate was dissolved in distilled water for injection. The absorbance at UV 260 nm was measured, and the yield was calculated. In this way, K(R)-0101-DPPE (0.98 mg, purity 99.55%) was obtained. The mass spectrometry value was 18752.70 (Calculated: 18753.04).

Synthesis of K(L)-0102-DPPE

By a method similar to that for K(R)-0101-DPPE except that the aforementioned SEQ ID NO: 17 was changed to guanosine and the aforementioned SEQ ID NO: 3 was changed to the aforementioned SEQ ID NO: 18, synthesis was performed to give K(L)-0102-DPPE (1.05 mg, purity 99.10%). The mass spectrometry value was 19674.36 (Calculated: 19674.64).

Synthesis of K(LR)-0100-DPPE

K(LR)-0100 (500 μM, 120 μL), 10 mM DPPE-NHS ethanol solution (360 μL), 1% aqueous triethylamine solution (90 μL) and distilled water for injection (30 μL) were mixed, and the mixture was stirred at 40° C. for 24 hr. The reaction liquid was purified by HPLC (Develosil C8-UG-5, 2.5 mm, 10×50 mm, 4.7 mL/min, 260 nm, 35° C., Buffer A: 50 mM TEAA, 5% $CH_3CN$; Buffer B: $CH_3CN$; B conc. 0-100%/20 min), and the peak of the object product was fractionated. The fraction obtained by fractionation was precipitated in ethanol, and the resulting precipitate was dissolved in distilled water for injection. The absorbance at UV 260 nm was measured, and the yield was calculated. In this way, K(LR)-0100-DPPE (0.54 mg, purity 99.14%) was obtained. The mass spectrometry value was 18670.42 (Calculated: 18671.78).

(Example B2) Inhibitory Effect of Internal Lipid-Conjugated Nucleic Acid on Expression of Firefly Luciferase Gene In the same manner as in Example B1 except that the aforementioned internal lipid-conjugated nucleic acid was used instead of the aforementioned 5'-terminus lipid-conjugated nucleic acid, inhibition of the expression of firefly luciferase gene in vitro was confirmed. These results are shown in FIGS. 6-8. FIGS. 6-8 are graphs showing the relative values of the luciferase activity.

As shown in FIGS. 6-8, G(R)-0101 (Reference Example B2-1), K(R)-0101-C16 (Example B2-1), K(R)-0101-DPPE (Example B2-2), G(L)-0102 (Reference Example B2-2), K(L)-0102-C16 (Example B2-3), K(L)-0102-DPPE (Example B2-4), G(LR)-0100 (Reference Example B2-3), K(LR)-0100-C16 (Example B2-5) and K(LR)-0100-DPPE (Example B2-6) each exhibited inhibition of luciferase luminescence.

In addition, as shown in FIGS. 6-8, K(R)-0101-C16 (Example B2-1), K(R)-0101-DPPE (Example B2-2), K(L)-0102-016 (Example B2-3), K(L)-0102-DPPE (Example B2-4), K(LR)-0100-016 (Example B2-5) and K(LR)-0100-DPPE (Example B2-6) having a lipid bound in the inside other than the terminus thereof (modified) each exhibited a luciferase activity inhibitory effect not inferior to that of G(R)-0101 (Reference Example B2-1), G(L)-0102 (Reference Example B2-2) and G(LR)-0100 (Reference Example B2-3), to which a lipid was not bound (unmodified). Furthermore, a superior delivering ability to a target can be realized without essentially requiring, for example, a carrier for the delivery, since a lipid (bio-related substance) has been bound. In addition, the nucleic acids of the aforementioned Examples B2-1-B2-6 showed a luciferase activity inhibitory effect not inferior to that of Reference Examples B1-1 to B1-3, which are of the siRNA type (double-stranded RNA). Furthermore, since they are single-stranded nucleic acids, they are easily synthesized and handled as compared to the siRNA type (double-stranded RNA).

Example A3: Synthesis of Internal Lipid-Conjugated Nucleic Acid with Altered Lipid Structure K(R)-0101-C14, K(R)-0101-C18 and K(R)-0101-C18:1 were synthesized, which are nucleic acids wherein the lipid structure of K(R)-0101-C16 (an R type nucleic acid of the aforementioned Example A2) was changed from C16 (palmitic acid) to C14 (myristic acid), C18 (stearic acid) and C18 (oleic acid) having one unsaturated bond, respectively. Respective structures thereof are as follows.

| | internal lipid conjugate (R type; FA) | |
|---|---|---|
| Type | Figure | Target sequence |
| R type | 3' 5' ⬡━━━━━━X━∿∿∿ | K(R)-0101-C16 K(R)-0101-C14 K(R)- |

-continued

| Type | Figure | | Target sequence |
|---|---|---|---|
| | | | 0101-C18 K(R)-0101-C18:1 G(R)-0101 |
| | 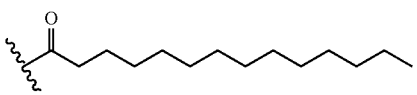 [SMILES: *C(=O)CCCCCCCCCCCCC] | C16 (palmitic acid) | K(R)-0101-C16 |
| | | C14 (myristic acid) | |
| | | C18 (stearic acid) | |
| | | C18:1 (oleic acid) | |

Synthesis of K(R)-0101-C14

K(R)-0101 (500 µM, 40 µL), 50 mM C14-NHS/DMF solution (16 µL), isopropanol (64 µL) and carbonate buffer (pH 9.2, 80 µL) (final concentration 100 mM) were mixed, and the mixture was stirred at 40° C. for 3 hr. The reaction liquid was purified by HPLC (Develosil C8-UG-5, 2.5 mm, 10×50 mm, 4.7 mL/min, 260 nm, 35° C., Buffer A: 50 mM TEAA, 5% CH$_3$CN; Buffer B: CH$_3$CN; B conc. 0-100%/20 min), and the peak of the object product was fractionated. The fraction obtained by fractionation was precipitated in ethanol, and the resulting precipitate was dissolved in distilled water for injection. The absorbance at UV 260 nm was measured, and the yield was calculated. In this way, K(R)-0101-C14 (193 µg, purity 94.43%) was obtained. The mass spectrometry value was 18175.91 (Calculated: 18175.36).

Synthesis of K(R)-0101-C18

K(R)-0101 (500 µM, 40 µL), 50 mM C18-NHS/DMF solution (16 µL), isopropanol (64 µL) and carbonate buffer (pH 9.2, 80 µL) (final concentration 100 mM) were mixed, and the mixture was stirred at 40° C. for 3 hr. The reaction liquid was purified by HPLC (Develosil C8-UG-5, 2.5 mm, 10×50 mm, 4.7 mL/min, 260 nm, 35° C., Buffer A: 50 mM TEAA, 5% CH$_3$CN; Buffer B: CH$_3$CN; B conc. 0-100%/20 min), and the peak of the object product was fractionated. The fraction obtained by fractionation was precipitated in ethanol, and the resulting precipitate was dissolved in distilled water for injection. The absorbance at UV 260 nm was measured, and the yield was calculated. In this way, K(R)-0101-C18 (188 µg, purity 95.97%) was obtained. The mass spectrometry value was 18231.08 (Calculated: 18231.46).

Synthesis of K(R)-0101-C18:1

K(R)-0101 (500 µM, 40 µL), 50 mM C18:1-NHS/DMF solution (16 µL), isopropanol (64 µL) and carbonate buffer (pH 9.2, 80 µL) (final concentration 100 mM) were mixed, and the mixture was stirred at 40° C. for 3 hr. The reaction liquid was purified by HPLC (Develosil C8-UG-5, 2.5 mm, 10×50 mm, 4.7 mL/min, 260 nm, 35° C., Buffer A: 50 mM TEAA, 5% CH$_3$CN; Buffer B: CH$_3$CN; B conc. 0-100%/20 min), and the peak of the object product was fractionated. The fraction obtained by fractionation was precipitated in ethanol, and the resulting precipitate was dissolved in distilled water for injection. The absorbance at UV 260 nm was measured, and the yield was calculated. In this way, K(R)-0101-C18:1 (192 µg, purity 96.22%) was obtained. The mass spectrometry value was 18230.49 (Calculated: 18229.45).

(Example B3) Inhibitory Effect of Internal Lipid-Conjugated Nucleic Acid Having Changed Lipid Structure on Expression of Firefly Luciferase Gene In the same manner as in Example B2 except that K(R)-0101-C14, K(R)-0101-C18 and K(R)-0101-C18:1 were used instead of K(R)-0101-C16, inhibition of the expression of firefly luciferase gene in vitro was confirmed (Example B3-2 to Example B3-4). In addition, inhibition of the expression was also confirmed in the same manner for G(R)-0101 (Reference Example B3-1) and K(R)-0101-C16 (Example B3-1). These results are shown in FIG. 9. FIG. 9 is a graph showing the relative values of the luciferase activity. As shown in the Figure, the inhibitory effect on the luciferase activity was mostly in the order of C14 modification<C18:1 modification<C16 modification<C18:0 modification, but much difference was not found. That is, since all of Example B3-2 to Example B3-4 showed a luciferase activity inhibitory effect not inferior to that in Example B3-1, it was confirmed that the effect of the present invention can be obtained even when the structure of the lipid is changed. In addition, Examples B3-1 to B3-4 showed a luciferase activity inhibitory effect not inferior to that in Reference Example B3-1, to which a lipid was not bound.

Example C4

The effect of K(R)-0101-C16 in vivo was examined as in the following by using a mouse constitutively expressing a firefly luciferase gene (Luciferase transgenic mouse). That is, Luciferase transgenic mice (C57Blac/J) (♀4-week-old) were prepared (2 groups, 5 mice each group). To one group, K(R)0101-C16 was administered from the tail vein at 200 μg/100 μL/head. Nothing was administered to the other group (untreated). Four days after the administration, D-Luciferin (Promega) was intraperitoneally administered at 3 mg/head, and the mice were autopsied under ether anesthesia, each organ was isolated. The chemical luminescence intensity was measured for 15 min by IVIS Imaging System (Caliper Co.,) and the results were analyzed.

The photographs of FIG. 10 shows the measurement results of the inhibition of the expression of firefly luciferase gene by the aforementioned IVIS assay. FIG. 10(a) is a photograph showing the measurement results of the mouse treated with the single-stranded nucleic acid (K(R)0101-C16) of the present invention. FIG. 10(b) is a photograph showing the measurement results of the untreated mouse.

FIG. 11 is a graph showing the measurement results of the systemic luciferase activity (inhibition of expression of firefly luciferase gene) in the photograph of FIG. 10. FIG. 12 is a graph showing the measurement results of the luciferase activity in the brain (inhibition of expression of firefly luciferase gene) in the photograph of FIG. 10. In FIGS. 11 and 12, the vertical axis shows the luciferase activity, "Nontreat" shows the measurement results of the untreated mouse, and "K(R)-0101-C16" shows the measurement results of the mouse treated with K(R)-0101-C16. As shown in the Figures, the mouse treated with K(R)-0101-C16 showed a clear decrease in the luciferase activity as compared to the untreated mouse, and a luciferase activity inhibitory effect was found. Also, as shown in FIG. 12, since the mouse treated with K(R)-0101-C16 showed a decrease in the luciferase activity in the brain, the nucleic acid of the present invention can pass through the blood-brain barrier and inhibit the gene expression in the brain. Furthermore, a superior delivering ability to a target can be realized without essentially requiring, for example, a carrier for the delivery, since a lipid (bio-related substance) has been bound.

While the present invention has been described above with reference to illustrative embodiments, the present invention is by no means limited thereto. Various changes that may become apparent to those skilled in the art may be made in the configuration and specifics of the present invention without departing from the scope of the present invention.

INDUSTRIAL APPLICABILITY

The single-stranded nucleic acid molecule of the present invention can realize a superior delivering ability to a target without essentially requiring, for example, a carrier for the delivery. Therefore, for example, the toxicity of the carrier does not need to be considered, and a study for setting various conditions relating to the formation of a complex of a nucleic acid molecule and a carrier can be obviated. Consequently, for example, the labor and cost in terms of production and use can be reduced.

The invention claimed is:

1. An isolated molecule for inhibiting expression of a target gene, wherein the molecule has a delivery function and comprises, in the following order, a 5'-side region (Xc), a linker region (Lx), an inner region (Z), a linker region (Ly) and a 3'-side region (Yc) which regions are linked together, wherein the inner region (Z) is constituted by linkage of an inner 5'-side region (X) and an inner 3'-side region (Y), the 5'-side region (Xc), the inner 5'-side region (X), the inner 3'-side region (Y) and the 3'side region (Yc) are each composed of a nucleotide residue or a nucleotide sequence, the 5'-side region (Xc) is complementary to the inner 5'-side region (X), the 3'-side region (Yc) is complementary to the inner 3'-side region (Y), at least one of the inner region (Z), the 5'-side region (Xc) and the 3'-side region (Yc) comprises an expression inhibitory sequence that inhibits expression of a target gene, the linker region (Lx) is linked to the 3'-end of the 5'-side region (Xc) and the 5'-end of the inner 5'-side region (X), the linker region (Ly) is linked to the 3'-end of the inner 3'-side region (Y) and the 5'-end of the 3'-side region (Yc), the linker region (Lx) and the linker region (Ly) are each composed of a nucleotide or non-nucleotide residue or a sequence of at least one nucleotide and non-nucleotide residues, wherein at least one selected from the group consisting of the linker region (Lx) and the linker region (Ly) comprises a lysine residue in such a manner that (i) the 5'-side region (Xc) and the inner 5'-side region (X) or (ii) the inner 3'-side region (Y) and the 3'-side region (Yc) are linked together via the lysine residue, and a lipid is covalently bound to the molecule via the lysine residue.

2. The molecule according to claim 1, wherein the lipid is a simple lipid, complex lipid, derived lipid, single-chain lipid, double-chain lipid, glycolipid, liposoluble vitamin or steroid.

3. The molecule according to claim 1, wherein the lipid is at least one selected from the group consisting of palmitic acid, myristic acid, stearic acid and oleic acid.

4. The molecule according to claim 1, wherein at least one selected from the group consisting of an antibody protein, a peptide thereof and a membrane-permeable peptide is covalently bound to at least one selected from the group consisting of the 5'-terminus of the 5'-side region (Xc), the 3'-terminus of the 3'-side region (Yc), the linker region (Lx) and the linker region (Ly).

5. The molecule according to claim 1, which satisfies the following conditions of the formulas (1) and (2):

$$Z = X + Y \tag{1}$$

$$Z \geq Xc + Yc \tag{2}$$

wherein Z is a base number of the inner region (Z), X is a base number of the inner 5'-side region (X), Y is a base number of the inner 3'-side region (Y), Xc is a base number of the 5'-side region (Xc) and Yc is a base number of the 3'-side region (Yc).

6. The molecule according to claim 1, which comprises at least one modified nucleotide residue.

7. The molecule according to claim 1, which comprises a stable isotope.

8. The molecule according to claim 1, which comprises a non-modified nucleotide residue and/or a modified nucleotide residue.

9. The molecule according to claim 1, wherein the linker region (Lx) or the linker region (Ly), which does not comprise a lysine residue, is composed of any of the residues of the following (1)-(7):
(1) a non-modified nucleotide residue,
(2) a modified nucleotide residue,
(3) a non-modified nucleotide residue and a modified nucleotide residue,
(4) a non-nucleotide residue,
(5) a non-nucleotide residue and a non-modified nucleotide residue,
(6) a non-nucleotide residue and a modified nucleotide residue, and
(7) a non-nucleotide residue, a non-modified nucleotide residue and a modified nucleotide residue.

10. The molecule according to claim 1, wherein inhibiting expression of the target gene is effected by RNA interference.

11. The molecule according to claim 1, wherein the sequence of the residues in the molecule is the sequence of SEQ ID NO: 11, 13, or 15.

12. A composition for inhibiting an expression of a target gene, comprising a molecule according to claim 1.

13. A pharmaceutical composition comprising a molecule according to claim 1.

14. A method of inhibiting an expression of a target gene, comprising contacting a cell with a molecule according to claim 1.

15. The method according to claim 14, comprising a step of administering the molecule to a cell, tissue or organ.

16. The method according to claim 15, wherein the molecule is administered in vivo or in vitro.

17. The method according to claim 14, wherein the gene expression inhibition is an expression inhibition by RNA interference.

18. A method of inducing RNA interference to inhibit expression of a target gene, comprising contacting a cell with the molecule according to claim 1.

19. A method of treating a disease, comprising a step of administering a molecule according to claim 1 to a patient to inhibit expression of a target gene causing the disease.

20. The molecule according to claim 1, wherein at least one selected from the group consisting of the linker region (Lx) and the linker region (Ly) is composed of one lysine residue in such a manner that (i) the 5'-side region (Xc) and the inner 5'-side region (X) or (ii) the inner 3'-side region (Y) and the 3'-side region (Yc) are linked together via the lysine residue.

* * * * *